United States Patent
Masujima et al.

(10) Patent No.: US 9,502,227 B2
(45) Date of Patent: Nov. 22, 2016

(54) CAPTURING OF CELL FLUID AND ANALYSIS OF ITS COMPONENTS UNDER OBSERVATION OF CELLS AND INSTRUMENTS FOR THE CELL FLUID CAPTURING AND THE ANALYSIS

(71) Applicant: HUMANIX CO., LTD., Hiroshima-shi (JP)

(72) Inventors: Tsutomu Masujima, Hiroshima (JP); Naohiro Tsuyama, Hiroshima (JP); Hajime Mizuno, Hiroshima (JP)

(73) Assignee: HUMANIX CO., LTD., Hiroshima-shi (JP)

( * ) Notice: Subject to any disclaimer, the term of this patent is extended or adjusted under 35 U.S.C. 154(b) by 13 days.

(21) Appl. No.: 14/194,555

(22) Filed: Feb. 28, 2014

(65) Prior Publication Data

US 2014/0315237 A1      Oct. 23, 2014

Related U.S. Application Data

(63) Continuation-in-part of application No. 12/739,660, filed as application No. PCT/JP2008/070060 on Nov. 4, 2008, now abandoned.

(30) Foreign Application Priority Data

Nov. 2, 2007   (JP) ................. 2007-286208
Apr. 1, 2008   (JP) ................. 2008-095092

(51) Int. Cl.
  *G01N 27/62*   (2006.01)
  *G01N 33/48*   (2006.01)
  (Continued)

(52) U.S. Cl.
  CPC ............. *H01J 49/167* (2013.01); *G01N 27/62* (2013.01); *G01N 33/48* (2013.01); *H01J 49/04* (2013.01); *Y10T 436/24* (2015.01)

(58) Field of Classification Search
  CPC ...... H01J 49/04; H01J 49/167; G01N 27/62; G01N 33/48; Y10T 436/24; Y10T 436/25; Y10T 436/2575

USPC ........... 436/63, 149, 150, 173, 174, 180; 422/68.1, 82.01, 501, 520, 524; 435/4, 435/29, 30, 325, 287.1; 250/281, 282
  See application file for complete search history.

(56) References Cited

U.S. PATENT DOCUMENTS 6,297,499 B1   10/2001   Fenn
6,670,607 B2   12/2003   Wood et al.
(Continued)

FOREIGN PATENT DOCUMENTS

JP   2002-537561 A   11/2002
JP   2005-503537 A    2/2005
(Continued)

OTHER PUBLICATIONS

Extended European Search Report dated Mar. 20, 2015 issued in application No. 14195512.0.
(Continued)

*Primary Examiner* — Maureen Wallenhorst
(74) *Attorney, Agent, or Firm* — Knobbe Martens Olson & Bear LLP

(57) ABSTRACT

A method captures cellular components from a single cell and performs mass spectrometry on the components. The method includes inserting a nanospray ionization capillary tip into a specific region of the cell under observation with a microscope. The nanospray ionization capillary tip can include a filament in the interior. The method further includes capturing the cellular components of the specific region of the cell into the opening of the nanospray ionization capillary tip and keeping the components at the nanospray ionization capillary tip, supplying an ionization supporting solvent from a back-end of the nanospray ionization capillary tip, applying an electric field between a sample inlet of a mass spectrometer and the nanospray ionization capillary tip, whereby nanospray ionization to the cellular components is implemented, and performing the mass spectrometry on the cellular components captured at the nanospray ionization capillary tip.

24 Claims, 63 Drawing Sheets

Figure 2:
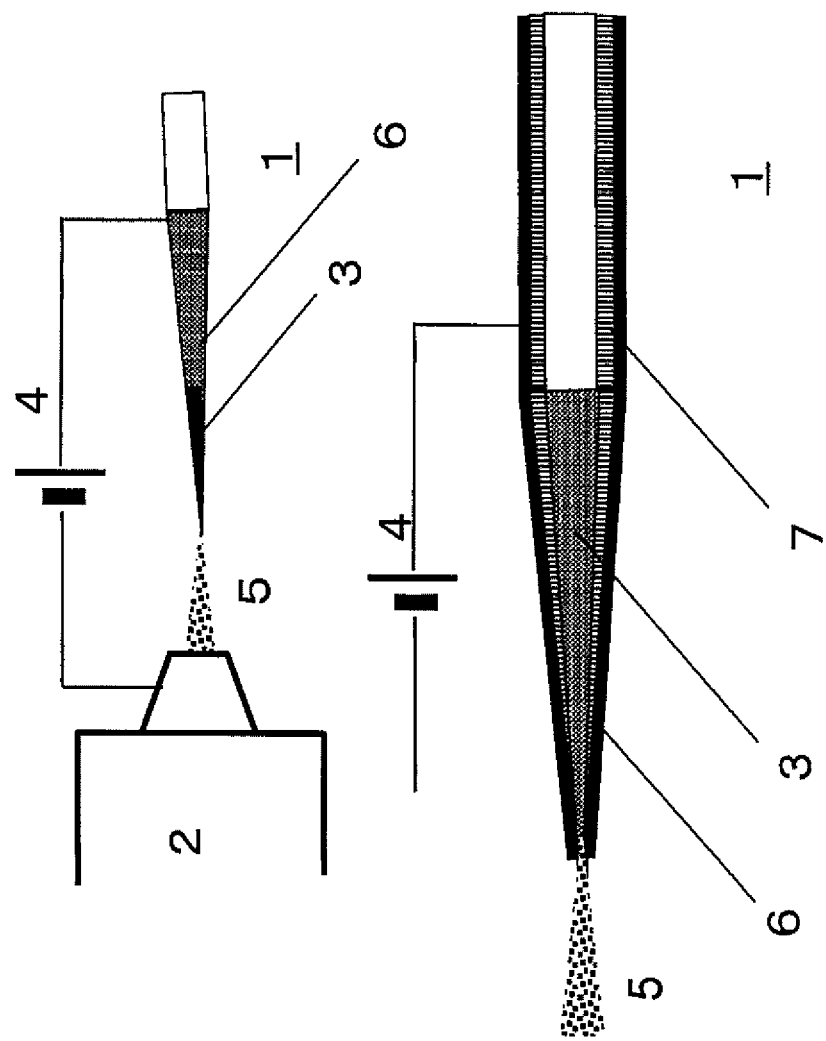

(51) Int. Cl.
*H01J 49/04* (2006.01)
*H01J 49/16* (2006.01)
*C12Q 1/02* (2006.01)
*C12M 1/34* (2006.01)

(56) References Cited

U.S. PATENT DOCUMENTS

| | | |
|---|---|---|
| 7,087,895 B1 | 8/2006 | Liu et al. |
| 7,186,974 B2 | 3/2007 | Tojo |
| 2006/0022131 A1 | 2/2006 | Tojo |
| 2006/0208186 A1 | 9/2006 | Goodley et al. |
| 2007/0023676 A1 | 2/2007 | Goodley et al. |
| 2011/0089319 A1 | 4/2011 | Isobe et al. |

FOREIGN PATENT DOCUMENTS

| | | |
|---|---|---|
| JP | 2005-190767 A | 7/2005 |
| JP | 2006-261116 A | 9/2006 |
| JP | 2006-524418 A | 10/2006 |
| WO | WO 00/49410 A1 | 8/2000 |
| WO | WO 02/082051 A2 | 10/2002 |

OTHER PUBLICATIONS

Kentaro Yamaguchi et al., Mass spectrometry of biological molecules focused on soft-ionization method such as MALDI developed by Mr. Tanaka and ESI, Pharmacia, 2003, vol. 39, No. 2, pp. 143 to 147.

Yasuyuki Hirakawa et al., Development of mass spectrometry for the direct dynamic analysis of molecules related to cells, Bunseki Kagaku vol. 53, No. 6, 2004 The Japan Society for Analytical Chemistry, pp. 519-526.

Tsutomu Masujima et al., Development of video-massscope; —Current status and development—, The Japan Society of Analytical Chemistry, Sep. 5, 2007, p. 70, C3008.

Hajime Mizuno et al., Development of video-massscope; single cell molecular trapping mass spectrometry, The Japan Society of Analytical Chemistry, Sep. 5, 2007, p. 72, C3011.

Sirikatitham et al., Resin-packed nanoelectrospray in combination with video and mass spectrometry for the direct and real-time molecular analysis of mast cells, Rapid Commun. Mass Sectrom., 2007, pp. 385-390, vol. 21.

Masujima, Tsutomu, Live single-cell mass spectrometry, Analytical Sciences, Aug. 2009, pp. 953-960, vol. 25.

Tsuyama et al., Mass spectrometry for cellular and tissue analyses in a very small region, Analytical Sciences, Feb. 2011, pp. 163-170, vol. 27.

Extended European Search Report dated Jul. 26, 2011 for Corresponding Application No. 08849746.

Office Action mailed Mar. 11, 2013 in corresponding Japanese Patent Application No. 2009-541101.

FIG.1
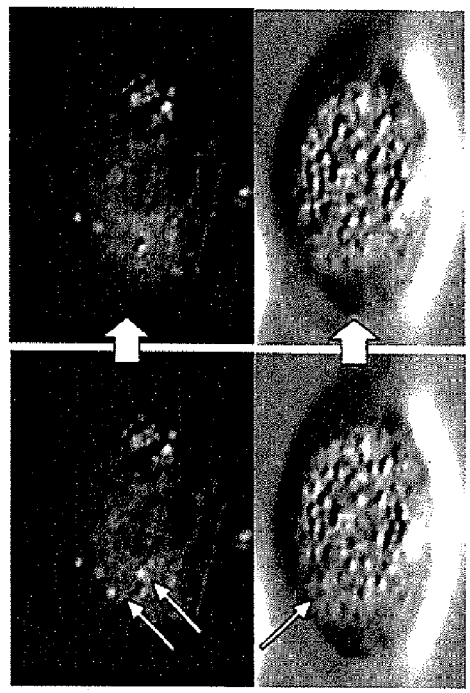
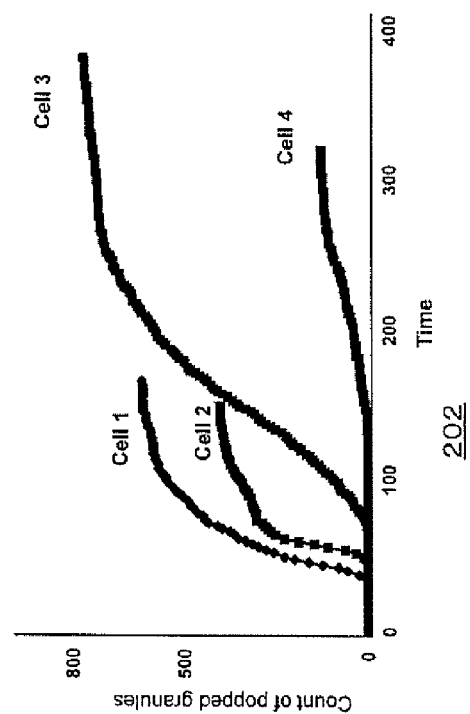
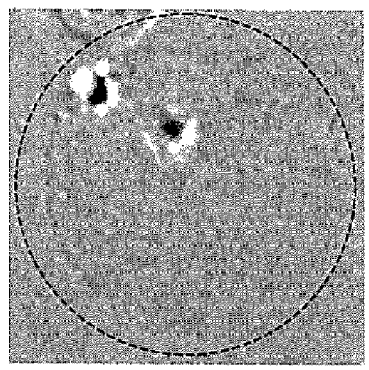

FIG.7

| Peak Name (24) | m/z (25) | t-value A − B (26) |
|---|---|---|
| 162.09 | 162.092 | 99.970 |
| 112.08 | 112.082 | 99.824 |
| 138.1 | 138.089 | 99.811 |
| 148.07 | 148.074 | 99.764 |
| 56.05 | 56.051 | 99.727 |
| 94.06 | 94.063 | 99.703 |
| 164.08 | 164.078 | 99.640 |
| 192.11 | 192.107 | 99.569 |
| 179.11 | 179.113 | 99.538 |
| 134.07 | 134.069 | 99.527 |
| 109.07 | 109.074 | 99.523 |
| 187.09 | 187.09 | 99.492 |
| 126.09 | 126.093 | 99.471 |
| 113.12 | 113.115 | 99.442 |
| 190.09 | 190.089 | 99.374 |
| 153.11 | 153.108 | 99.371 |
| 111.08 | 111.084 | 99.330 |
| 80.05 | 80.052 | 99.222 |
| 98.07 | 98.066 | 99.117 |
| 206.12 | 206.124 | 99.116 |
| 77.04 | 77.04 | 99.112 |
| 137.08 | 137.082 | 98.987 |
| 97.07 | 97.072 | 98.922 |
| 68.05 | 68.049 | 98.835 |
| 163.05 | 163.053 | 98.789 |
| 159.1 | 159.104 | 98.777 |
| 108.05 | 108.046 | 98.744 |
| 176.07 | 176.074 | 98.694 |
| 96.05 | 96.054 | 98.498 |
| 212.09 | 212.005 | 98.306 |
| 122.06 | 122.061 | 98.291 |
| 59.06 | 59.057 | 98.162 |
| 218.1 | 218.104 | 98.122 |
| 154.1 | 154.102 | 97.967 |
| 206.74 | 206.742 | 97.964 |
| 55.77 | 55.774 | 97.954 |
| 141.04 | 141.036 | 97.914 |
| 124.08 | 124.076 | 97.903 |
| 189.09 | 189.094 | 97.765 |
| 217.11 | 217.113 | 97.684 |
| 139.1 | 139.098 | 97.630 |
| 82.03 | 82.033 | 97.613 |
| 95.06 | 95.06 | 97.577 |
| 186.03 | 186.031 | 97.346 |
| 125.09 | 125.085 | 97.250 |
| 207.03 | 207.031 | 96.966 |
| 226.04 | 226.041 | 96.770 |
| 111.92 | 111.925 | 96.742 |
| 261.1 | 261.098 | 96.628 |
| 231.17 | 231.17 | 96.542 |
| 107.03 | 107.031 | 96.511 |
| 173.02 | 173.02 | 96.469 |
| 73.05 | 73.053 | 96.335 |
| 150.09 | 150.094 | 96.317 |
| 92.05 | 92.05 | 95.574 |
| 110.07 | 110.067 | 95.422 |
| 81.04 | 81.042 | 95.297 |
| 481.14 | 481.139 | 95.203 |
| 202.92 | 202.923 | 95.023 |

FIG.14
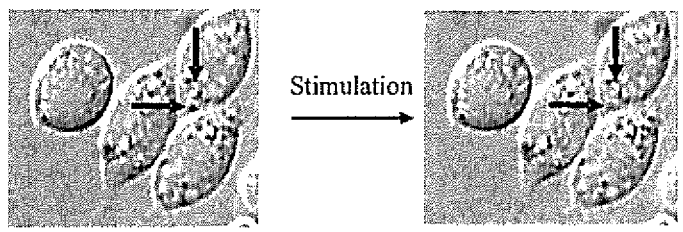
218
Medium MS spectrum (after stimulation)
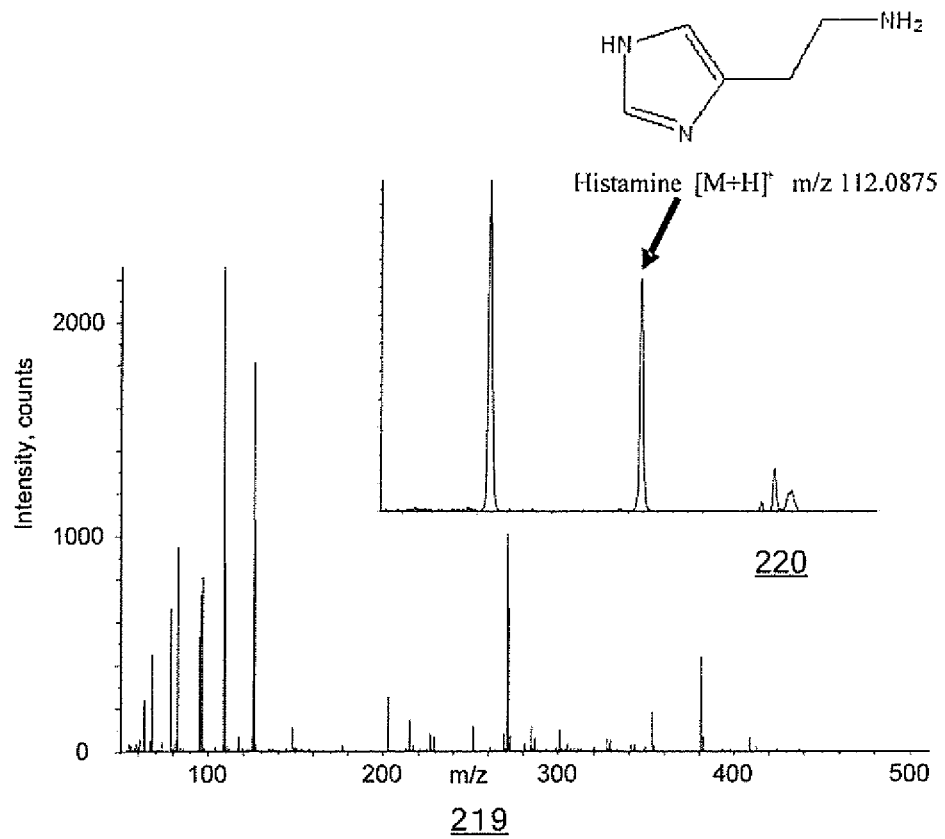
219

FIG.47

Peaks decreased after treatment

| m/z | Ret. Time | t-value | m/z | Ret. Time | t-value |
|---|---|---|---|---|---|
| 229.997 | 17.12 | 99.96374 | 122.952 | 17.01 | 97.09456 |
| 193.024 | 17.19 | 99.72366 | 126.048 | 17.81 | 96.27148 |
| 170.056 | 17.8 | 99.65694 | 208.009 | 17.42 | 96.12896 |
| 152.056 | 17.31 | 99.58516 | 152.132 | 25.24 | 95.71875 |
| 400.322 | 27.88 | 99.52396 | 394.878 | 16.99 | 95.52835 |
| 204.146 | 17.18 | 99.48277 | 310.923 | 16.63 | 95.50574 |
| 186.035 | 17.23 | 99.287 | 155.059 | 17.8 | 95.46187 |
| 192.038 | 17.37 | 99.23873 | 199.189 | 23.52 | 95.41301 |
| 176.083 | 27.92 | 98.93363 | 203.067 | 17.8 | 95.36978 |
| 162.048 | 17.71 | 98.75154 | 308.106 | 23.39 | 95.28754 |
| 330.085 | 17.76 | 98.60477 | 162.138 | 17.13 | 95.1096 |
| 160.067 | 27.74 | 98.3262 | | | |
| 214.016 | 17.35 | 98.06794 | | | |
| 184.087 | 20.51 | 98.05241 | | | |
| 258.918 | 16.99 | 97.98533 | | | |
| 462.855 | 16.99 | 97.93906 | | | |
| 297.984 | 17.14 | 97.56439 | | | |
| 308.105 | 17.66 | 97.39228 | | | |
| 233.081 | 17.66 | 97.33194 | | | |
| 202.117 | 20.13 | 97.26756 | | | |

110

Peaks increased

| m/z | Ret. Time | t-value |
|---|---|---|
| 293.158 | 17.38 | -99.9857 |
| 147.101 | 17.38 | -99.9033 |
| 163.059 | 24.79 | -99.8845 |
| 302.305 | 27.72 | -99.8133 |
| 169.08 | 17.31 | -99.7485 |
| 191.06 | 17.23 | -99.7323 |
| 175.135 | 17.35 | -99.6932 |
| 132.976 | 17.74 | -99.2653 |
| 664.419 | 33.96 | -99.0727 |
| 342.995 | 17.22 | -98.9791 |
| 477.253 | 31.16 | -98.8227 |
| 207.026 | 17.23 | -98.7932 |
| 327.018 | 17.23 | -98.5606 |
| 141.024 | 26.3 | -97.8284 |
| 349.169 | 27.16 | -96.8924 |
| 303.141 | 30.69 | -96.2269 |
| 746.128 | 32.34 | -95.5792 |
| 303.306 | 27.65 | -95.2434 |
| 209.139 | 27.45 | -95.0194 |
| 795.1 | 32.34 | -95.0126 |

111

FIG. 55
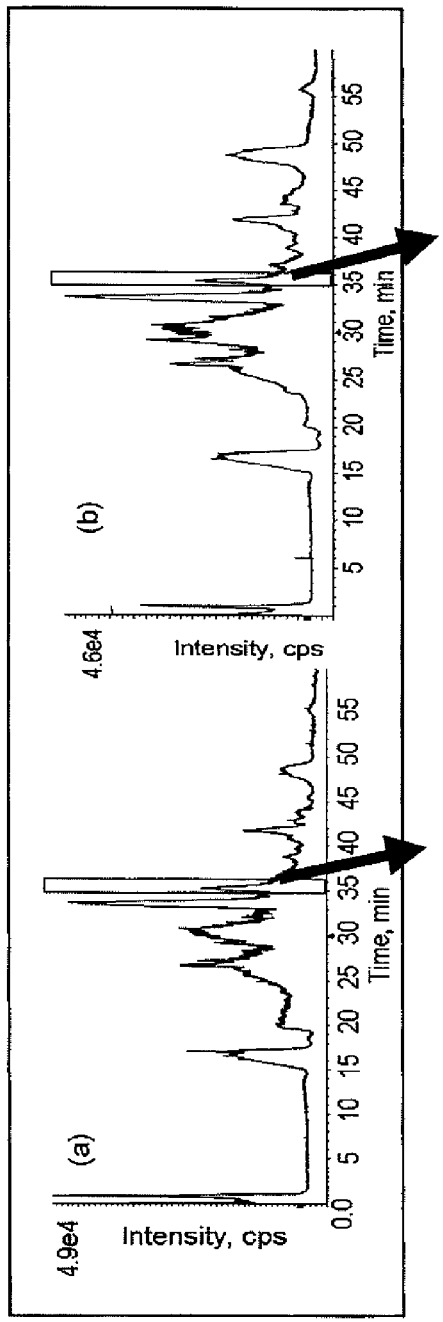
140
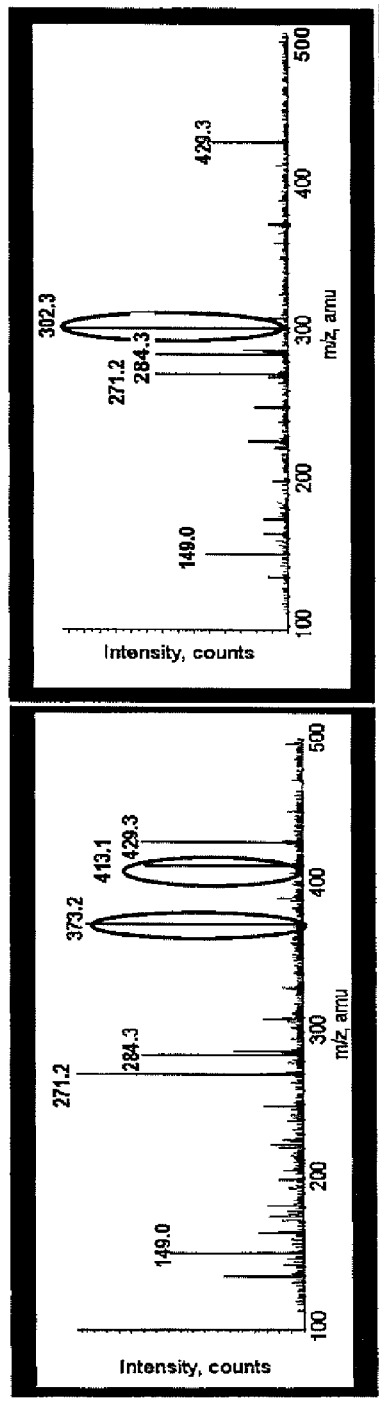
141

CAPTURING OF CELL FLUID AND ANALYSIS OF ITS COMPONENTS UNDER OBSERVATION OF CELLS AND INSTRUMENTS FOR THE CELL FLUID CAPTURING AND THE ANALYSIS

CROSS-REFERENCE TO RELATED APPLICATIONS

This application is a continuation in part of U.S. application Ser. No. 12/739,660, filed on Aug. 30, 2010, now abandoned, as the U.S. National Phase under 35 U.S.C. §371 of International Application PCT/JP2008/070060, filed Nov. 4, 2008, which claims priority to Japanese Patent Application No. 2007-286208, filed Nov. 2, 2007, and Japanese Patent Application No. 2008-095092, filed Apr. 1, 2008. All of these related applications are hereby incorporated by reference in their entirety.

FIELD OF THE INVENTION

This invention is relates to real-time capturing of cellular fluid and analyses of its components under the cell observation and instruments for the cell-fluid capturing and the analyses.

BACKGROUND OF THE INVENTION

Molecular mechanisms of cells are the essential of life phenomena, and they are eternal subjects to be clarified in life sciences. However, by present, there has been no analytical method to detect huge quantities of molecular groups and ions in living cells in real time or in time sequences with simultaneous direct observation of the cells, and then the methods identify and explore the key molecules to clarify the molecular mechanisms associated with observed phenomena, such as morphology. If new analytical methods and apparatuses which enable such analyses are developed, we can find or clarify not only life phenomena but also disease state and can discover the marker molecules of disease states and candidate molecules which can be medicinal substances, in a greatly shorter time than before. These methods and apparatuses will bring great benefit to human being.

Until now, in such analyses, the obtained results are generally based on just average data of many cells and then we discover new molecules in living system and speculate molecular mechanisms. The cells are put in the set conditions, collected before and after condition setting with such as an external factor of stimulation etc., and then are homogenized and are put to various molecular analyses, for example, electrophoresis which requires time and care, molecular detection using biological affinity like immune phenomena, detection methods by labeled substances and so on, because of low analytical sensitivity. However, we have been learned by cell observations with video microscope for a long time that responses of cells are not the same but independent each other under the same conditions.

FIG. 1, photo (200) shows that the time course of the counted numbers of popped granules out of each rat mast cell under the stimulation by calcium ionophore. Photo (201) is the one of example captured images of popped granules analyzed by a subtraction video imaging method of microscope images of the said cells. The right figure shows time course of the count of popped granules of each cell in the microscopic observation field as a result. These cells were cultured in the same culture dish and thus in the same culture condition. This shows that one cell pops many granules at once, and other cells don't pop granules easily, although the cells are in the same condition and given the same circumstance. We should say that each cell has its individuality. This truth was finally found by our observations and by analysis of the records of images of cells under video microscopes.

As shown above, cells show many variations in their response and dynamism, and show many differences between cells under careful observation of the cellular behaviors. It may be caused that cells which look same, have some differences in their components, or have difference of maturation level in each cell, or have difference of cell-cycle stage of cells, or have differences of microenvironment in micro region of cells and so on. If it is the case, the conclusions from results drawn by science by averaged data, should be reconsidered. In order to clarify the dynamics of intracellular molecules and molecular mechanism of cells, it is ideal that molecules in a single (individual) cell and the secreted molecules from the single cell should be analyzed together with simultaneous observation of the behavior of the single cell. We think such analysis is necessary to investigate the molecular mechanisms of life. It can be said to be important in any phenomena in micro region, especially, the organized and well designed behaviors of the cells are important, because cells are the accomplished system through the evolution for billions of years. The clarified results will have a great influence on human being and the results can widely contribute to human health and medical care. It can be said that the development of analytical methods to analyze molecular dynamics of a single cell in association with the real time observation of cells will introduce a paradigm shift in analytical methods of the world's life science and accelerate the analysis speed in dramatic way. It should be the dream of life science which everyone has ever thought.

On the other hand, according with the development of recent nanotechnology, it is now necessary to capture the molecular changes with actual observed changes in micro region together with observation of material change at micron or sub-micron areas. It has been hoped and thought to be useful to establish the analysis of molecular changes in all micro region of existences not only for nano-technologies, but also for such as chemistry and material chemistry and so on. In this application, it is essential that "cells" can be converted to be the "micro space" under observation. We used "the cell" as the typical example of "the sample of micro space" to explain this invention, because the cell is the most complicated and organized as living system with a lot of veiled aspects.

The range of application fields of this invention is wide. Generally speaking, all samples which are composed of liquid as base components are the subjects to be applied by this invention. This invention is distinguished in supplying more rapid and direct methods than conventional methods and this invention is characterized as capturing molecular groups from micro region space directly together with visualizing the changes in micro region space, and detecting the molecules and atoms directly or in situ, by high sensitive molecular and atomic detecting methods such as mass spectrometry and inductively-coupled plasma (ICP) mass spectrometry, and exploring the changes of the molecules and atoms, and considering the mechanisms at ionic and molecular level, which had not been achieved (in sensitivity, speed and directness) in the world until now.

We can find the case which had ever analyzed cell contents by using mass spectrometry in the analyses of protein components in populated cells (Ref. 1).

Another example is the system which extracts multiple molecules in bio-fluid by multiple affinity micro-columns specifically and then analyzing them by mass spectrometer (Ref. 2).

Reference 1: Unexamined patent publication No. JP2002-537561A

Reference 2: Unexamined patent publication No. JP2005-503537A

DISCLOSURE OF THE INVENTION

Subjects to be Achieved by this Invention

The subjects to be achieved by this invention are real time, high sensitive, rapid, direct and highly-reliable method to capture the contents at single cellular level and even in sub-cellular organelle level which enables molecular analyses and its quantitative determination together with observing the behaviors of single cell including its individuality. Until now, the methods to analyze intracellular molecular mechanisms had been almost achieved only by using populated system of multiple cells, although the responses of cells are not the same. Moreover, this invention provides the analytical methods of capturing the components in each cell directly even from the inter-space of cells or between different cells which are, for example, located in cancer tissues in a normal tissue, enabling us to detect the molecular and atomic composition with morphological microscopic information.

This invention also provide an analytical method to support the molecular mechanism analysis at molecular and atomic level by evaluating the increase or disappear and/or manifest of molecules between diseases and normal, or between abnormal and normal, and between treated by physical or chemical or biological or not treated.

Since cells are alive, their morphological behaviors are mostly related with the cell dynamism. Therefore, it is preferable that the above mentioned analytical methods should be performed with simultaneous morphological observations of cells to clarify the mechanisms of life by ions and molecules of life phenomena.

It is also necessary to provide the methods to examine the relation between the external factors and cellular molecular changes for clarification of mechanisms of expression of cell function, since cultured cell lines and cells in living tissue are responding to various external factors. The task of this invention is to provide the methods enabling molecular kinetic analyses and molecular exploring analyses simultaneously with behavior analyses, and clarifying the molecular mechanisms rapidly and directly for each individual cell. Since it is necessary to capture the molecular changes with observed actual conditions or changes of materials in micro region of 200 micrometers or less by recent development of nanotechnology, another mission of this invention is to provide the methods of visualizing the changes in micro region and clarifying molecular mechanisms in it.

Now, comprehensive gene analyses are now progressing about various disorders and many genes associated with disorders and proteins which are expression products of genes have been clarifying, however only these gene and protein level analyses are not enough for concrete and enough measures against the causes of disorders. By enabling the analyses of low molecular dynamism in cells associated with the disorders, we can get entire picture of life phenomena, likely in human society, genes as command center, RNAs and proteins as executive office and low molecular groups as workers in various fields like sales department, and we can clarify the causes of disorders deeply and lucidly.

It is very important to explore cell differentiation factors for regenerative medicines such as induced pluripotent stem (iPS) cells. The comprehensive analytical methods of inducing factors which are mostly low molecules, had been performed only by populated systems of multiple cells until now. However, we know by microscope observations that all cells don't differentiate and a part of cells in cell populations will differentiate. This invention will provide the first methods to analyze only the morphologically differentiated cells selectively while the degree of differentiation is visually observed in its morphology.

Analyses and studies at gene level has been extended in the food research fields of alcoholic beverages such as wine, "sake", beer, whiskey and "shouchu", and in the fermented food such as soy sauce and "miso", and processed food such as Japanese pickles, "kimchi" and pickles, and dairy food such as yogurt and cheese. It is hoped that the analytical methods of low molecular dynamics which are related to fermentation of yeast and lactobacillus in microbial cells appear and their integration of the results by analyses of genes and proteins levels, because there is a limit in the studies based on only analyses of their genes and proteins to study the subtle quality such as flavor and fragrance. As above stated, in fermented food industry, we hope not only the microbe studies but also the analytical methods of low molecular dynamics with microscale sampling of culture fluid for subtle quality control of flavor and fragrance at the fermentation processes.

In the plant studies, there are generally many yet-to-be-decapillaryd phenomena in the various study fields such as plant physiology and embryology compared with animal cells. The study of low molecular dynamics is hoped to clarify molecular mechanisms which are responsible for differentiation, forms, colors and fragrances of plants. Since the demands for genetically-modified crops are increasing due to food production needs and etc. in these years, the establishment of the methods to trace the changes of small molecular dynamics from or to cells is hoped. It is important problem not only ecological risk assessment but also safety assessment of genetic modification.

In general chemical product industries, especially in such as organic semiconductor, organic conductor, and organic optical material industries, high purity is concerned in these product line, and in food product lines, quality assurances for health are important for such as food additives. Since small amount of factors affect to physical and chemical performance of material products and to quality for health assurance of food products, rapid analyses of molecular dynamics in micro-regions, such as monitoring and control of small amount of factors, are preferred.

However, it is important to be able to detect ultralow amount of substances which are included in single cell or in single sub-cellular organelle at first for resolving the above mentioned problem. Current detection sensitivity of mass spectrometer, by hybrid quadrupole time-of-flight mass spectrometer (so-called Q-TOF) and fourier transform mass spectrometer (so-called FT-MS) which are used commonly for molecular explorations, are up to about 1 micro mole/liter (1 micro M) at the detection limit, and the volume of single cell is about 1 pico-liter (1 pl) in case of 10 micro meter diameter of a sphere cell. So, we can detect molecules if there are about 1 million numbers of molecules in each cell. Until now, there are examples of molecular detection of a single cell by matrix assisted laser desorption/ionization (MALDI) in the analyses, however, only the easily-ionized molecular peaks were detected and the number of detected peaks was so less than that of molecules which should be contained in the cell. So we found we cannot perform comprehensive molecular detection by MALDI ionization method.

Although MS/MS like analyses is possible recently because the analyzers of TOF-TOF and ion trap-TOF have become available, MALDI-TOF lacks in the power of molecular identification and in quantitative performance. In addition, it can not be identified where the cell exists in the process of crystallization of matrix which is added to single cells for ionization. Thus, it is not easy to shoot the position of the cell by laser in micron scale using the video imaging after setting of the sample plate in the mass spectrometer. Even if we try to analyze the cell at the exact moment under observation, the cell state has been changed rapidly during operations of trapping the cell and putting it on the MALDI sample plate. No one knows what is going on after the addition of matrix which is almost saturating solution of organic molecules at last and how the contained cellular components have been changed since they were alive.

It is necessary to use the mass spectrometers above mentioned to perform MS/MS analysis for molecular identification, and for this MS/MS analysis, molecular ionization should be continued to introduce many ionized molecules into the spectrometer and to select molecular species stepwise and in sequence for MS/MS analyses, in which molecules are fragmented one by one (introduce into the collision cell) and we get the fragment spectra as MS/MS analyses. However, enough time to ionize the samples cannot be secured if conventional electro-spray ionization is employed because the single cell volume is so tiny amount of only 1 pl and the sample is sprayed at once even though a few minutes continuation of ionization is needed (for step wise analysis).

The Means to Solve the Problem

To solve the above mentioned problems, this invention has the following constituents. According to the one of characteristic features of this invention, this invention gives the method of capturing the cellular components which are composed of cells or are secreted from the cells under observation of cell dynamism and then mass spectrometry is performed in real time.

This invention then includes following steps; The step of inserting the nanospray ionization capillary tip whose top bore has the diameter corresponding to the specific region of the cell under observation of its dynamism with the microscope;

the capturing step of cellular components of a specific region of the cell into the top of a nanospray ionization capillary tip and keeping the components at the top point;

the step of introducing the ionization supporting solvent from the back-end of the nanospray ionization capillary tip;

the step of ionizing the cellular components using nanospray ionization by applying the electric field between the sample inlet of the mass spectrometer and the nanospray ionization capillary tip, and introducing the components into the mass spectrometer as the sample;

and the step of performing mass spectrometry for the introduced cellular components as the sample by a mass spectrometer.

According to another feature of this invention, this is the system of capturing the cellular components which are composed of cells or are secreted from the cells under observation of cell dynamism and then mass spectrometry is performed in real time.

The system is thus equipped with as follows;

Microscope(s) for observing the dynamics of the cells which contains the target cellular components to be analyzed by mass spectrometry;

the ionization nanospray capillary tip(s) whose top bore is smaller than the size of the cell in diameter to take the cellular components of the cell and the tip which has a open-end in back side to introduce the ionization supporting solvent, which can ionize the target cellular components for mass spectrometry;

mass spectrometer(s) which performs mass spectrometry for the ionized cellular components which are introduced to the inlet of the spectrometer as the sample;

and the power supplying part for applying the electric field between the sample inlet of the mass spectrometer and the nanospray ionization capillary tip.

In this system, top of the tip is inserted into the cell under observation with microscope(s), then the cellular components in a specific region of the cell are captured from top bore of the tip, and then ionization supporting solvent is introduced from back-end of the tip to ionize the cellular components by applying the electric field between the sample inlet of the mass spectrometer and the nanospray ionization capillary tip. The cellular components of a sample are introduced into the mass spectrometer by nanospray ionization.

The preferred embodiments of the above-mentioned method and system of this invention will be described as follows: As a structure of the nanospray ionization capillary tip, the diameter of the top bore of the nanospray ionization capillary tip is from 0.1 to 100 micrometer. The inside of the top bore of the nanospray ionization capillary tip has the structure with some molecular affinity to capture the molecules. At least either the inner or outer surface of the nanospray ionization capillary tip is conductive to be the nanospray ionization capillary as the electrode for applying the electric field. Otherwise, the nanospray ionization capillary tip equips the conductive thin wire stretching from back-end of the nanospray ionization capillary tip to the top bore of the nanospray ionization capillary tip to make conductive thin wire acts as the electrode while applying the electric field. The outer surface of the nanospray ionization capillary tip is hydrophobic when the objects of the analysis are the cells with cell membrane as septum which have lipid solubility inside. The outer surface of the nanospray ionization capillary tip is hydrophilic when the objects of the analysis are the cells which have cell membranes or cell walls as septum which are formed by hydrophilic substances.

Other preferred embodiments of this invention on capturing the cellular components are as follows:

When the top bore of the nanospray ionization capillary tip is approaching to the observed cell, the void gas in the nanospray ionization capillary tip is pressurized from outside to prevent the surrounding components, such as cell culture fluid, being contaminated into the top bore. When the top bore of the nanospray ionization capillary tip has reached to the observed cell, the pressurization is relieved, then the target cellular components for mass spectrometry are sucked into the top bore of the nanospray ionization capillary tip. The target cellular components for mass spectrometry are captured from the top bore by making cells or tissues leak from the formed hole(s) on its liquid container of organizations.

Other preferred embodiments of this invention are on the ionization supporting solvent which is mixed solvents which contain volatile acids or bases. After the introduction of the ionization supporting solvent into the tip, the added ionization supporting solvent is filled to the top point of the tip by using at least one of vibration or centrifugal force or pressure to the nanospray ionization capillary tip.

Other preferred embodiments of this invention are on the method and system with manipulator(s) which controls the three-dimensional positioning of the top bore point of the nanospray ionization capillary tip. It is achieved by using the manipulator which is set between the observing cell and the before-mentioned mass spectrometer. The back-end of the nanospray ionization capillary tip is connected with the top point of the manipulator. When the cell components are captured, the manipulator leads the top bore of the tip to the collection position of the cell which is the object of the mass spectrometry. When the cell components should be introduced into the mass spectrometer, the manipulator leads the top bore of the tip to the sample inlet of the mass spectrometer.

Other preferred embodiment of this invention is for evaluation and identification of temporal-spatial molecular difference in the observed cell(s) under microscope. Cell contents are captured from the top bore of the before-mentioned tip, from the spatially different positions of cell(s), or from cell(s) at temporally different timings, or from cells before and after some treatment of cell(s) under the various different treatments. Mass spectrometry gives each mass spectrum at above-mentioned conditions of space, time, and prior or after treatments. (The difference in the spectra shows the dynamics of molecular mechanism in cell(s).)

Other preferred embodiment of this invention is for the molecular identification. The mass spectrometer is set to store the data of mass spectra of known samples in prior to the measurement of introduced new sample and the new sample's spectrum is undertaken while the nanospray ionization is continued. Then the differential mass spectrum between reference (known and pre-stored) spectrum and the new sample is subtracted to extract specific molecular peaks, and this peaks are selected by mass filter to put higher order mass spec. analysis (like MS/MS analysis) for molecular identifications.

According to another feature of this invention, it is the (same) nanospray ionization capillary tip which not only captures cellular components but also perform nanospray ionization of cellular components for mass spectrometry, and it equips as follows:
The top bore is smaller than the specific (target) region of the cell in diameter, and the back-end of the tip is open to introduce the ionization supporting solvent, and with filament which has solvent affinity surface, attached to the inner surface of the tip extending to the top point for solvent leading to the top of the nanospray ionization capillary tip, and with hydrophobic outer surface of the nanospray ionization capillary tip. The filament can be made of an electro-conductive material, or a nonelectro-conductive material, such as glass.
Furthermore, the nanospray ionization capillary tip which has the top area whose surface is conductive at least either inside or outside, or the tip in which the conductive thin wire is inserted to stretch from the back-end to the introduced ionization supporting solvent, and by either way, electric field can be applied between the tip and the mass spectrometry.

Effects of Invention

We can have the age when organic and inorganic molecules in a cell can be analyzed rapidly and directly by trapping at least single cell level, and by trapping at least single cell's interia and exteria or even at single organelle's components in bio-tissues, while it has been performed by sciences using only averaged-value, in which we have collected mostly the aggregated cells or many cells, and collected the cell components after pretreatment of homogenization etc. and then analyzed the molecules. By this invention, the molecular mechanisms of cells can be clarified from the perspectives of both morphological changes and molecular changes by real-time microscopic observation of cells and molecular detections, because the cells respond to the external factors to behave purposely and their behaviors mostly relate to intracellular molecular dynamics. In cell behavior observation, we can discover unknown molecules as well as new functions of known molecules in relation to changes of labeled known molecules and can trace new molecular function, using conventional labels for known molecules such as isotope-labeling or fluorescently-labeling. There are large varieties and number of molecules in cells and tissues, and the molecules are responding to various external factors and are keeping changes. Many active key molecules which are minor, are often hidden to be detected by other major coexisting molecules. However, by applying statistical methods, such as t-test and multivariate analysis, to the molecular peaks of detected mass spectra or by subtracting the spectra between two stages, the molecules which are changed or which are specific to certain stage, can be evaluated and explored by between before and after the cellular changes, such as before and after response to the external factors, or between the stages in which the cells are set. This invention enables any analyses of each individual cell in combination with morphological behavior, molecular dynamics, and molecular exploration, simultaneously, and provides the method to clarify the molecular mechanisms of life more rapidly and directly than before.

Furthermore, this invention enables high sensitive, rapid, direct and highly-reliable analyses without putting stress on each cell during the analysis of molecular dynamics and cell behaviors at the same time. The damage on the cell and the influence on inserting the capillary tip into the cell to the cellular response, and the leakage of components along with the insertion, are minimized, because the capillary tip for capturing cellular component by inserting into micro-bodies, e.g. cells, especially the outer surface of the top bore, is coated to be hydrophobic or hydrophilic to improve the affinity (of the outer surface of the capillary tip) to septum components such as cell membranes, then the capillary tip can be inserted very smoothly to cell membrane etc., without distortion and leakage of components. By modification of binding molecular affinity groups to the inner surface of the top bore of the capillary tip or by setting resins whose physical properties of surface are varied on purpose, removal of salts which suppresses the molecular ionizations for mass spectrometry, and selective enrichment and efficient capturing and eluting of the molecules and ions are performed. Furthermore, during the approach of the capillary tip to the cell, the coating of outer surface of the tip to be hydrophobic enables minimal contamination of culturing components into the tip by repulsion of water, and regulation of pressure of air in the capillary tip (for prevention of contamination) is simplified.

It is extremely difficult to lead the top bore of the capillary tip to the target cell position of about 10 micrometers under the microscope. The capturing operation is made to be quick by using electric manipulators. The position of the top bore of the capillary tip which is slightly different every time (however, it is pretty serious and big difference in microworld) is confirmed out of the microscope field, and then the top bore point of the capillary tip is led near the position of the cell which is determined by the focused point of the target cell at the center of microscope view field.

As a result, this invention enables us to perform comprehensive molecular analyses of each individual cell with high reliability and high efficiency. This method and system provide us any combination of morphological behavior analyses, molecular kinetic analyses and molecular exploring analyses simultaneously and we can clarify the molecular mechanisms of life phenomena rapidly and directly for each cell. Until now, the analyses of molecular components of cells have been performed by collecting many cells followed by pretreatment like homogenization. The current conventional analyses are tedious and require time. The obtained results are also of average data of many cells and have not reflected the temporal and spatial specificity. By this invention, the analyses with high temporal and spatial specificities even in such as sub-cellular organelles and with temporal morphological change are possible. In case that target is inhomogeneous aggregation of cells, such as cancer tissues, this method can directly capture single cells in different stages, and analyze molecular contents for comparison. The key molecules of diseases will be extracted in real time speed along with its molecular dynamism.

The molecules can be extracted by t-test, regression analyses, principal component analyses and clustering analyses of detected spectra between pre- and after stages when the cell(s) shows response to such as external factors. The extracted molecular peaks are selected in real time of measurement with short nanospray time for tiny amount of samples, and we make the selected molecules fragment in the collision cell and determine its molecular structures by MS/MS analyses. It makes speed up in clarifications of molecular mechanisms of life and in discoveries of new molecules including candidate molecules of medicinal substances by high-resolution mass spectrometry.

For example, the kinetic analyses of molecules changing between the cell states, the rapid explorations of cell differentiation factors in such as regenerative medicine, the discovery of the factors controlling cell differentiations and cell growth and controlling methods of them, molecular diagnostics and molecular explorations of cancer cell specificity, the identifications of cell species, the clinical tests by using tiny amount of oozing blood when the skin is pricked with a needle lightly (including such as oozing fluid from the living tissue such as skin), the personalized medicines which become possible by examining the individual drug metabolisms with single cell of the liver, the explorations the internal components by pricking the plants lightly and the clarifications of the molecular mechanisms of more natural actions of medicine by coordinated actions of multi-components in Chinese medicine formulations (Until now, a medicine has been designed with single compound.) will be enabled.

In addition, the dynamics of low molecules in cells is clarified associated with many genes and proteins (the expression products of genes) which have been studied comprehensively for various disorders. In the food and drink fields, the method of analyzing the low molecular dynamics in cells in relation to subtle quality such as flavor and fragrance is provided.

In plant studies, there are generally many yet-to-be-found phenomena compared with animal cells. This invention is applied to the researches of contribution of low molecules to differentiation, shape, color and fragrance of plants. In safety assessment, the low molecular dynamics in cells of genetically modified plants can be explored for current food supply problems.

In general chemical product industries, especially in such as organic semiconductor, organic conductor, and organic optical material industries, high purity is concerned in these product line, and in food product lines, quality assurances for health are important for such as food additives. Since small amount of factors affect to physical and chemical performance of material products and to quality for health assurance of food products, rapid analyses of molecular dynamics in micro-regions, such as monitoring and control of small amount of factors, are possible to be performed.

THE BEST EXAMPLES IN APPLICATION OF THIS INVENTION

The size of single cell ranges from 0.1 micrometer in diameter in the small one to enough visible large one such as eggs. Capturing of cell contents of nerve cells and eggs are easy which have large intracellular volumes and contain a lot of various components. Thus the principal target for solution of problems is the usual cell size about 10 micrometers in diameter from which it is difficult to capture the intracellular components. Then the analytical method can universal to almost all cases, if we care the case of 10 micrometers one.

However, the intracellular volume is less than 1 pico-liter and the volume of sub-cellular organelle is less thank ⅟10 of it. Thus, the detection limit of current mass spectrometer is around 1 million numbers of molecules in each, contained in a single cell. It has been very difficult in targeting it from the aspect of current sensitivity. The manipulation in such micro space and ionizations, detections and analyses of the ultratrace amount of molecules out of ultralow volume of the sample are the big problems.

Real-time performance is also important. It should be possible to capture the cell contents of the specific position of a single cell at the detected moment when the cell showed some change.

FIG. 2 shows one embodiment of nanoelectrospray ionization device used in the detection the intracellular molecules by mass spectrometry in this invention. The nanospray ionization capillary tip 1 is the capillary tip which is made by extending of insulator (mostly glass or plastic) capillary or metal capillary without heat or with heat, and whose preferred diameter of top bore is capillary with 0.1 micrometer to 100 micrometers diameter inside. The outer surface of this capillary tip is coated with metal 6 (such as gold and nickel) by sputter method or evaporation method. The sample solution is set in this capillary tip, and then the ionization supporting solvent (In positive mode, formic acid or acetic acid is usually used and sometimes volatile salts such as ammonium acetate and ammonium formate are used. In negative mode, ammonia etc. are used. The mixed solvents with acetonitrile or alcohol are also used. When the targets are peptides, proteins and nucleic acids, the mixed solvent, organic solvent with higher water content is also used.) is added, and then the sample solution is filled into the top bore of the capillary tip by centrifugal force or pressure on the top bore of 1.

After this operation, the top bore of 1 is arranged coaxially to the inlet of the mass spectrometer 2 away from several millimeters to several centimeters from the inlet. When the high-voltage direct current electric field optimally from several hundred volts to several kilovolts is applied 4 between the part which is conductively coated of 1 and the inlet of the mass spectrometer 2, then extremely capillary electrically-charged particles of liquid are emitted like a capillary spray. It is called nanospray 5. In the conventional electrospray method, the sample fluid is nebulized by applied strong gas stream to the terminal of the capillary tip and the high-voltage electric field is applied, and then the sample is ionized. However, only the part of sprayed small size mist in peripheral zone of the spray is introduced into the mass spectrometer because the misty droplets formed in central area are too large to introduce into the mass spectrometer. It seems to throw away most of the sample and the component of a single cell which is ultralow volume could not be introduced into mass spectrometer and components had not been detected.

We found the high efficiency of ionization of nanospray which is produced by only electric field (with no nebulizing gas). This seems to make very fine charged droplet of mist with flow rate from nano-liter to tens of nano-liter per minute. Thus we set nanospray tip coaxially and straight to the inlet of mass spectrometer with distance between them from several millimeters to several centimeters to make most of the sprayed sample be introduced into the mass spectrometer directly. The top bore of the nanospray ionization capillary tip is fabricated to be several micrometers in diameter and it is the most appropriate size to suck out the cytoplasm of a single cell into the top bore point.

It is very important components of this invention to suck cellular component directly by this "nanospray ionization capillary tip" and then "directly introduce the trapped sample" into measuring equipment (with addition of ionization solvent) with high efficiency, keeping the component at the top bore without dissipation of the sample to another container.

Such nanospray ionization capillary tip 1 works even if only inner surface of the capillary tip is conductively coated, or if both the inner and outer surface of the capillary tip are conductively coated, or if the whole capillary tip is formed of conductive material such as metal, or if the electrode is inserted in the sample solution in the capillary tip and the electric field is applied in the case of the capillary tip whose material has no conductivity. We found that the nanospray ionization capillary tip 1 can suck up to 1 nanoliter level solution from a cell and introduction of ionization solvent which should be preferred to be introduced from the back-end, made stable nanospray by keeping super tiny amount of cell components in the top of the tip (There are the components of this invention about stabilization as described below. See FIG. 29 and FIG. 30).

The tip 1 is used for suction of whole cell or intracellular fluid (or when needed, extracellular fluid, of course) directly, and for keeping the cell fluid in the top bore of the tip, and then above-mentioned ionization supporting solvent is added from the back-end, opposite side of the top bore, of the capillary tip. We have established at the first time in the world that the cell contents and its solution is easily ionized and introduced into mass spectrometry. By this establishment, so tiny amount of molecules and ions in a super micro volume, which have not be detected by current sensitivity of mass spectrometer, are captured by sucking the samples and the molecules are detected by this invented method with very simple procedure under the direct observation when cell shows some change. Furthermore, site-specific detection such as intracellular organelle is also possible. This method enables high speed analyses of molecular exploration and identification and thus the clarification of molecular mechanisms.

Figure 3:
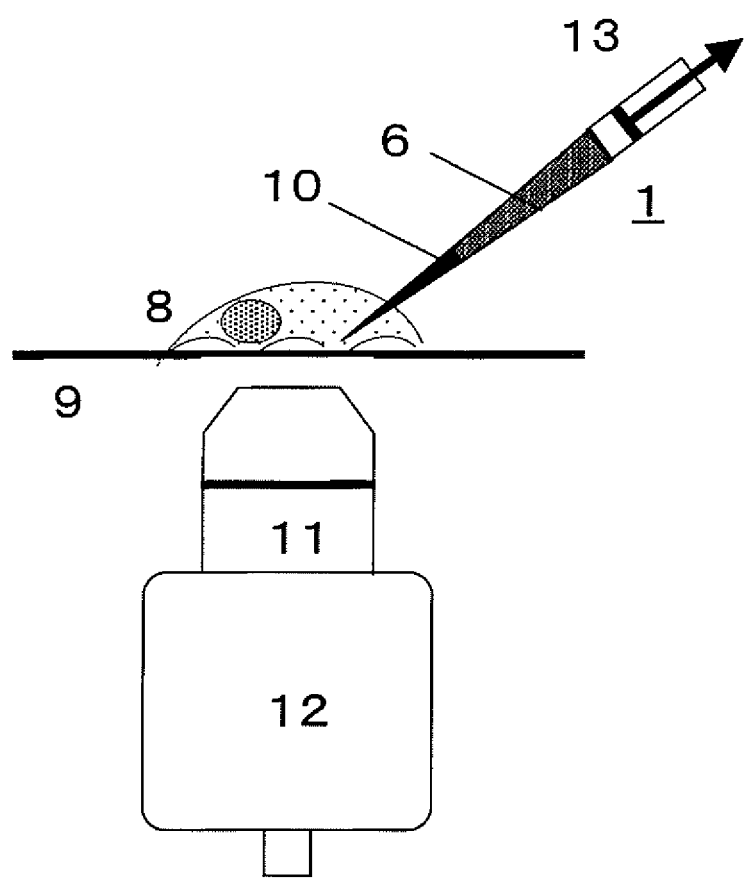

FIG. 3 shows schematically the inserting moment of the nanospray ionization capillary tip 1 to the cell 8 cultured in the Petri dish on the microscope stage. The cell 8 is observed with the combination of the objective lens 11 and appropriate illumination optics (the description is not shown) simultaneously. The video camera 12 is set by adjusting the position of the image sensor such as CCD to the focal plane of the objective lens. By this setup, it is possible to monitor cells not only by the eyes but also as enlarged video images, and to record the cellular behaviors. Image analysis of dynamic changes of the objects of cells shows the differences and the changes of position and area, and molecular localization, transport and change in amount by probing fluorescent proves. We can suck out the internal fluid or organelle of the cell 8 or the local component in the observing micro region by the sucking operation 13 at any timing such as the moment of the cellular changes. The cellular fluid can be captured at the top bore of the capillary tip 1 directly and introduced into the mass spectrometry by nanospray ionization almost in real time.

Figure 4:
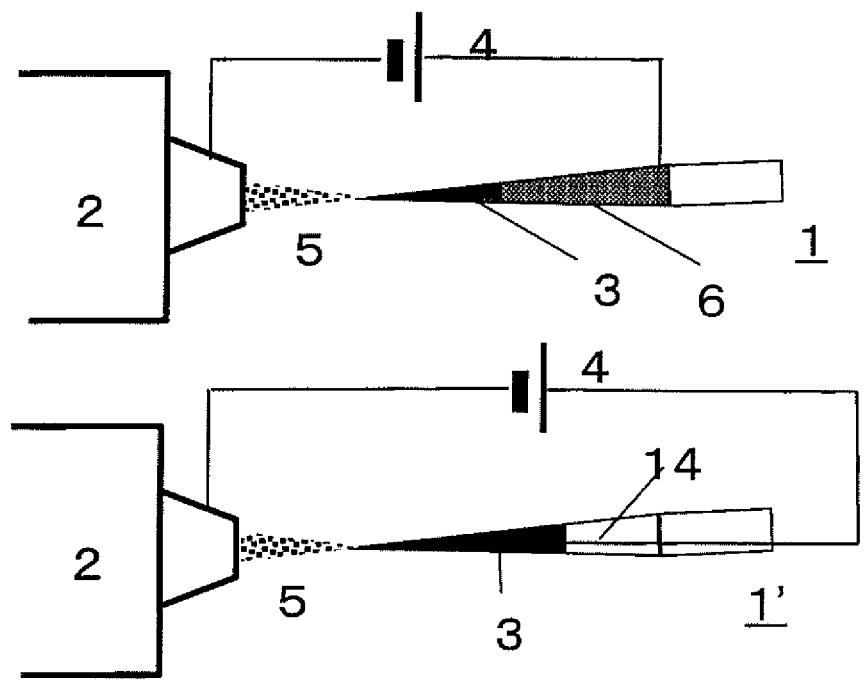

The top figure of FIG. 4 shows the embodiment of the invention of the nanoelectrospray ionization device used for the detection of cellular molecules by mass spectrometry as FIG. 1. The outer surface of this nanospray ionization capillary tip 1 is coated by metal 6. However, as shown in lower side of the figure, the capillary tip 1' which has not metal-coated surface 6 with tapered top bore can produce nanospray by inserting the electrode 14 and by applying high-voltage from several hundred volts to several kilovolts 4 to the sample fluid directly.

The capillary without taper such as the capillary tube often used for gas chromatograph is also acceptable. The sucked components by the capillary are transported to the separation medium (for example, monolith column) directly and can be introduced into the mass spectrometry by nanospray ionization method from the capillary end by elution after separation (See FIG. 45).

At this ionization method, it is possible to produce photo-excitation ionization for the molecules with lower polarity by irradiating of high-intensity light such as ultraviolet laser light or xenon lamp or deuterium lamp to the spray region.

Furthermore, it is also possible to produce corona discharge for chemical ionization method under atmospheric pressure by applying high-voltage between the nanospray ionization capillary tip and discharge terminal alternately without greatly disturbing the gradient plane of electric field for the nanospray.

Since, the nanoelectrospray ionization method which has wide range of applications and is simple in operation, only this method is described as a typical example of ionization below.

Figure 5:
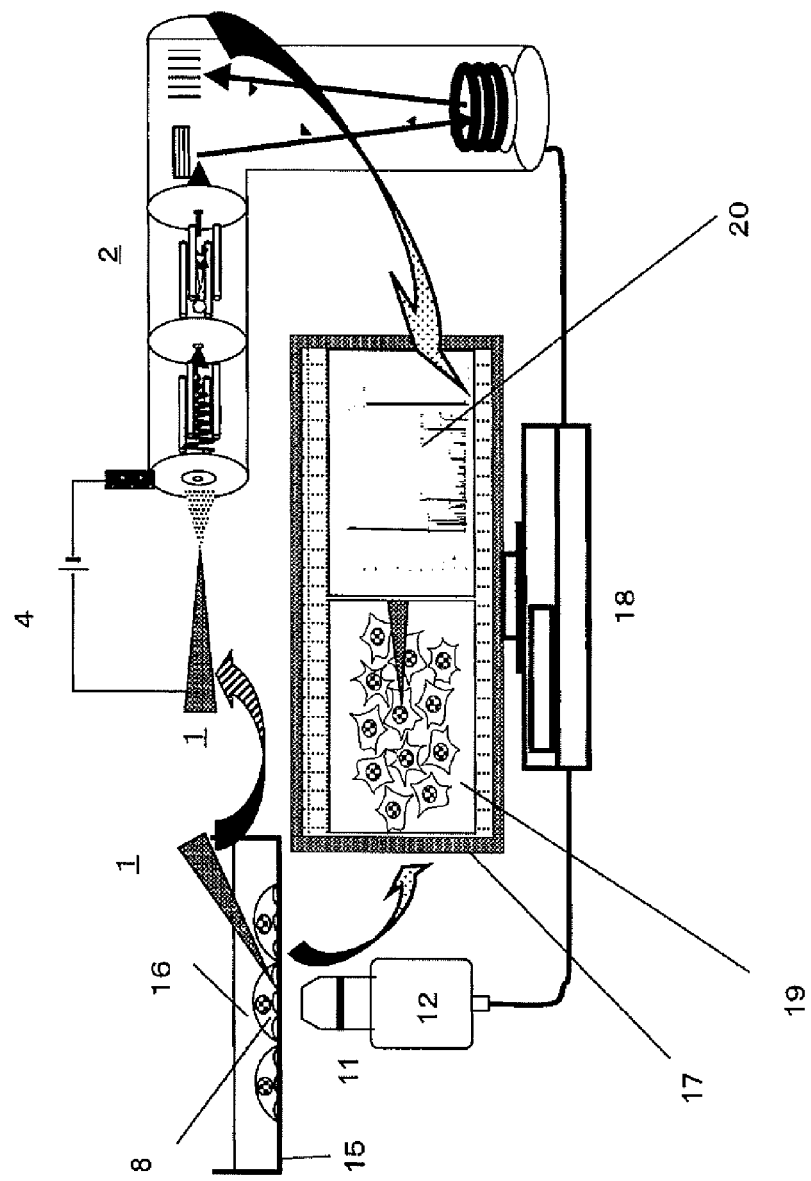

FIG. 5 shows one embodiment of the integrated system formed for this invention. The cells 8 which are cultured by cell culture fluid 16 in the left Petri dish 15 are observed by the video microscope 11, 12 and enlarged for observation. The dynamics of the cells are recorded or performed image analyses simultaneously and the changes are captured. The images is sent to the left screen 19 of the monitor 17. The signals from the video camera are sent to the video board in the computer 18, and recorded and stored for image analyses. The cellular fluid which is captured by inserting the said nanospray ionization capillary tip (It is called "ionization capillary" below.) 1 or 1' to the target cell 8 and sucked directly. After adding the ionization supporting solvent, the tip is set directly to the nanospray ion source of the mass spectrometer manually or automatically. Then it was found that by applying the high-voltage between the tip and the sample spray inlet of the mass spectrometer 2, the nanospray was produced and then a lot of molecules existing in the captured cellular fluid were found to be detected by mass spectrometry (such as ion trap, tandem quadrupole, Q-TOF, ion trap-TOF, FT-MS, or their combinations). The mass spectrum 20 is also shown in the monitor simultaneously. The detection and exploration of the molecules in (or out of) cells at arbitrary timing of the moment is performed under observation of morphological changes or on purpose behaviors of living cells. This had not been possible before, but become possible in direct way by this invented system. Since the decrease of cellular fluid in a cell by the capture is minimum, effects is also minimum on the molecular dynamics. Thus, it is possible to continue capturing of intracellular fluid in a same cell and the molecules can be detected several times until the amount of intracellular fluid is decreased significantly. At least, the effect of the first operation on the cell dynamism should be in minimum.

There are large varieties and number of molecules in cells and in living tissues, and the molecules keep changing responding to the various external factors. The detection of many active molecules which are present in extremely small quantity but hold the keys, is often hard to be detected by other coexistent molecules. The method to discover what kind of molecules causing the cellular changes is necessary, when the cell is stimulated by substances added out side of the cells, when the circumstances are organized where the cells must respond to external factors such as stimulating factors of antigens added to the extracellular fluid, or when the cell is at the significant cell cycle when the cell will change significantly with time and so on.

By this invention, the direct detection of the molecules in and out of the cell has become possible when the cell shows some morphological changes in the living state. However, the provision of the method how to extract or exploring the molecules which hold the keys is essential in next step.

Figure 6:
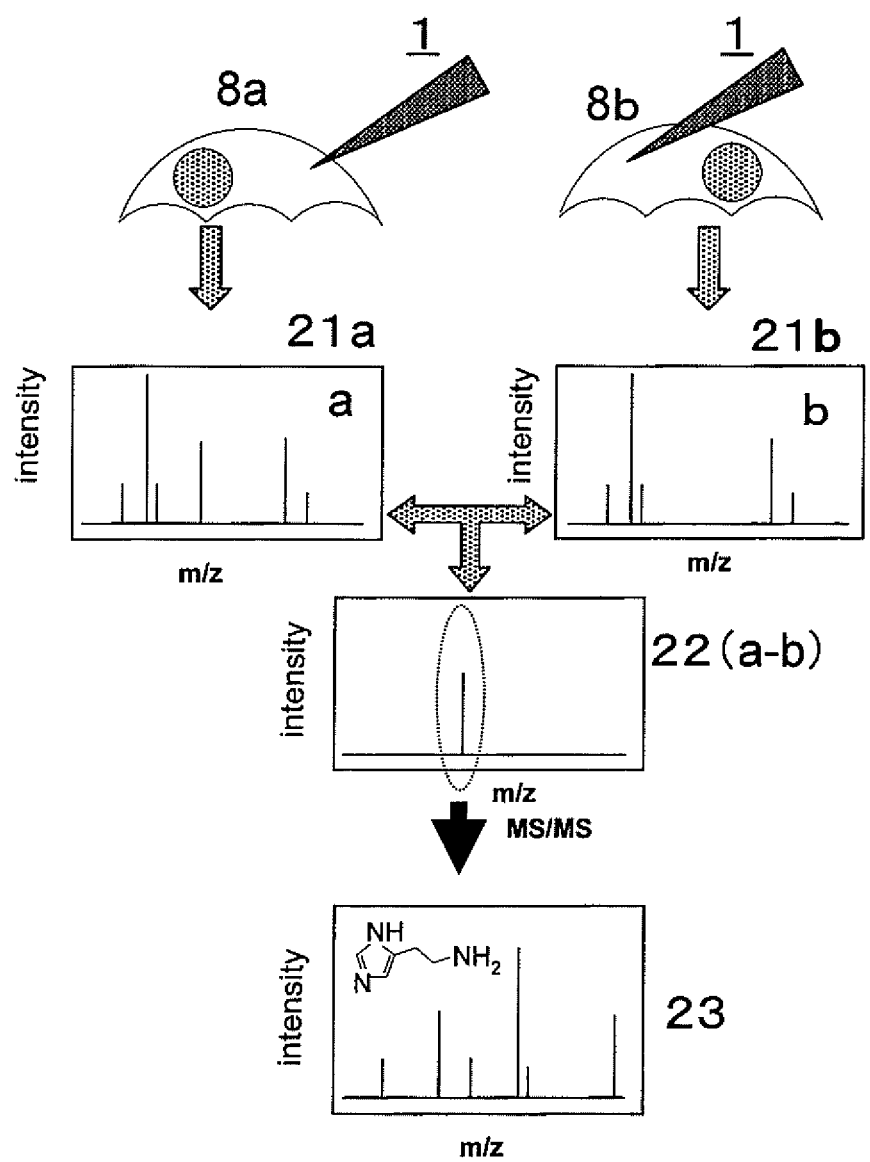

For molecular exploration which is important part of this invention, the difference of the spectra 21a and 21b are obtained which are obtained from the fluid of the cellular components in different states as shown in FIG. 6. (In this case, the mass spectrum is shown as an example. All of the analytical methods which can measure the peaks with high attribution of molecules or ions, specifically such as the spectrum of ICP mass spectrometry are acceptable.) (See FIG. 52 discussed below) The spectrum of the difference is obtained as 22(a-b) (in FIG. 6). In the case of mass spectrum, each peak is corresponding to each molecular species. With selecting the molecular mass by the mass filter in the former part of the mass spectrometer and then making the selected molecule collide with introduced gas molecule to break them (called fragmentation), the molecular fragments of the selected molecule are captured by the mass filter or time-of-flight mass spectrometer in the latter part of the mass spectrometer. The spectrum such as 23 can be obtained. It is called MS/MS analysis. Additional higher MS/MS/MS analysis can be also performed. The molecule can be identified from the specific fragmentation shown in MS/MS spectrum (FIG. 6).

FIG. 7 is one embodiment of peak extraction of state A specific one by using t-test comparing all peaks that shows the intensity over the threshold value of the peaks within all spectra at each cell state shown in FIG. 6. The data between each cell in the two states were compared by the computer programs. The m/z is used as the peak name 24 directly, and the accurate mass numbers in m/z 24 and t-values 26. This peak list shows that which peak is highly attributing to state A compared with state B. Within the many spectra obtained from a single cell, the peaks specific to state A are found from the top score of t-value which is the attribute index number to state A. The t-value 100 shows that the peak is 100% specific to state A. This kind of molecular exploration clarifies that the certain molecule is emerged or increased or decreased or disappeared at a certain moment or at a certain state specifically. This analysis gives us useful information to investigate the molecular functions and total molecular mechanisms by detecting the specific peaks (In the case of mass spectrometry, that is the molecule) to a certain state, a certain moment, after a certain stimulation or after certain treatment of the cell (e.g., addition of medical substances) with using t-values as index.

Multivariate analyses such as principal component analysis and cluster analysis, corelational analysis and regression analysis are effective for data analysis.

Figure 8:
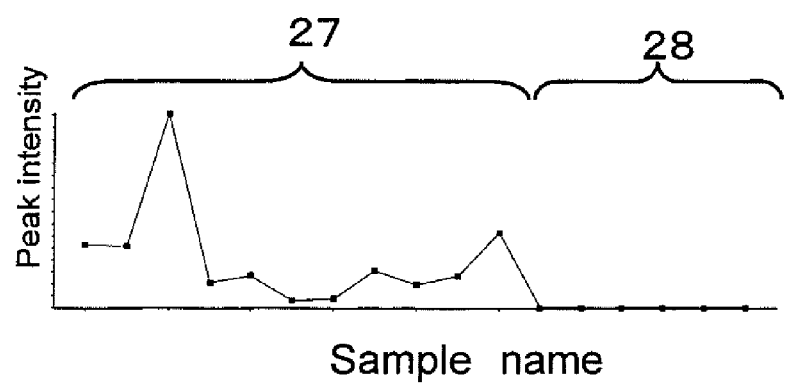

FIG. 8 is one embodiment of this invention showing in which sample the peak of m/z 112.1 was found specifically by t-test (as shown in FIG. 7). The peak is detected in the left eleven cell samples, but it is not detected in the right six cell samples. In fact, it can be shown that the molecule which shows the peak is specific to the state of left eleven cells and it is the molecule expressed in only this state. It is shown that the expression probability, dependence or attribution to the certain state is 99% by the t-value. In this way, the research of characteristic cellular behaviors with their molecular mechanisms, which is the goal of life science, is firstly enabled in a single cell level by this invention. Any combination of behavior analyses, molecular dynamism analyses and molecular exploring analyses of each cell become possible simultaneously and this invention provides the method to clarify both life phenomena and the molecular mechanisms rapidly and directly.

Figure 9:
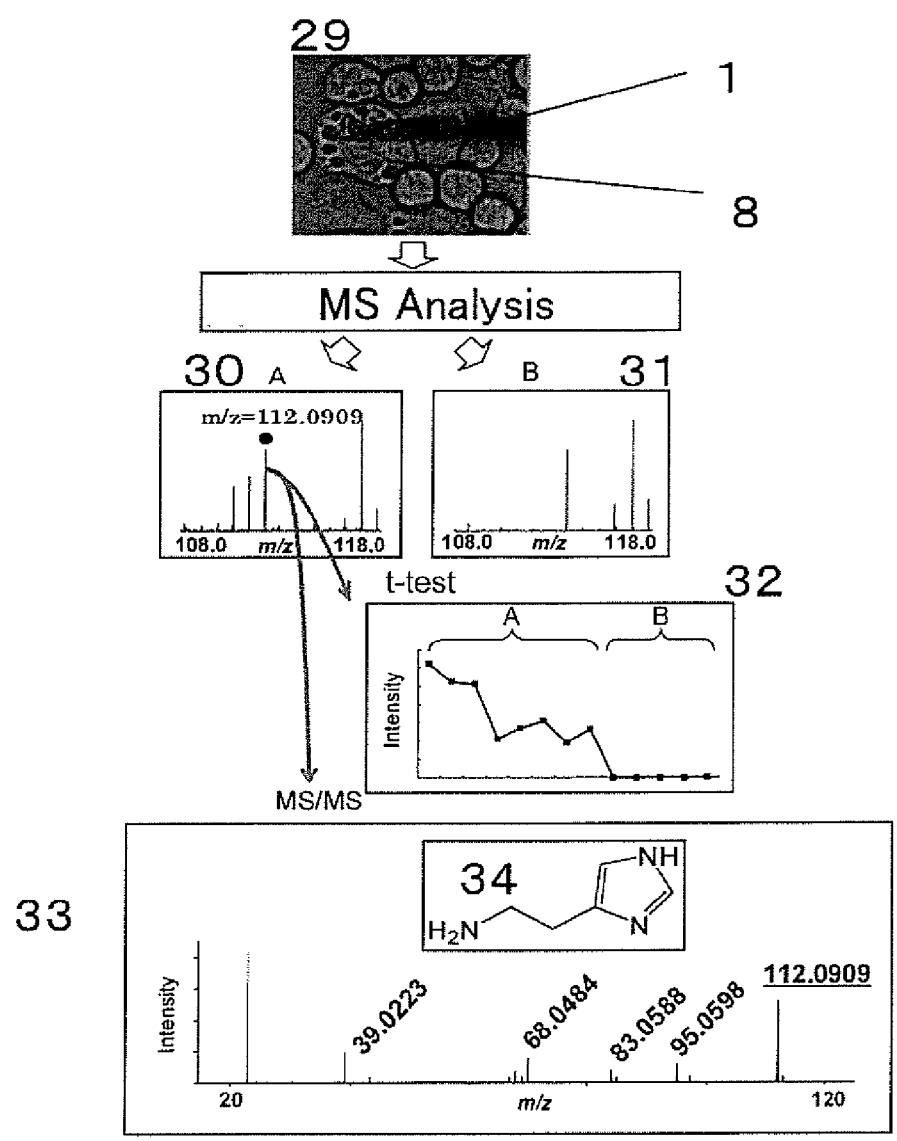

FIG. 9 shows the embodiment of above mentioned process comprehensively. The components of cytosol and the granule which is a subcellular organelle in the cell 8 were captured by nanospray ionization capillary tip (ionization capillary tip) 1 regio-specifically and then the ionization supporting solvent was mixed to the captured sample fluid, and high-voltage was applied between the said ionization capillary tip and the sample inlet of the mass spectrometer. Then nanospray was produced and the molecules of sample were ionized. The spectrum of the component in the granule 30 and the spectrum of the component of the cytosol 31 obtained by introducing the mass spectrometry directly. These two spectra were compared and the attribution of the cytosol and the granule between the different parts in the cell and was evaluated by t-test 32 about the peak of m/z 112.1. As a result, it was found that the peak intensity was present in the group A of spectra captured from the granule but it was not present in the group B of spectra captured from the cytosol. The molecule which shows the peak of mass spectrometry m/z 112.1 is selected by the mass filter and the molecular structure is determined by the MS/MS analysis. The molecule is identified as Histamine from its MS/MS pattern and it can be determined that there is Histamine as the molecule which is specifically present in the granule. Other various molecules are found. These molecules are correlated with not only the cellular behaviors and with site specificity observed simultaneously, but also other detected molecular groups. Then not only the molecular mechanisms of life phenomena are clarified, but also the found molecules can be candidate of new medical substances, or, if the cell is cancer cell, the discovery of molecules which cause the disease. The clarification of the mechanisms can be led for development of diagnostic method. There have been no previous cases in which molecules are detected from a single cell in such a short time, and in addition, with observed cellular behaviors, and be evaluated including the attributing degree of one molecular peak to the cellular behavior or cell state.

Figure 10:
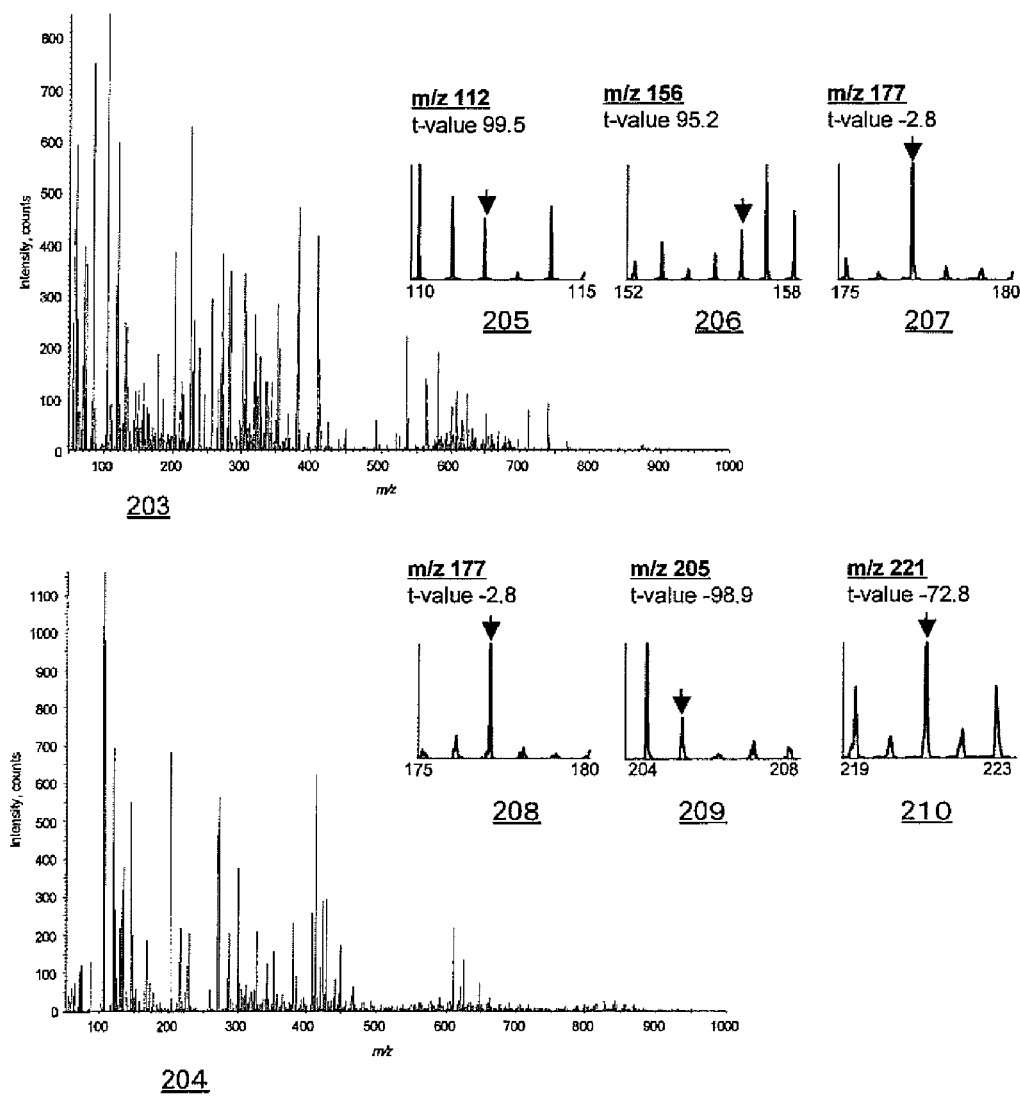

FIG. 10 shows the embodiment of the invention using the cell line called RBL-2H3 cells, the model of the mast cells which cause allergies. These cells have the granules in the cells as shown in FIG. 1, and it is said that the cells store the molecules which cause allergic reactions such as Histamine and Serotonin, so-called chemical mediator, in the granules selectively. The spectrum 203 is obtained by taking the component in the single granule of the single cell by the ionization capillary tip built up in the method of this invention selectively and introducing the component into the mass spectrometry by the nanospray ionization method. The spectrum 205, 206 and 207 are the enlarged spectra of the part of 203. The peak of m/z 112 which is seemed to be Histamine is detected in 205, m/z 156 seemed to be Histidine and its peak is detected in 206, and m/z 177 seemed as Serotonin which is detected in 207. On the other hand, the spectrum 204 is obtained by taking the cytosol side of the single cell by the ionization capillary tip selectively which is made by the method of this invention. The spectrum 208, 209, and 210 are the enlarged spectra of the part of 204. The peak of m/z 205 which is seemed to be Tryptophan is detected in 209, m/z 221 seemed to be 5-Hydroxytryptophan is detected in 210 and then m/z 177 seemed to be Serotonin which is also detected in 208.

However, the molecules cannot be determined by only these parent peaks because in nature, there are many other molecules which have the same mass number. There are two methods to determine what the molecules are. One method is so-called MS/MS method, selecting only the peak by the mass filter in the mass spectrometry, and then fragmented the selected molecule by molecular collision by making the gas molecule collide, capturing the fragments of the molecule (fragments) by the spectrum and identifying the molecule from the specific fragmentation. Another method is detecting the peak with high mass accuracy by the high-resolution mass spectrometry such as FT/MS analyzer and proving that the molecule is not other candidate by the exact mass.

Figure 11:
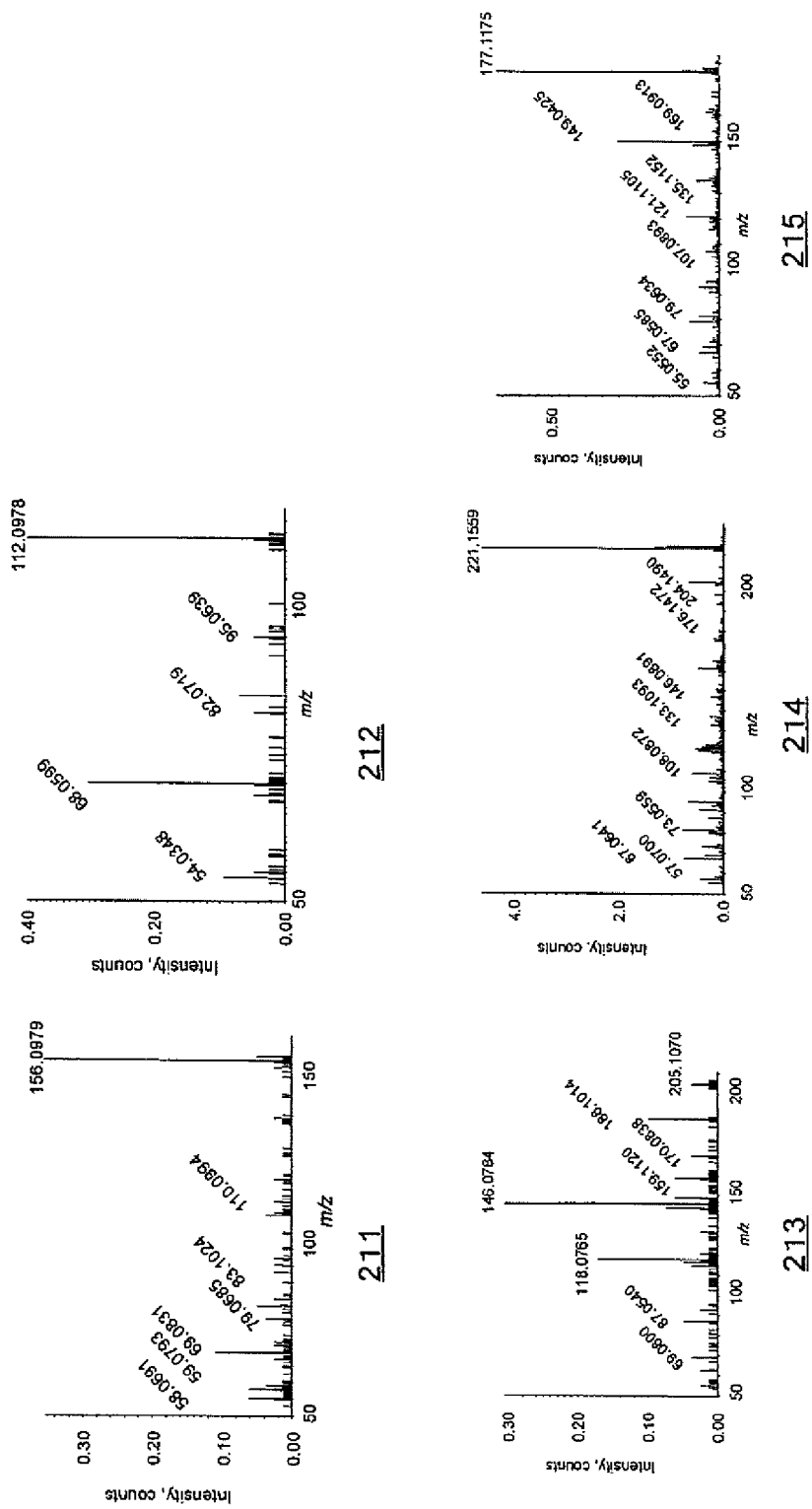

As shown in FIG. 11, the MS/MS analyses were performed to each peak in FIG. 10. As a result, it has been identified that the peak of m/z 156.098 is Histidine evidently from the MS/MS spectrum 211, the peak of m/z 112.098 is Histamine from the MS/MS spectrum 212, the peak of m/z 205.107 is Tryptophan from the MS/MS spectrum 213, the peak of m/z 221.156 is 5-Hydroxytryptophan from the MS/MS spectrum 214 and the peak of m/z 177.118 is Serotonin from the MS/MS spectrum 215 by comparisons of each MS/MS spectrum and the database (for example, Mass Bank.jp (http://www.massbank.jp/index.html)). Until now, it has taken long time, at least half a day by conventional molecular identification method in which we prepare the sample collecting many cells, and put them for homogenizing, previous sample pretreatment and sometimes performing separation. In addition, the obtained results are the average, and they don't reflect the clear state of the certain cell. In this invention, it takes 30 minutes to observe the cells and take the sample components and 30 minutes to measure. The molecular identifications can be done for about an hour (or less) in the case of the most rapid analysis. This invention has the outstanding ability to perform infinitely rapid analyses with the lucidness of results.

In addition, the results of t-test show that each peak can be detected specific to whether the granule or to the cytosol or neither to the granule nor to the cytosol are described under the m/z values written above the enlarged figures of the spectra of FIG. 10. Since t-value of +100% means completely specific to the granule side while −100% of t-value means completely specific to the cytosol side in this case, it is shown that Histamine of m/z 112 and Histidine of m/z 156 are present almost specific to the granule. On the other hand, it was found that Tryptophan of m/z 205 and 5-Hydroxytryptophan of m/z 221 were almost present in the cytosol. Surprisingly, it was found that Serotonin of m/z 177, which has been said that it is stored in the granule, was present in both the granule and the cytosol almost equally by this analysis for the first time. As shown in this result, not only the identifications of molecules but also the localizations of the molecules in or out of the cell can be shown directly in a short time by this invention.

Figure 12:
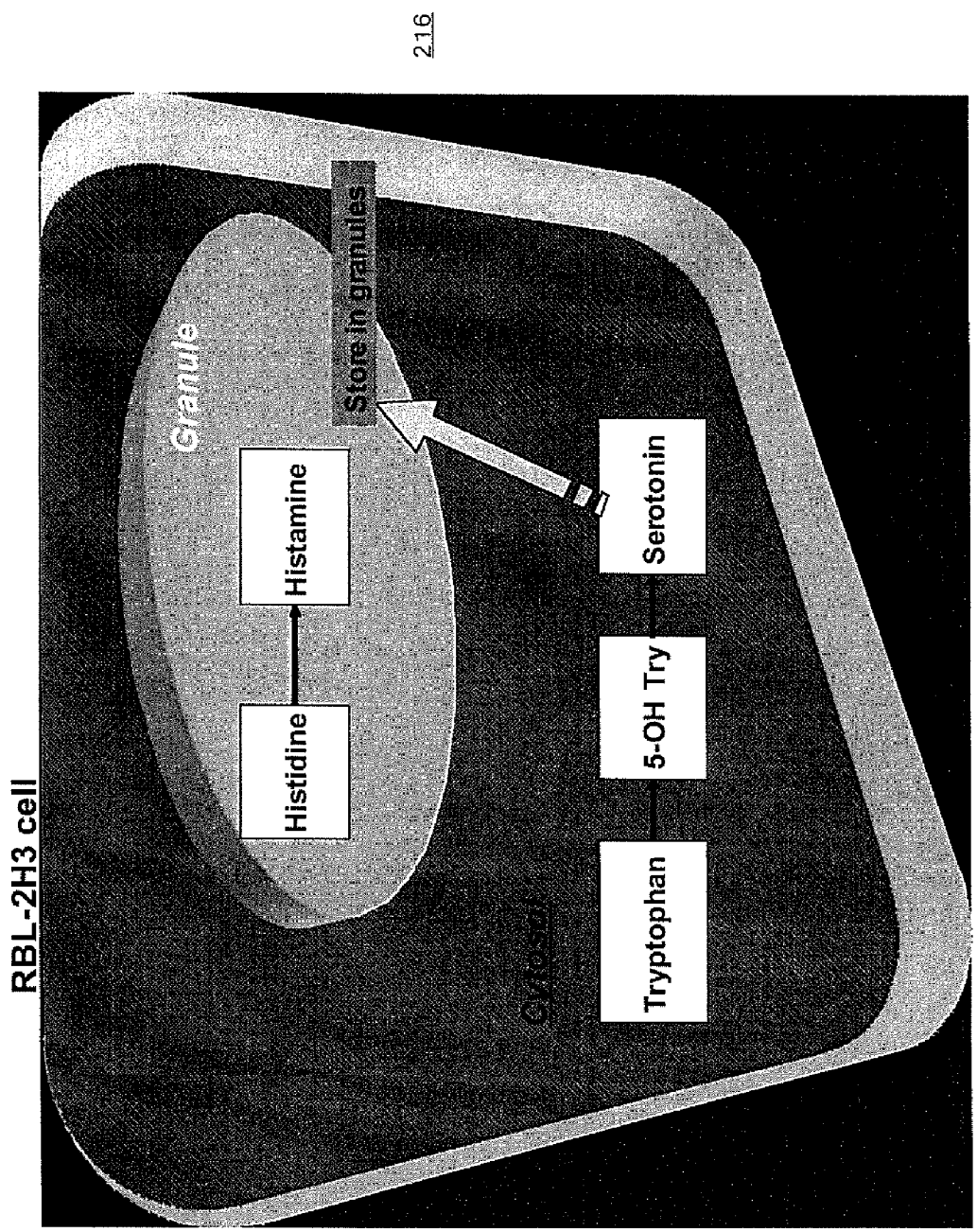

By integration of these above-mentioned results, the metabolic pathway of these molecules in a single cell can be clarified additionally as shown in FIG. 12. Together with the known metabolic pathway, the molecular localization clarified by above analyses shows that Serotonin is biosynthesized from Tryptophan via 5-Hydroxytryptophan in cytosol and transferred into the granule by transport. However, it is also clear that Histamine is biosynthesized from Histidine which is localized together in the granule and stored in the granule specifically.

As shown now, the metabolic pathway and localization of the molecules in the cells are clarified very easily and it shows how useful this invention is for the clarification of molecular mechanisms in rapid and direct way. Recently a lot of the metabolic analyses using mass spectrometry (commonly known as metabolomics) are performed, however, in all of these analyses, many cells are used as samples. We think that, so to speak, this invention has brought the age when the real-time single living cell metabolomics is possible.

Figure 13:
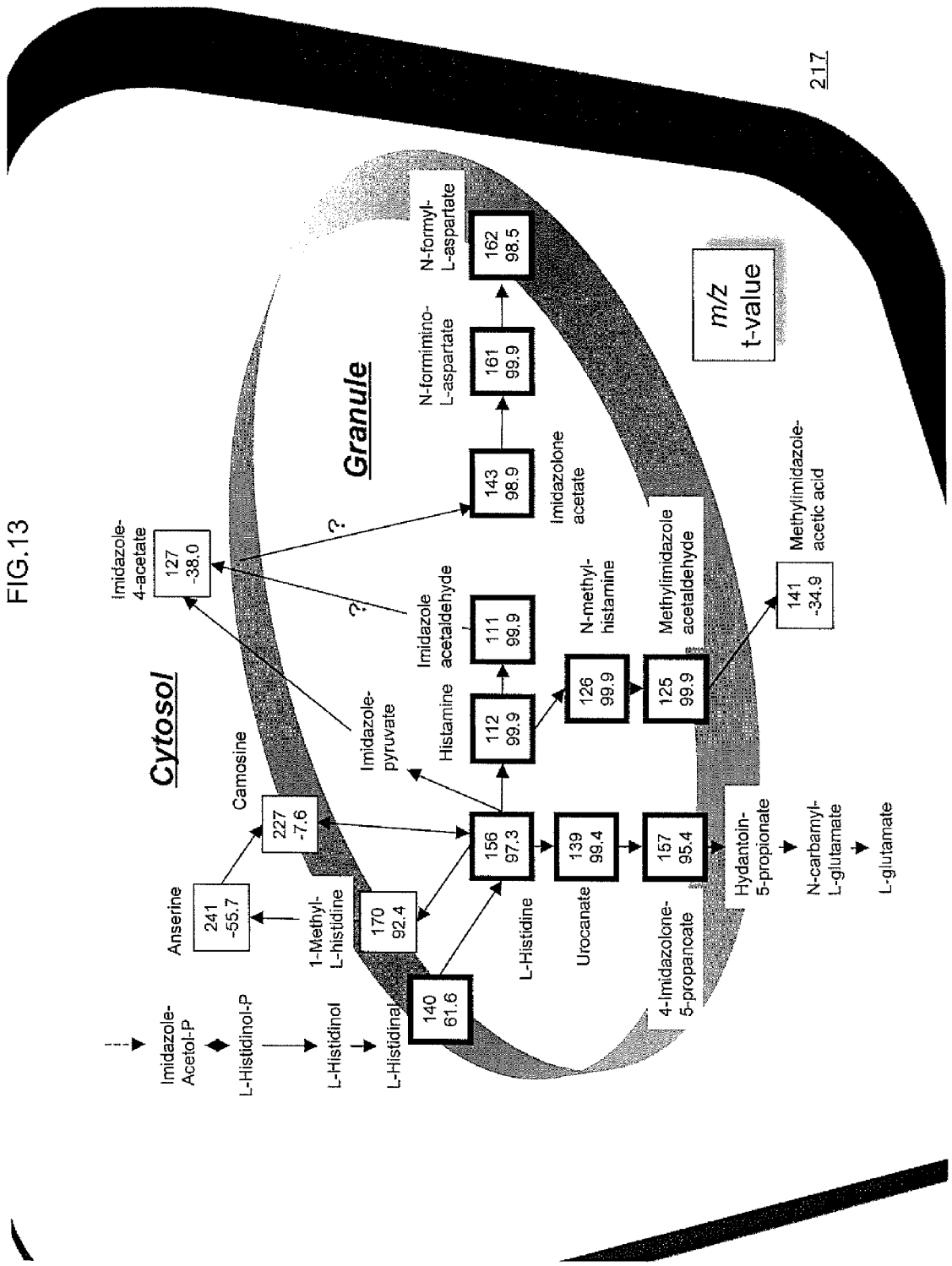

In addition, it was examined whether the tracking molecular metabolism was possible by above method. The components in the single granule in a cell was captured, and the similar analyses above-mentioned were performed for many more peaks and the molecular metabolic process in the single granule in a single cell (It can be called "the map of metabolism in the single granule") was explored as shown in FIG. 13. The m/z and t-values are described in the squares under each name of the molecules. As a result, the possibility that Imidazole-4-acetate whose pathway is added "?" is not present so much in the granule, but present in the cytosol side and lacking at the metabolic process in the granule (which is against the knowledge of averaged science).

As shown in this result, this invention gives the method by which the metabolic and transport processes can be traced with the localization information in a single cell.

This method is also applied for the detection of the molecular components popped out of the cell. FIG. 14 shows that the extracellular fluid around the cell is corrected by suction when the same RBL-2H3 cell as above mentioned is popping the granules out from the cell (It is called "exocytosis") like the video image 218 and similar analysis was performed. In this case, especially high detection sensitivity was needed because the component in the granule popped into the extracellular fluid were diluted in the culture fluid at once, but it was found that the peak of Histamine localized aside of the granule was detected in the partly enlarged spectrum 220 of the obtained spectrum 219.

In the mass spectrum, one peak presents one molecular species. Therefore, it is thought that the different kind of cells with complex molecular compositions show the mass spectrum of the certain cell species with the molecular peaks specific to each species while many molecular peaks are common to the cells. It is also thought that the changes of their components reflect the differences in its cell cycle stage or circumstances in micro region which are considered as one of the causes of the differences of cellular behaviors. So the difference among the parts of the same organ, which is cancerous, not be cancerous and the intermediate one can be evaluated by this method to be used for factor analyses of disease state.

Figure 15:
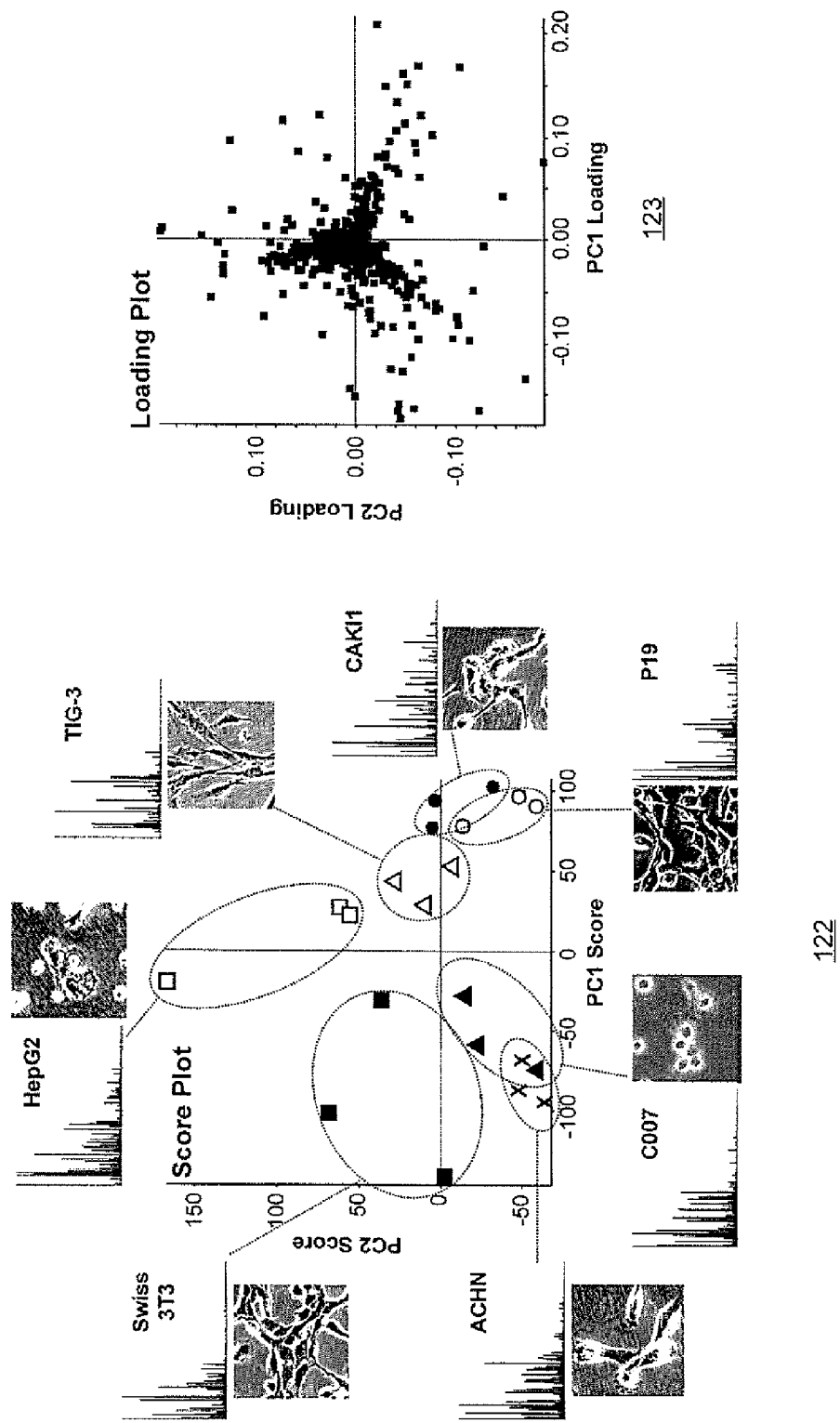

The difference of peak compositions of mass spectrometry was analyzed statistically and efficiently by using the multivariate analysis technique such as principal component analysis. FIG. 15 shows the approaches to distinguishing the different cell lines by comparisons of mass spectra of single cell. The spectra of cytosol and the microscopic images captured at the seven different cell lines are shown. The principal component analysis was performed based on these spectra because the difference was not clear by only the spectra and the images. The example of analysis for the cells of the seven cell lines by this method and performed results of the principal component analyses on these spectra is shown in 122 of FIG. 15 with the morphology images and the spectra of each cell. In the two-dimensional score plot obtained by the principal component analyses, the plot in which the contributions of each peak to principal component 1 and principal component 2 are plotted two-dimensionally. By plotting the scores, it was found that close cell lines formed a cluster covering a certain zone. It was found that the classification of the cell lines, conversely, the distribution of the species of low molecules in the cells in each cell was different. It shows that this method can relate the cell states to intracellular molecules with the molecular components and cell cycles which are linked to the cell differentiations.

The distribution of each peak in the spectra (Each dot is corresponding to each peak.) is shown in FIG. 15, 123 by two-dimensional loading plot. The peaks which have high commonality are plotted in the central zone, and the peaks which have high specificity are plotted far around from the center. By this plot, it was shown which peaks were specific to the cell species and it was found that the analysis could be used for discriminating the peaks to be performed MS/MS analysis in the next step.

Recently, establishment of exploration of cell differentiation factors and the method to control cell differentiation have been received attention for establishment of regenerative medicine such as induced pluripotent stem (iPS) cells. Until now, upstream molecules, so to speak, from genes as command center to translated proteins, have been studied well on cell differentiation by the science using average values. However, the behaviors of low molecules which are end products have not been studied because there are not many analytical methods. Since many low molecules are known as the cell differentiation factors, it is very important to research these low molecules.

Figure 16:
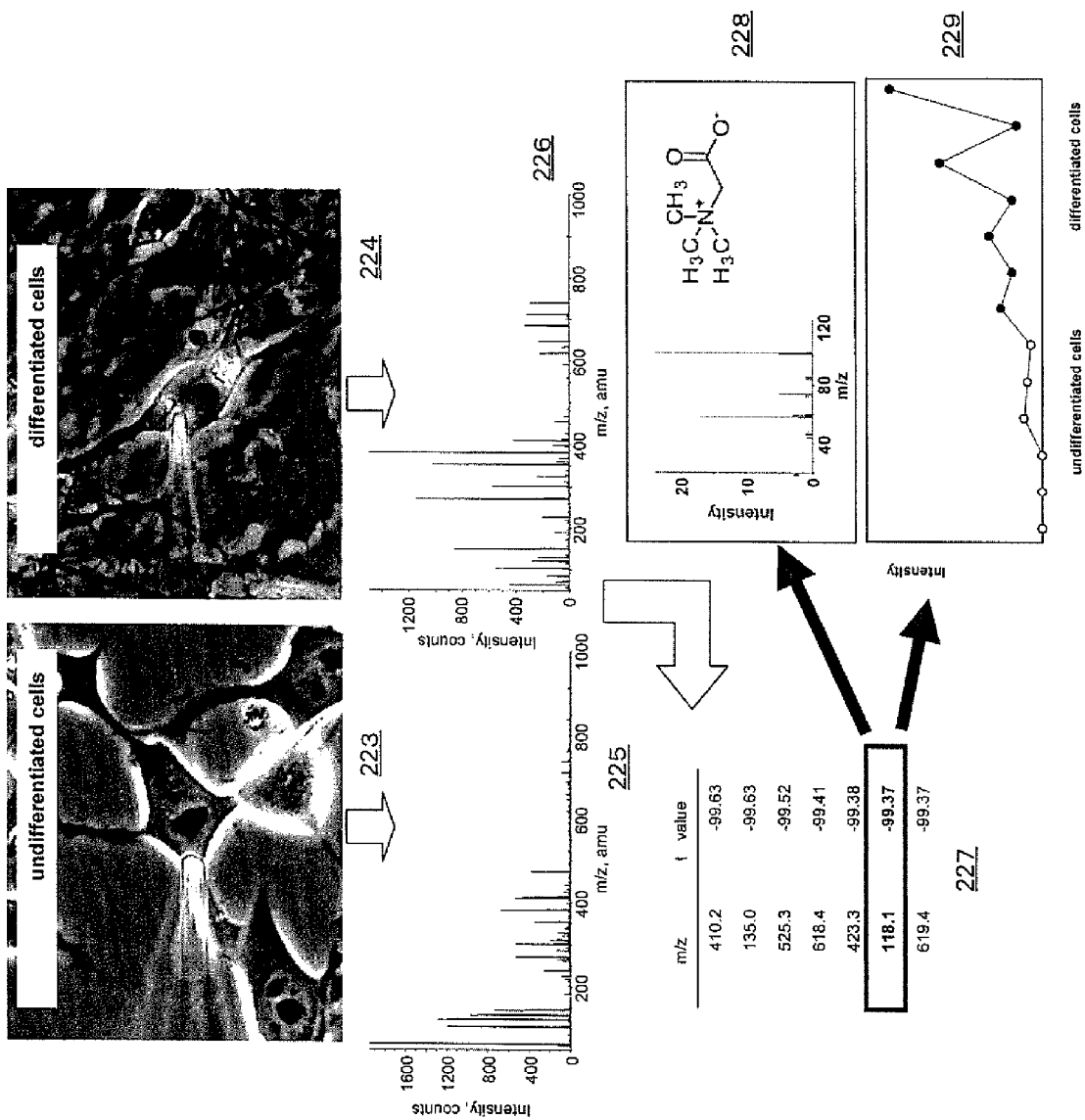

Thus, we have examined what kind of potentials this invention have for the analyses of cell differentiation mechanism and factor exploration. FIG. 16 shows the single cell tracking on the differentiation of P19 cell which differentiate into nerve cell by retinoic acid treatment. Image 223 shows the morphology of the P19 cell before differentiation and we captured of the cytosolic components by the ionization capillary tip. By retinoic acid treatment, the cells differentiate into the nerve cells which have processes like image 224. However, it was found that not all cells have differentiated as seen in the image, and it is necessary to take samples from the cytosol of only the differentiated cells. It was found again that this invention which can capture the sample components from single cell site-selectively has big advantage in application to this field.

The mass spectrum before and after the cell differentiation is 225 and 226, respectively. The peaks which increased after the differentiation were extracted by t-test from the peaks, and the peaks whose t-value are over −99.37% are shown in Table 227. It can be said that these molecules are the peaks which have increased by cell differentiation significantly. By MS/MS analysis of the peak of m/z 118.1, it was found that the peak was betaine as shown in 228 of FIG. 16 and the peak was increasing with progressed differentiation as 229 of FIG. 16. Now other molecular peaks are analyzed and clarified in relation to differentiation of this cell for increasing and decreasing molecules. It is shown that this method is also applicable to the differentiation factor exploration and the clarification of mechanisms of induced pluripotent stem cell which is in the news and will become the analytical tool which can accelerate the technological development of future regeneration medicine. In addition, this invention is available for the analyses of fate determination of each part of fertilized egg in the course of development which starts from cleavage after fertilization.

Figure 17:
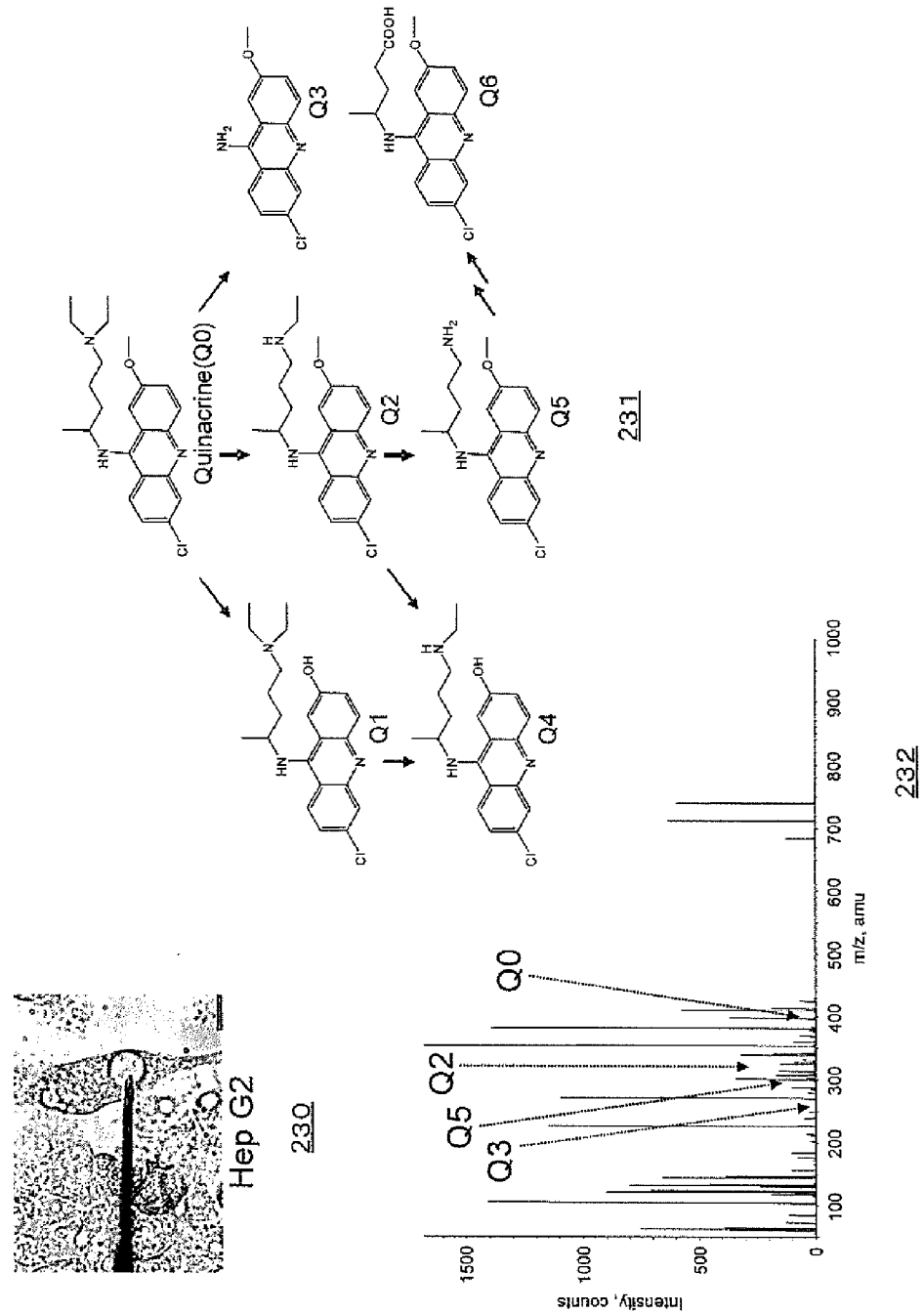

Recently, the development of personalized medicine which examines the difference in personal metabolism of used medicines for each individuals and plans most appropriate medications because there are individual differences in side-effects of the medicines which stress on human strongly especially in such as anticancer drugs. This invention is also available for personalized medicine and for accelerating the research of metabolism of developed medicine for the pharmaceutical companies. It was examined whether we can trace drug metabolism in a single cell by using Hep G2 (image 230), the model cell line of human liver cells. In the examination, Quinacrine which has been used as specific medicine to treat malaria is used as the model medicine. The substances such as 231, in FIG. 17 are known as the metabolite of Quinacrine. Quinacrine was injected in the culture fluid of the cells and the mass spectrum 232 of intracellular component of single cell was captured. As the result, it was found that Quinacrine and its metabolites was detected. In the case of pharmaceutical molecules, the parent compounds and their metabolites are usually known and it is enough to get the total image of the metabolism and mechanism and pattern of metabolism of drugs in each part of the cell or in the tissues. Instead, quantitative capability is usually emphasized. The tandem quadrupole mass spectrometer is often used for the high-sensitive quantitative determination of such determination of molecules. Generally speaking, the tandem quadrupole mass spectrometer has from dozens of times to one hundred times higher sensitivity than quadrupole-TOF (Q-TOF) mass spectrometer used in the above described analyses. The tandem quadrupole mass spectrometer can measure the known molecular groups changing the combination of setting m/z of two mass filters, called MRM. Multiple target molecular groups can be measured continuously with high-sensitivity if they are determinate molecular groups. It is possible to expand the sensitivity, quantitative capability and completeness of molecular detection separating them by nano-liquid chromatography etc. for high-sensitivity, although chromatography reduces sensitivity by spatial spreading of the component of a single cell when the usual column is used.

Figure 18:
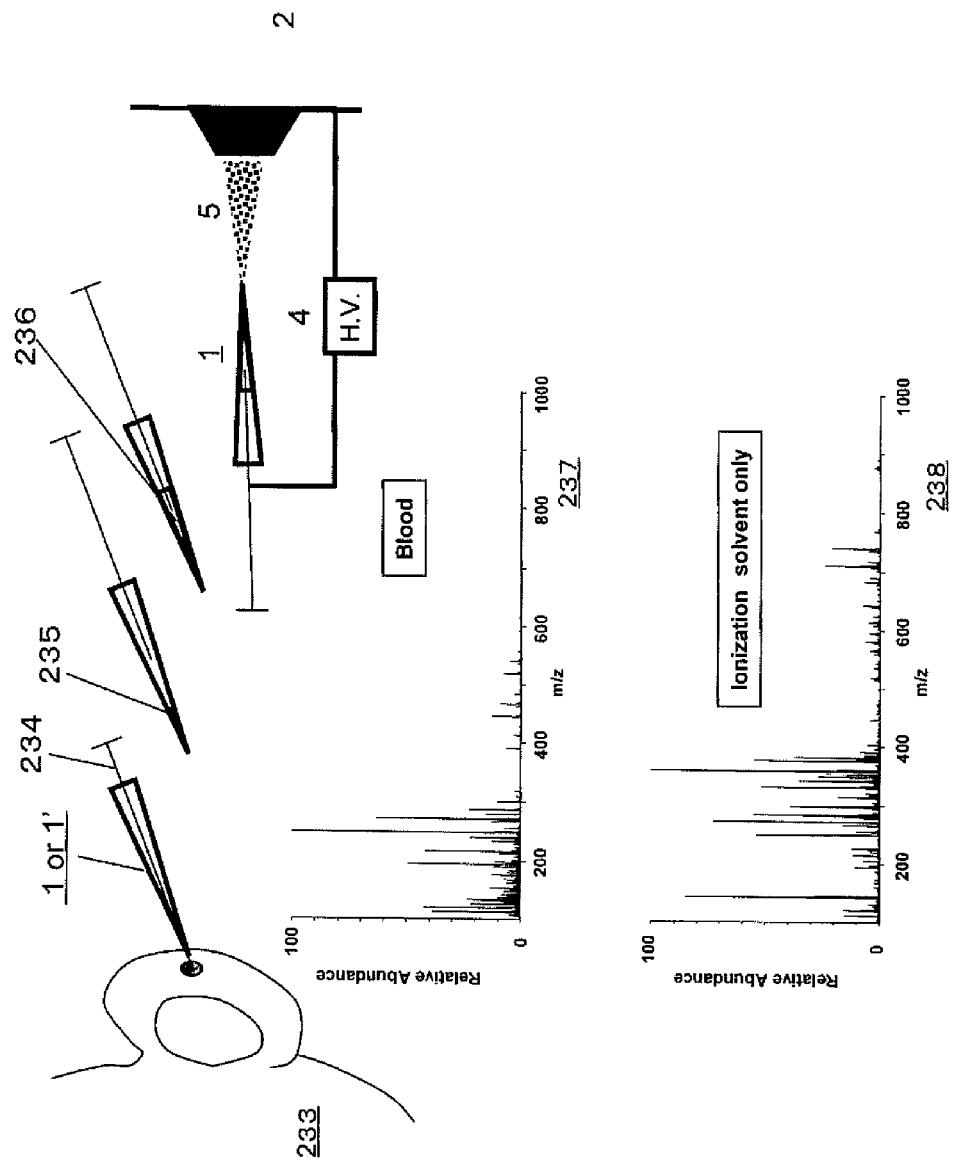

This invention has the potential to let us avoid blood samplings with painful needle injection at the diagnoses in hospitals. It is possible that multiple examinations of clinical tests will be replaced by tiny amount of blood sampling examinations with its mass spectrum measurement, when the micro sampling from such as the earlap is pricked with a needle lightly and a drop of oozing blood is directly subjected to the mass spectrometry by nanospray ionization with the method of this invention as shown in FIG. 18. As in the case of group of deviation enzyme in blood examined now, we only have to add each specific substrate to captured samples at nanoliter level, and after the reaction of a certain period of time, target the products specific to each enzymatic products from substrates, if these are determinate molecules, can be measured with the tandem quadrupole mass spectrometer which has high-sensitivity. In fact, when the examination was done partly, the spectrum 237 was obtained from only the blood taken from the earlap. Compared with the spectrum 238 of only added ionization solvent for confirmation, it was found that the different molecular peaks were detected. The detecting and analyses of molecular peaks which are suitable for clinical test items can be also established by using the same method of this invention as above mentioned. Although the ionization capillary tip is not used for inserting into the living tissue such as skin in FIG. 18, the ionization capillary tip can be also used for inserting directly. In that case, the outer surface of the ionization capillary tip can be coated by lubricate materials to smoothen the inserting such as silicone oil and sugar chain polymers. This measurement method is available for any other body fluids such as urine, saliva, tear and sweat.

Figure 19:
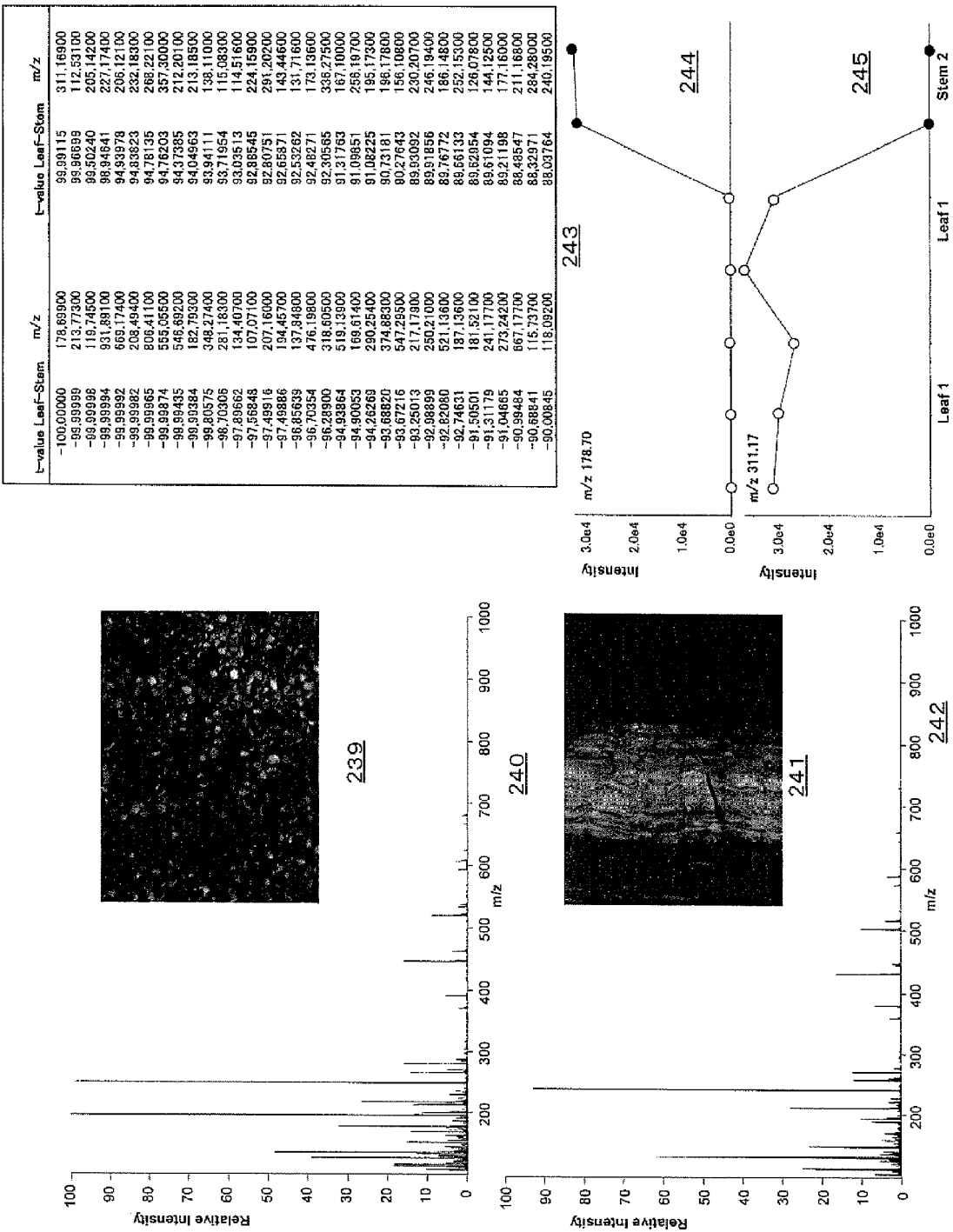

The animal cells have been discussed as measuring object up here. However, there are various applications of this invention also to plants for such as analyses of food materials, residual pesticide analyses, identifications of plant species, monitoring of nutritional conditions or disease states of plants and explorations and content analyses of useful components. The result of capturing the components by inserting the nano ionization capillary tip into the single cell of the leaf and stem of geranium under the microscope directly is shown in FIG. 19. Image 239 is the microscopic image of the leaf and it was found by enlarging the image that not only green cells but also the white cells which contain little chlorophyll were mixing. 240 is the spectrum obtained by inserting the ionization capillary tip into the white cell and analyzed the intracellular component as described previously. On the other hand, the analysis of the stem of geranium was easier and the spectrum like 242 was obtained. Table 243 is the result of t-test of each peak of the obtained spectra and it was found there were many molecular peaks specific to the leaf (the left column) and specific to the stem (the right column). Among them, it was found that the molecule which showed the peak of m/z 178.70 was the component which was present in the stem side specific as shown 244 of FIG. 19 and the molecule which showed the peak of m/z 311.17 was the component which was present in the leaf specifically as shown 245 of FIG. 19. As shown in these results, it was verified that this invention is useful for the identifications and explorations of intracellular molecules for plants too.

Figure 20:
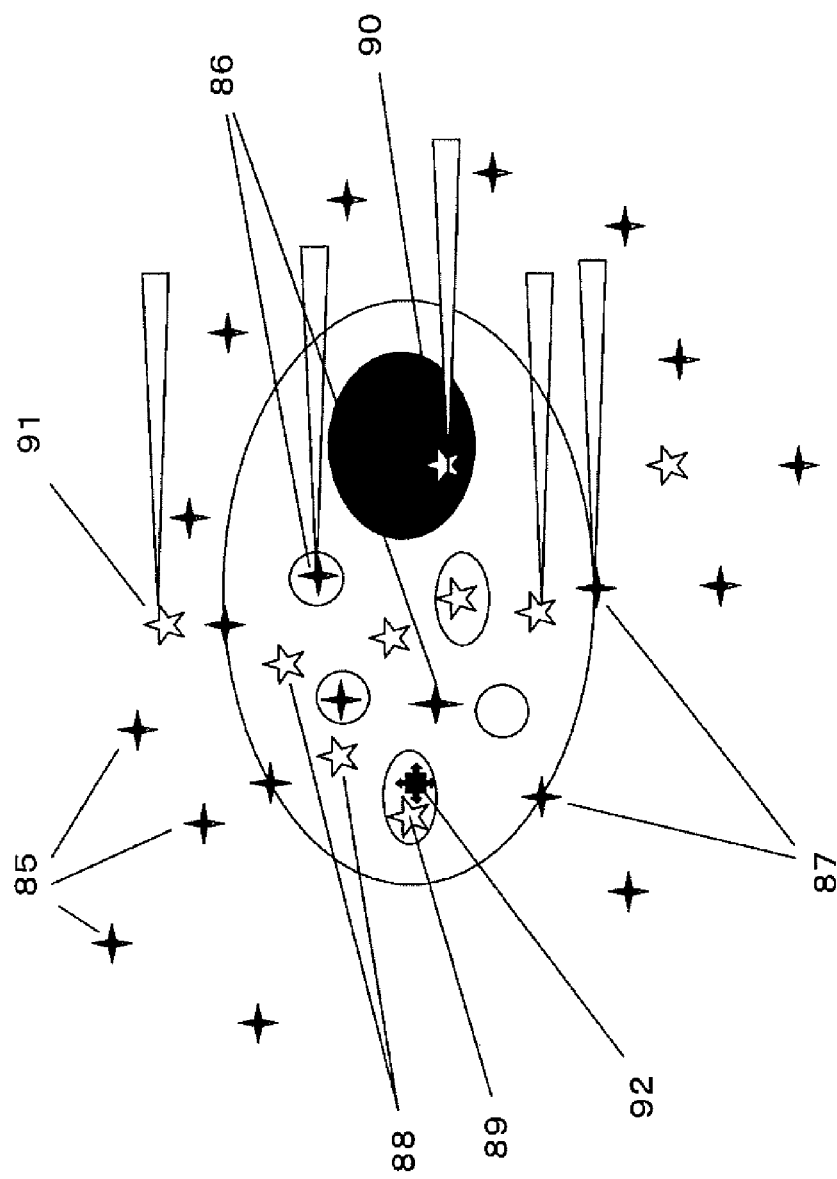

Life phenomena are changing dynamically with time. The analyzing power will expand moreover to combining use of the various molecular labeling methods and this method additionally tracks the molecular changes. FIG. 20 shows the method for tracking mass transfer and substance metabolisms in or out of cells by this invention. For example, the labeled molecules or traceable isotopic molecules (Collectively, they are called "labeled molecules" below.) 85 are added in the extracellular fluid, and then the molecules can be traced by setting the specificity by the mass shift seen in the mass spectra as the indicator by mass spectrometry. The labeled molecules 85 are introduced in the cell, then the molecules are distributed as labeled molecules 86 or as unchanged isotopic molecules for tracking which moved into cell and exist in intracellular fluid or in sub-cellular organelle and their localizations are detected by this method. The molecules are detected as labeled molecules or isotopic molecules for tracking which were introduced into or bound to membrane 87 at the capture of the membrane component. Labeled molecules or isotopic molecules for tracking were metabolized or modified while moving into cell 88, or labeled molecules or isotopic molecules for tracking were introduced into sub-cellular organelle 89 or changed as metabolites of them 89'. Labeled molecules or isotopic molecules for tracking can be trans-located into or introduced into nucleus 90 and labeled molecules or isotopic molecules for tracking can be metabolized or modified and then secreted or re-released into extracellular fluid 91. By this method, the total image of substance metabolisms and molecular transfer in or out of cells can be clarified at a single cell level.

Figure 21:
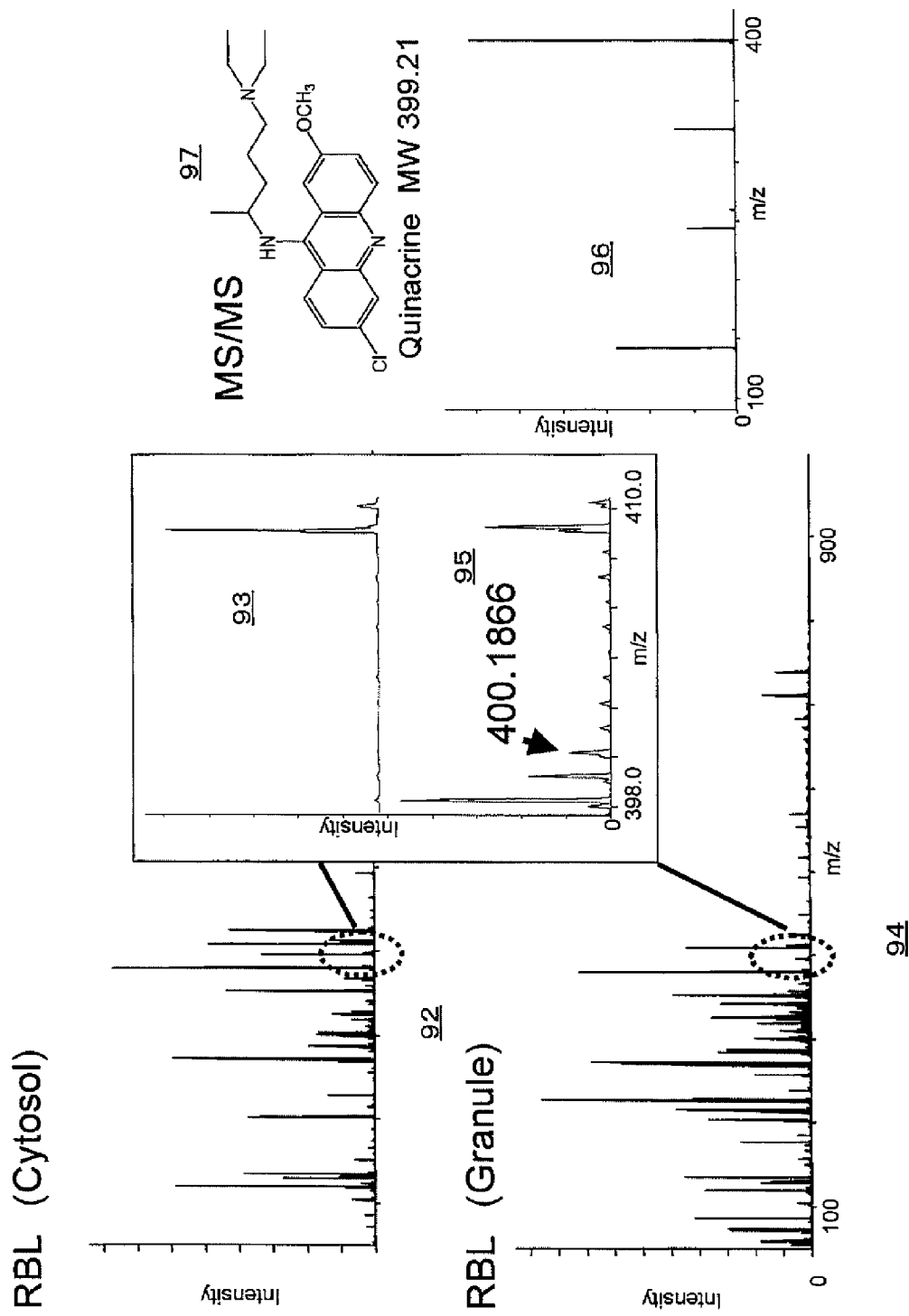

FIG. 21 shows the tracking Quinacrine (fluorescent substance) which is selectively introduced in the intracellular granules from outside of the RBL-2H3 cell, the model cell line of mast cell. It was found that Quinacrine molecule introduced from outside of the cell didn't remain at the cytosol but included in the granules because Quinacrine molecule was not detected in the spectrum of the cytosol 92 even in the enlarged spectrum 93 and it was detected in the mass spectrum of the granule 94 as a weak peak 95. It was confirmed that it was surely Quinacrine molecule judging from the MS/MS spectrum 96. The spatial resolution of this method is determined by the diameter of the top bore of capillary tip 1. It can be said that the spatial resolution is 1 micrometer because now the diameter of the top bore is 1 micrometer. This invention can be applied to multi-component medicine, like Chinese medicine. The mechanisms of medicinal effects with simultaneous collaboration of molecules of various components now will be able to be clarified. The complex of molecules can be introduced into the target cells or tissues by transfer and will work as medicine. It can be detected by measuring the mass spectra of components of crude drugs at first, and then inject the components of mixtures into the target cell or culture fluid or circulating fluid in tissues and analyzing the peaks of the component which transferred into the cell with observation of cell morphology. The time course shows the intracellular molecular localization and dynamics of the molecules which shows medicinal properties. We think this invention provide the potential which has never been thought until now for more comprehensive development of multiple component collaboration type medicines from conventional vision of the medicine which has one medicinal effect by one molecular species.

Figure 22:
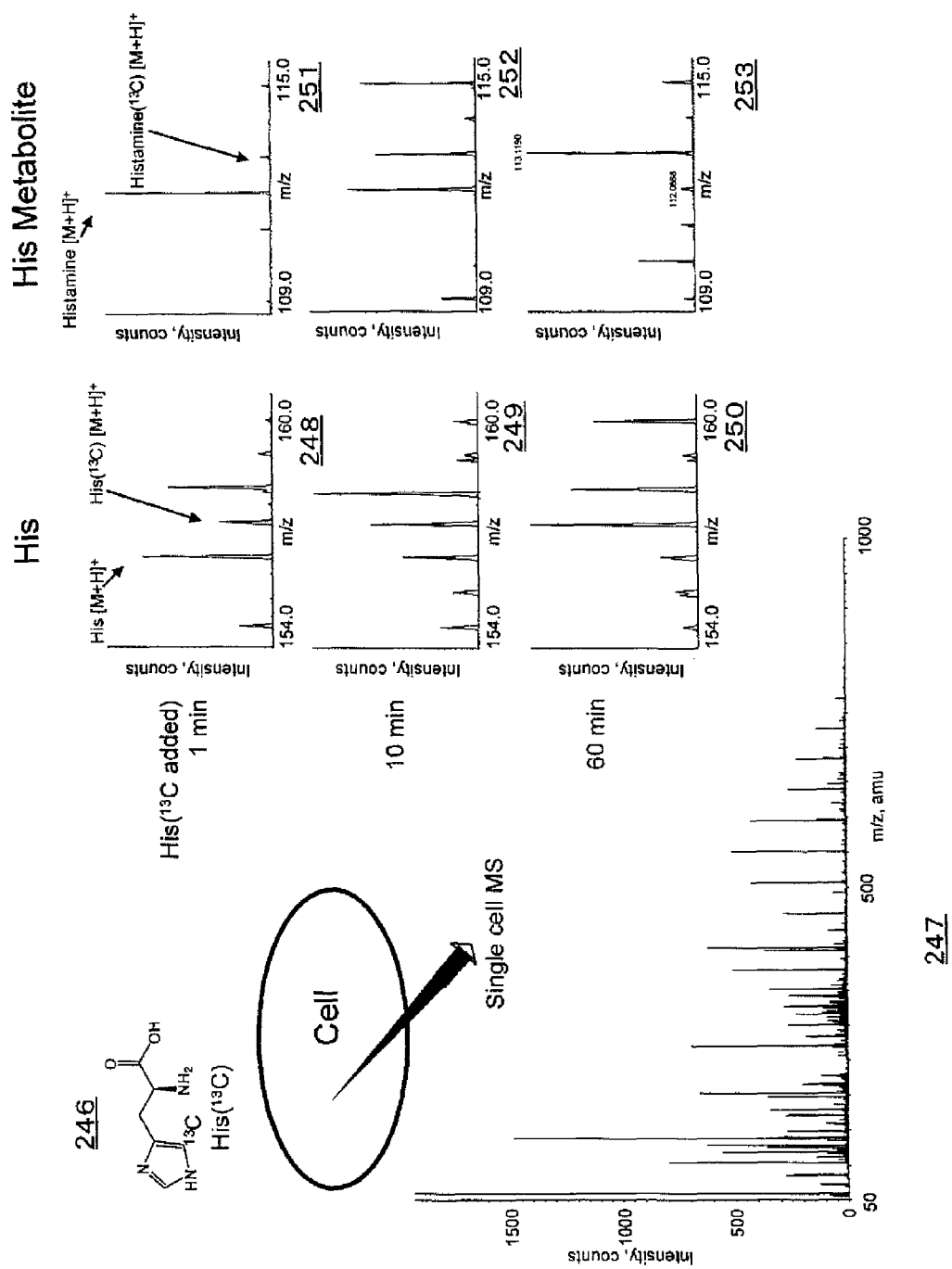

FIG. 22 shows the example of tracking Histidine introduced into the intracellular granules and how Histidine is metabolized by using stable isotope labeled Histidine 246. One more Histidine peak of stable isotope labeled one has been detected which was transferred into the granule in one more higher mass unit of the peak of Histidine in the mass spectrum of the component of intracellular single granule in the single cell 247. It is understood that Histidine has been detected by transfer from cell membrane to cytosol and then into granule because the isotopic Histidine has increased with time, as shown 1 minute after (248), 10 minutes after (249) and 60 minutes after (250). In corresponding to this, it was observed that Histamine, the accumulated metabolite of Histidine, has been accumulated in the granule with delay as shown 1 minute after (251), 10 minutes after (252) and 60 minutes after (253) accordingly, and considerably accumulated at last. It is possible to enable the detections of the molecules with higher peaks by reacting the sample components with such as high efficient amino-group labeling reagents mixed into the ionization supporting solvent to be added from the back-end of the capillary tip. This can enables the structural analyses including the high molecules by MS/MS analyses.

For measurements of enzyme activity of the biological fluids, such as cell components or blood, can be measured also by mixing the substrates in the ionization supporting solvent added from the back-end of the ionization capillary tip or by adding a constant amount of aqueous solution containing the substrates by nanoliter injector, causing enzyme reactions of them with the enzymes in the sample for a while followed by measurement of the substrates and reactants after a certain period of time. In addition, the components which disappear by binding to the cellular components or the specific components in body fluid such as blood can be analyzed by the same method by adding the binding molecules in tiny amounts to the sample solution. The evaluations of the concentrations of binding components, the distributions of binding components and the binding fractions can be performed.

The applications of labeled compounds are expected to extend the potential of this method much further.

To ensure quantitative capability of this method is also the important problem. It is difficult to add internal standard, because the object is ultralow volume at less than 1 picoliter. However, in the case of using mixture of eluting solvent and ionization supporting solvent 72 for nanospray, it is possible to correct each peak intensity of the single cell mass spectrum by the peak intensity of added isotope or internal standard materials which doesn't exist naturally.

Figure 23:
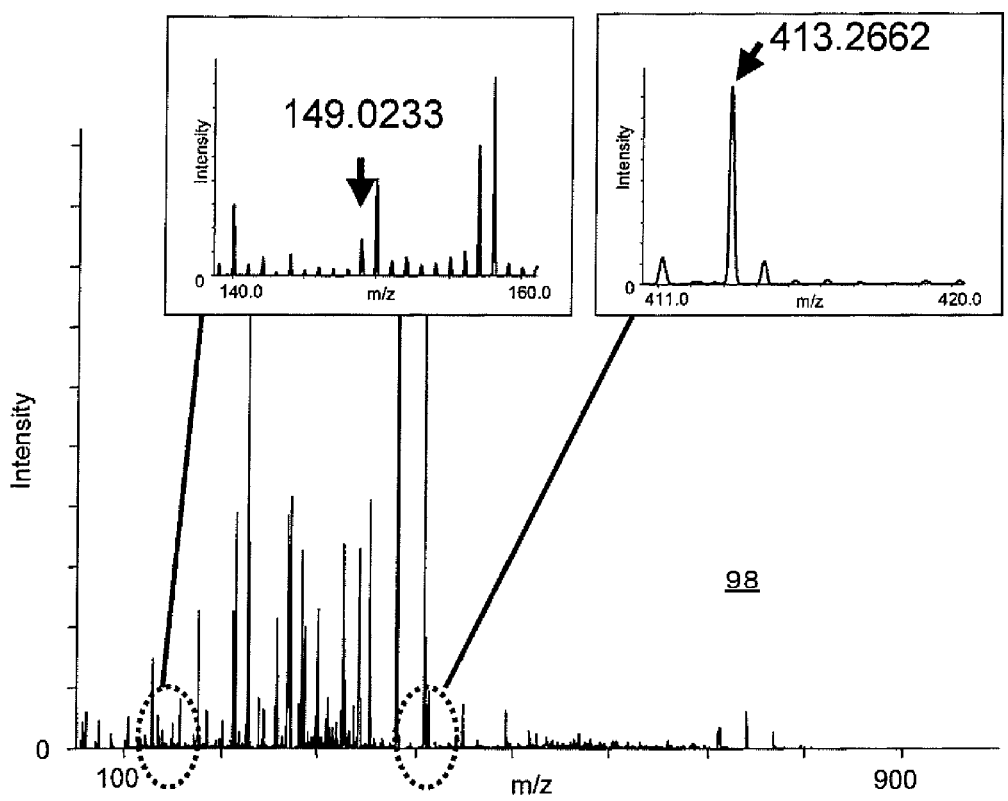

In addition, we have determined that the peak of added solvent 98 is available as the base peak intensity of spectrum. One of the examples is shown in FIG. 23. It is the peak derived from Dioctyl Phthalate contained in the mixture of eluting solvent and ionization supporting solvent 72. It is possible to correct or normalize the spectrum intensity with this peak.

It has been convinced that this invention has very wide applicability and speed and efficiency of analyses. In these verification studies, various inventions have been made in instrumentation and methodology because of various necessities of analyses. These inventions are descried here after.

Figure 24:
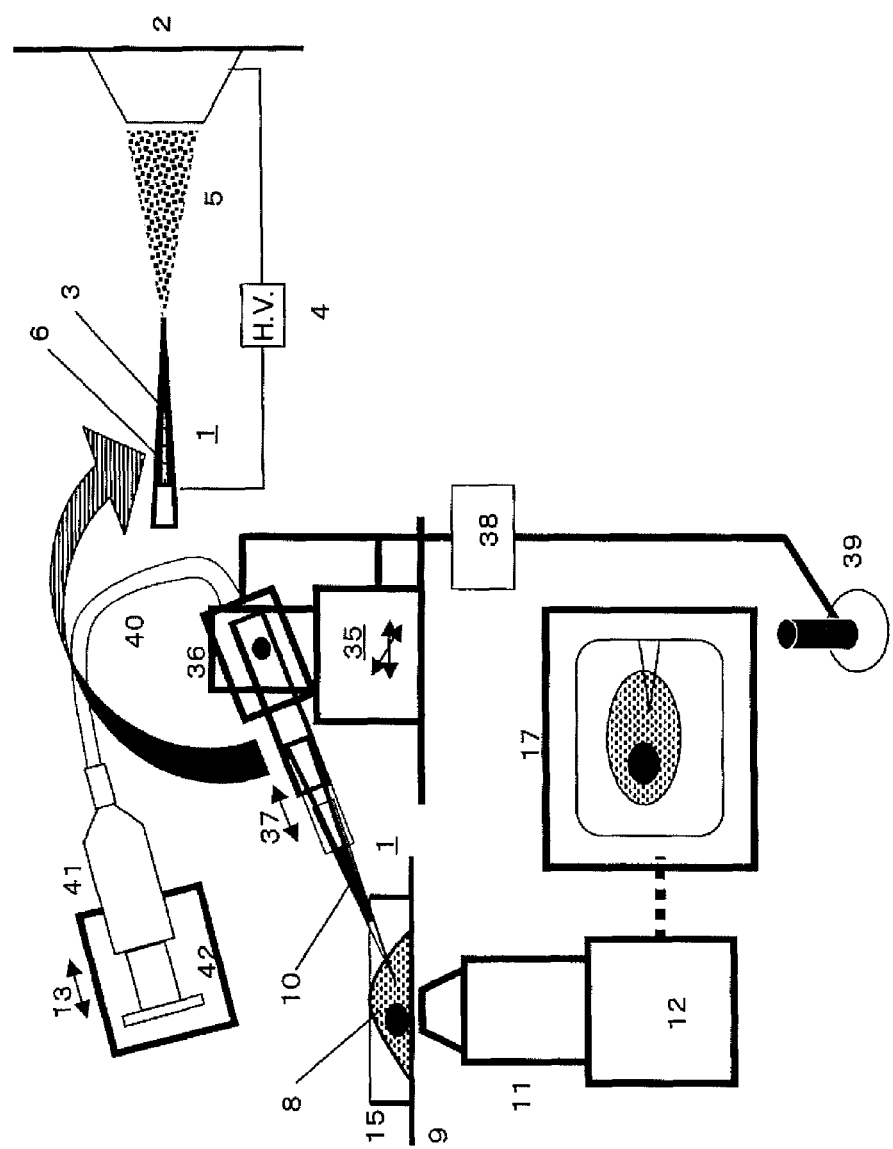

FIG. 24 shows a series of the methods and necessary system for detecting single cell components by mass spectrometry as the efficient practice of this invention. The nanospray ionization capillary tip 1 (It is abbreviated as "ionization capillary tip" below) formed by the conductive capillary is what is made by extended capillary made of insulator (mostly glass or plastic) by such as heating whose preferred diameter is less than 4 mm at a maximum and tapered narrow to top side. The diameter of inside of the top bore of the capillary tip is formed optimally less than the size of the cell or the sub-cellular organelle which is the object of capturing. The outer surface of the tip is coated with metal material 6 (mostly gold or nickel) by sputter method or vacuum evaporation method to make it conductive. The conductive capillary tip in this invention means the capillary tip whose inner surface or the outer surface or both inner surface and outer surface or the material itself of the capillary tip have conductivity. For the conductive surface, it is acceptable that the ionization capillary tip itself is conductive, or coated or embrocated or chemical treated one by conductive material. The region which has conductivity need not to be covered the entire surface of capillary tip. It is enough if the part of the top bore is widely electro-conductive, it is enough even if the electrically-contacted area is partial for applying the electric voltage and the part of the top bore are electrically-connected to other part. The conductive materials include conductive metals and conductive organic materials but the conductive materials aren't limited to them. The methods of conductive coating include vacuum evaporation coating, sputtering and embrocation, however, the methods of conductive coating aren't limited to them.

It is preferable that the top bore of the conductive capillary tip which is in contact with the cell and fluid of micro region is as small as possible at the top bore, and less than 100 micrometers is preferable for easy nanospray ionization of inside liquid sample. If the diameter is large, droplets of the nanospray become large and a slight amount of sample is sprayed out rapidly, and the sensitivity becomes worse and the ionization efficiency decreases. Preferable diameter is less than 50 micrometers, and the diameter which is more preferable is less than 10 micrometers, because the droplet size of the spray becomes small and the ionization efficiency increases and the size of top bore should be smaller than trapping size of cell or organelle or fluids in micro region. The smallest diameter is the size into which cell fluid and fluid in micro region can be sucked. The smallest size is limited in relation to the viscosity and the affinity of capturing fluids with the inner surface of the top bore of the capillary tip. The sample fluid with high viscosity can not be sucked in the capillary tip if the smallest diameter is not enlarged. It can be used that the sample fluid will enter into the capillary tip by itself with capillarity at decreasing the pressurization when the fluid has high affinity with the inner surface of the capillary top bore.

The sample solution 3 is sucked from a single cell or the subcellular organelle which is smaller than several micrometers in the capillary tip, the ionization supporting solvent (Formic acid and acetonitrile, or alcohol et al are used usually in positive mode) is added to the sample from the back-end of the ionization capillary tip near the surface of the sample in the forefront by using Eppendorf micropipette tip with capillary like fiber and air bubbles are removed by vibration. After that, if it is necessary, the prepared sample solution is filled to the forefront of the capillary tip by centrifugal force or pressure to the forefront of the capillary tip 1.

After this operation, the forefront of 1 is arranged coaxially with the inlet of the mass spectrometer 2 away from several millimeters to several centimeters from the inlet. And the high-voltage electric field optimally from several hundred volts to several kilovolts 4 is applied between the part which is conductively coated 6 of 1 and the inlet of the mass spectrometer 2, then extremely capillary electrically-charged particles of liquid are emitted like a capillary spray. It is called nanospray 5. Such a capillary tip for nanospray ionization 1 (It is abbreviated as ionization capillary tip.) is the conductive capillary tip. It functions not only if the outer surface of the capillary tip is conductively coated, but also if the inner surface of the capillary tip is conductively coated, both the inner and outer surface of the capillary tip are conductively coated and if the whole capillary tip is formed of conductive material such as metal for securing conductive property.

The captured cell fluid 10 directly and the sample, the above ionization supporting solvent was added to the cell fluid 10, can be analyzed by using the capillary tip 1 directly for suction of the entire cell 8 kept alive in the culture fluid in the Petri dish 15 placed on the microscope stage or the fluid in the cell 8 or the organelle in the cell 8 like a granule (Or, if it is necessary, the extracellular fluid, too, of course.) because the formed nanospray ionization capillary tip 1 can suck even the solution less than several picoliters from a single cell and at the same time, perform the nanospray stably by adding the above ionization supporting solvent like this. It was discovered that the intracellular low molecular groups could be done ionization sample introduction for mass spectrometry directly by simple operations. This is because low molecules are eluted to the organic solvent component of the ionization supporting solvent while proteins et al become deposited, bind to the inner wall of the capillary tip 1 and don't move if the ionization supporting solvent is mainly organic solvents (See FIG. 32 below) Thereafter, the operations of taking the internal fluid of almost single cell have become extremely simple, the molecular measurements have become directly and rapidly and it was found that the component molecules including what exist only as ultralow volume like intracellular fluid could be clarified by mass spectrometry.

FIG. 24 shows the appearance of pricking the cell by operating 37 the forefront of the capillary tip by X-Y-Z driving stage 35, angular and axially-moving actuator 36, the control device for driving 38 and the handle for operating the manipulator 39 of the electric manipulator which sets the capillary tip at the top observing the insert of the ionization capillary tip 1 into the cell 8 by the video microscope 11,12 and the monitor 17, and the appearance of driving 13 the capillary tip by the piston driver 41 to enable the suction and capture of the intracellular component by the piston 41 without transmission of the vibration at sucking to the forefront of the capillary tip 1 via the tube for suction drive of cellular components. It was found that the peaks of molecules contained in the tip was appeared as the mass spectrum by capturing the intracellular fluid 3 like that, removing the capillary tip 1 from the manipulator, adding the ionization supporting solvent to the sample, transferring the capillary tip to the position for nanospray of the mass spectrometer 2, applying the high-voltage 4 by the high-voltage power supply and causing the nanospray. Hereinafter, the descriptions about the words which are given the same number are abbreviated because they are the same things.

Figure 25:
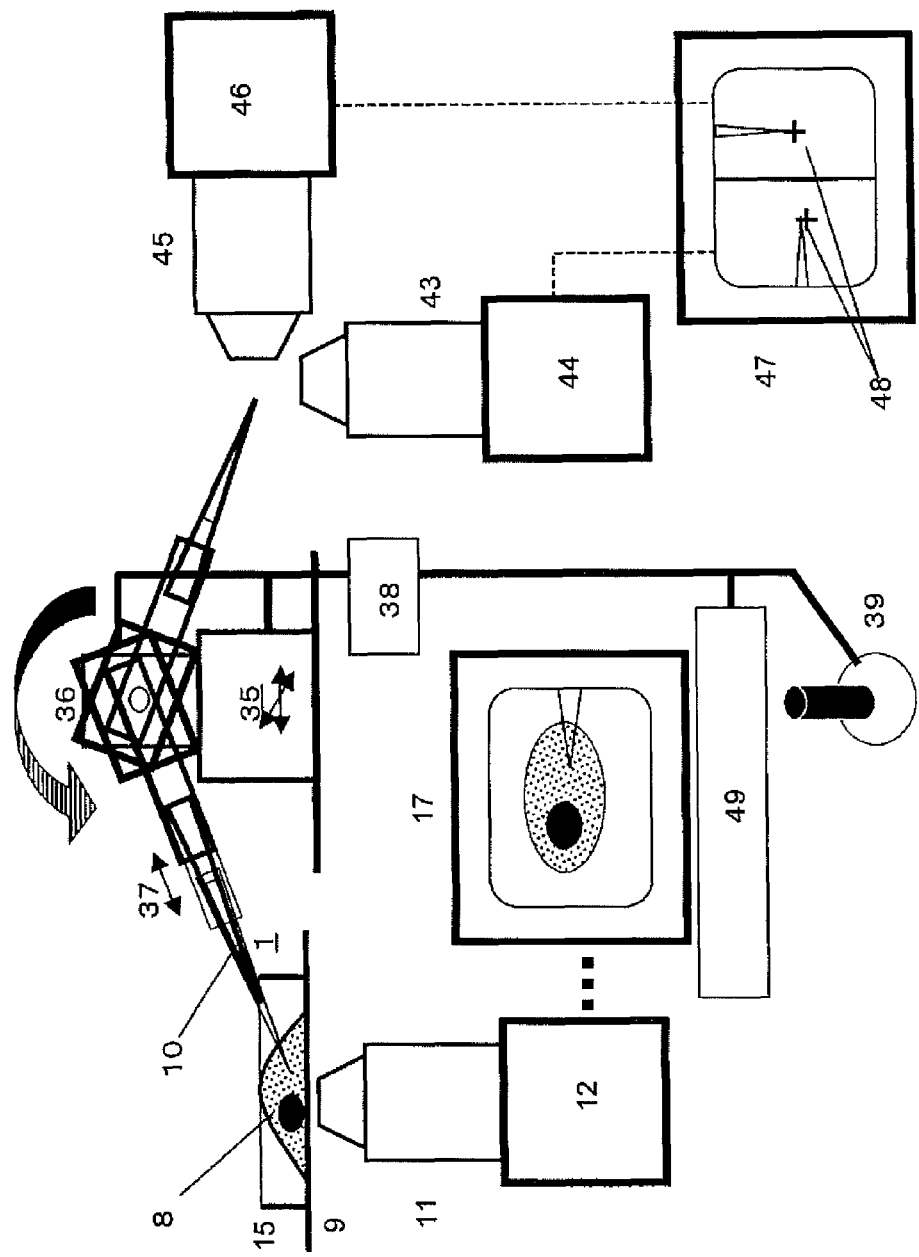

The device which is shown in FIG. 25 has been invented to solve the problem at inserting into the cell. It is extremely difficult that the forefront of the ionization capillary tip 1 is recognized under the microscope at inserting the above nanospray ionization capillary tip (ionization capillary tip) 1 into the cell 8 cultured in the Petri dish 15 on the microscope stage 9. It was found that the forefront of the ionization capillary tip was often broken and the process was the bottleneck of taking intracellular components. Then the device and method to overcome the difficulty of leading the forefront of the ionization capillary tip 1 to the predecapillaryd position of the cell 8 which is observable on the monitor 17 with the objective lens of microscope 11 and the video camera combined with 11 is shown. The ionization capillary tip is set at the greatly different position in micro region every time it is set at the top of the manipulator. The position of the forefront under the microscope is fixed at two or more positions, the three-dimensional position of the forefront 48 of the capillary tip 1 is detected on the monitor 47 by the recognized video micro devices 43-44,45-46, the position of the forefront is detected with the control device for driving 49 as the number of moving steps of the electric manipulator and in how many steps the forefront of the tip can be led near the cell observed by the microscope three-dimensionally (x-y-z) and axially is also determined by the control device for driving 49. The position of cell 8 can be detected as plane of focus from the vertical position of the microscope stage 9 or the objective lens 11 if the position is based on the microscopic field. Then the conventional device which equips the encoder with z-axis of microscope stage driving device is combined with the above leading device for the forefront of the ionization capillary tip. In this way, the position of the forefront of the ionization capillary tip can be led near the targeted cell which ioninzation capillary will be introduced or into the cell on the monitor 17, which is the most difficult step, automatically or semi-automatically. And more rapid and high-accuracy operations are developed. The other numbers are the same as the previous figure. Like that, we can overcome the difficulty of leading the ionization capillary tip 1 to the specific position in the micro region for the suction of sample with difficulty. Of course, it is possible to do the part of the processes manually because the last prick on the cell may require subtle feeling which might be serious for automation and often manual manipulation is better.

Figure 26:
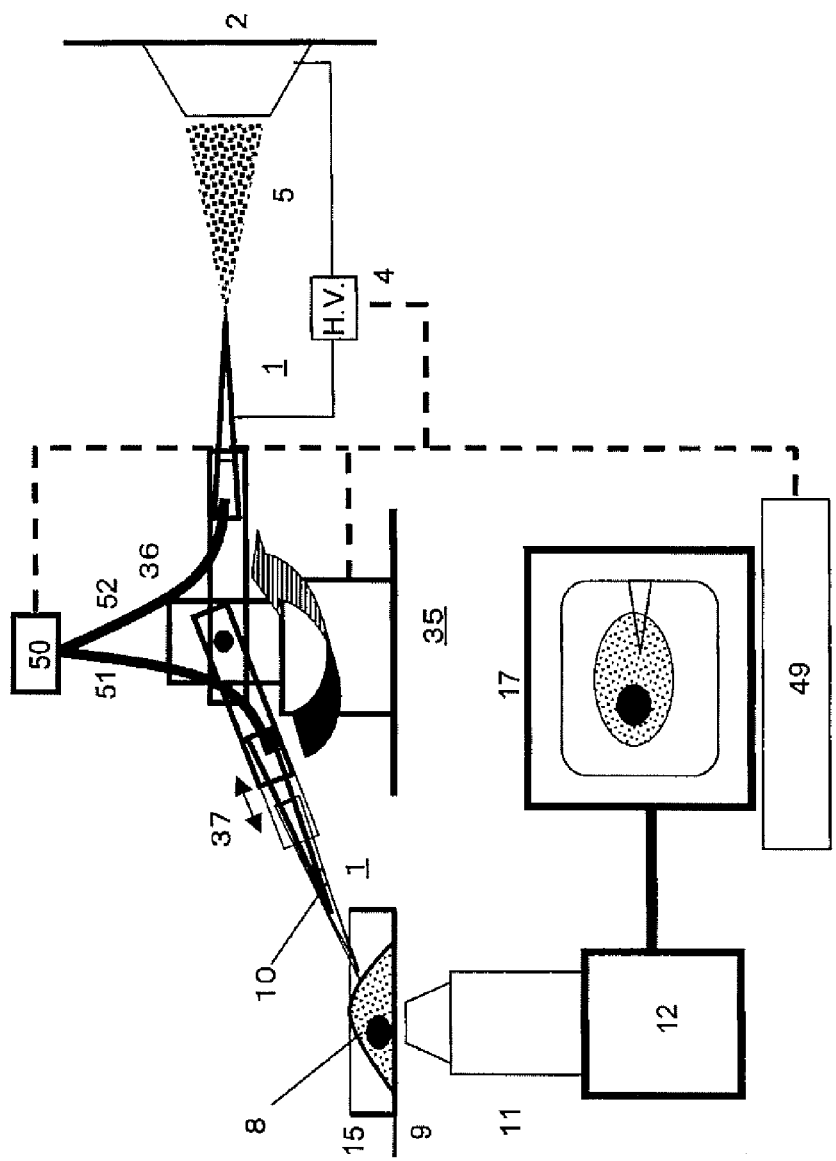

FIG. 26 additionally shows the embodiment in which the automation of the operations from the suction of the intracellular component with the ionization capillary tip 1 to introduction by ionizing the samples to the mass spectrometer by nanospray is advanced. In this case, the example is shown which provide the automation by setting the tube for suction of the sample in micro region such as cells 51 and the tube for sending the ionization supporting solvent 52 via the injection pump 50 and performing the suctions and additions of the solvent addition to the above.

Figure 27:
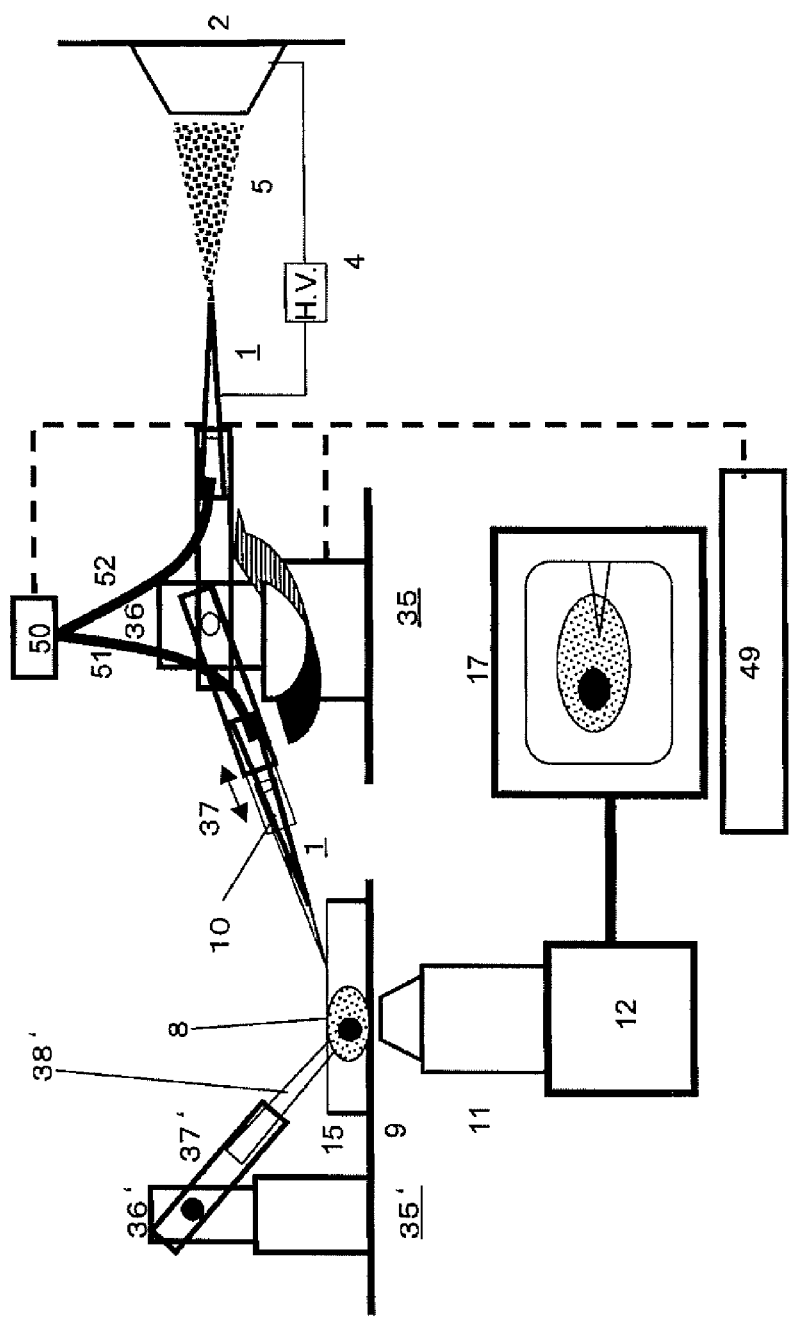

FIG. 27 is about the same as FIG. 26, but FIG. 27 is the example when the objects are the cells which are not bound to the surface of culture dish such as floating cells. In this case, the system which holds the target cell by X-Y-Z driving stage 35', angular and axially-moving actuator 36' and the control device for driving 38 of the electric manipulator which sets the cell holding capillary tip which sucked the component weakly at the top and inserts the ionization capillary tip 1 which pricks the cell into the cell by operating the forefront of the capillary tip for capturing the intracellular fluid 1 is shown. Of course, it is possible to set the ionization capillary tip whose inner surface is modified, or the capillary tip which is fabricated for smooth insert into the cell by applying hydrophobic or hydrophilic coating to the outer surface at the same time. And the systems shown in from FIG. 24 to FIG. 27 can also respond? and control of driving in the case of applying pressure inside of the ionization capillary tip not to mix the component of cellular medium during the approach of these ionization capillary tips to the cell and taking the cellular component which is the object of the mass spectrometry from the above forefront by leakage of the components in the cells or the tissues from the hole formed at the tissue containing liquid.

Figure 28:
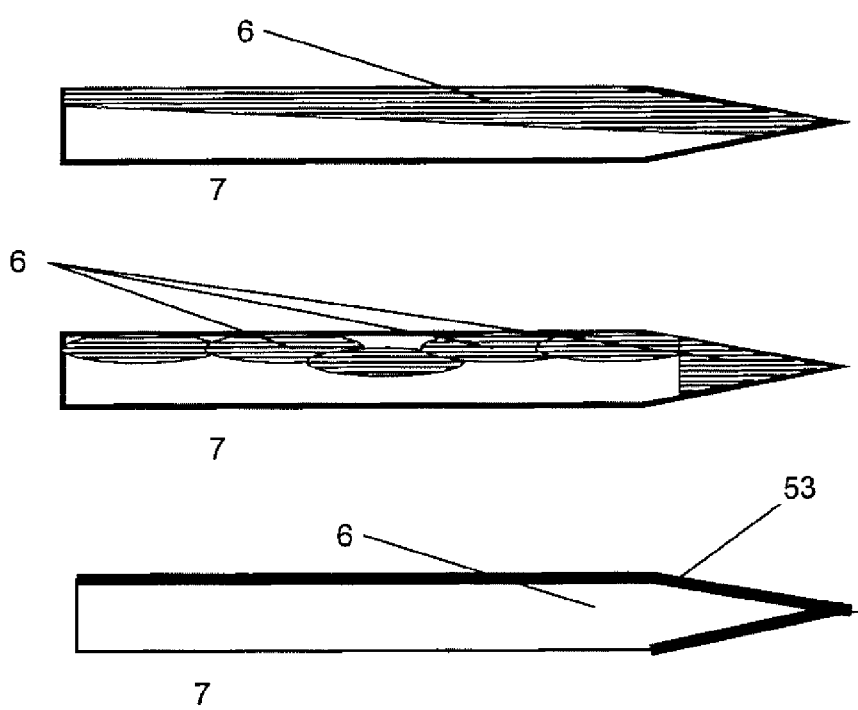

FIG. 28 shows the various conductive coatings of the surface 6 of the nanospray ionization capillary tip (It is written "the ionization capillary tip".). Basically, the nanospray can be occurred if the sharp part of the forefront is applied the conductive coating or sputtering enough because the equipotential surface like funnel is formed around the forefront space to the sample inlet of mass spectrometry. So it shows that the entire ionization capillary tip doesn't have to be applied conductive coating and conducting material 53 has only to be coated or attached from the part of contacting the external supply terminal to the forefront keeping the conductive property. For this reason, the inside of the ionization capillary tip can be made to be easily viewable and the merit of keeping the production costs down is provided.

Figure 29:
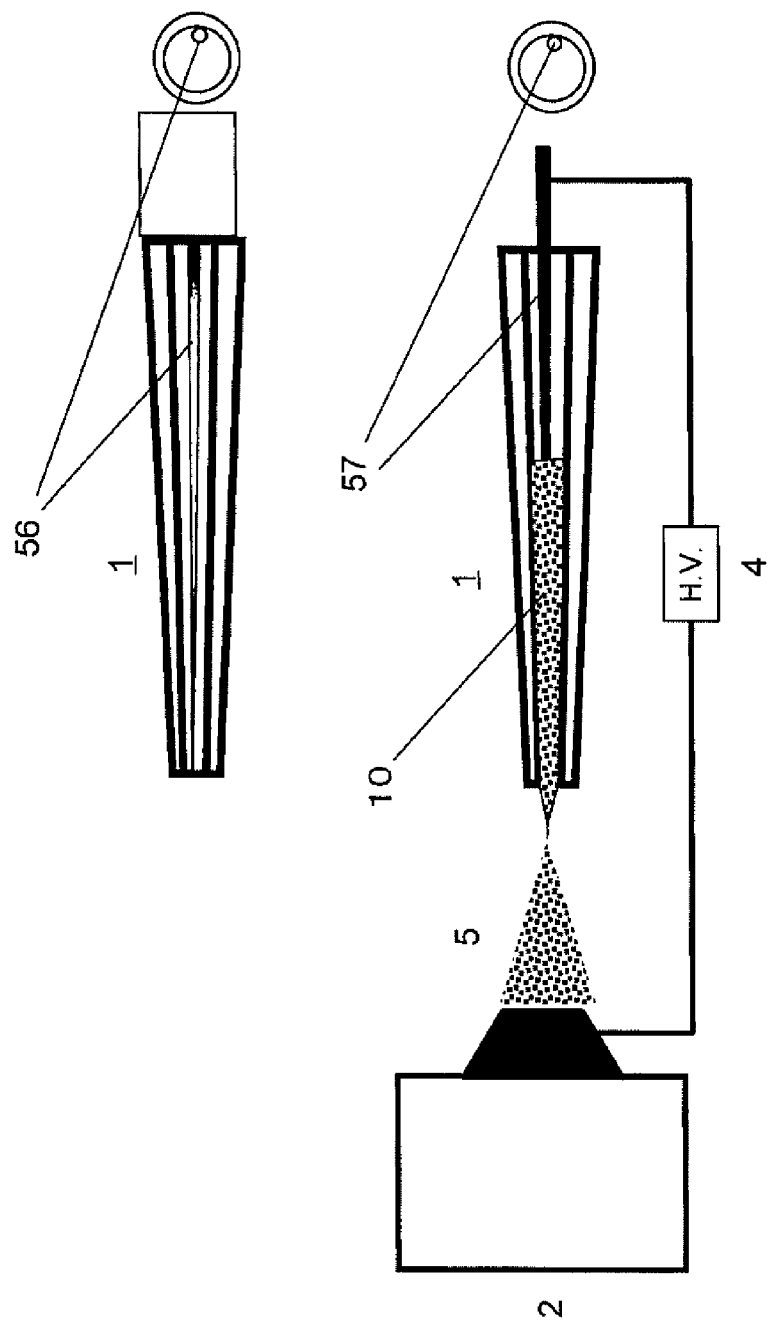
Figure 30:
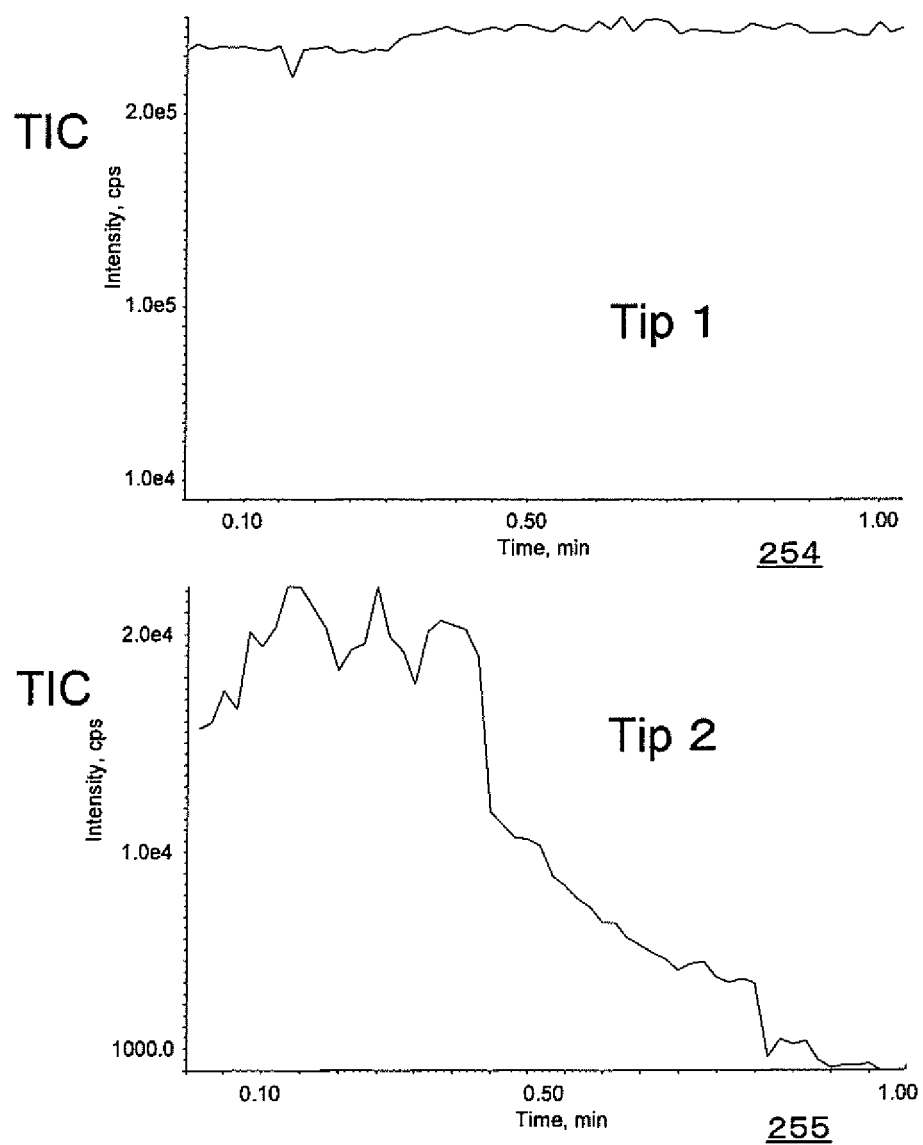

FIG. 29 shows the devisal in which the capillary material with affinity for sample solvent 56 (it is written "capillary wire for solvent pathway" below) whose surface has affinity with the fluid captured by the ionization capillary tip 1 and the ionization supporting solvent is set in the ionization capillary tip. The capillary wire for solvent pathway can be bonded to the inner surface of the ionization capillary tip with the part of the surface from the forefront to the back-end. Or the capillary wire for solvent pathway can be bonded to the inner surface of the tip partly and be hovering in other part if the capillary wire doesn't move. Optimally, it is important that the capillary wire for solvent pathway is bonded to the inner surface of the ionization capillary tip near the forefront especially, becomes capillary in the capillary forefront and don't jam the forefront. The nanospray whose TIC is stable 254 has been realized by the capillary wire for solvent pathway as shown in FIG. 30. The nanospray scarcely breaks when it is used as a general nanospray ionization capillary tip or in the case of single cell sample with high viscosity. By comparison, in the case of the ionization capillary tip without the capillary wire for solvent pathway, it was found that TIC was unstable as shown in the figure of 255 and it was often difficult to restart nanospray if the nanospray broke once. It is important to support extractions of the components in solutions and movements of solutions at the single cell nanospray ionizations like this and such improvement of the device was the another key of this method. The devisal is used as the available technology in the case of what's called nanospray tips without surface coating et al of course. And it was possible to cause more aggressive energizations and nanospray ionizations by setting the conductive capillary material 57 (FIG. 29) in the inner surface of the capillary tip 1 and applying the electrode to it.

Figure 31:
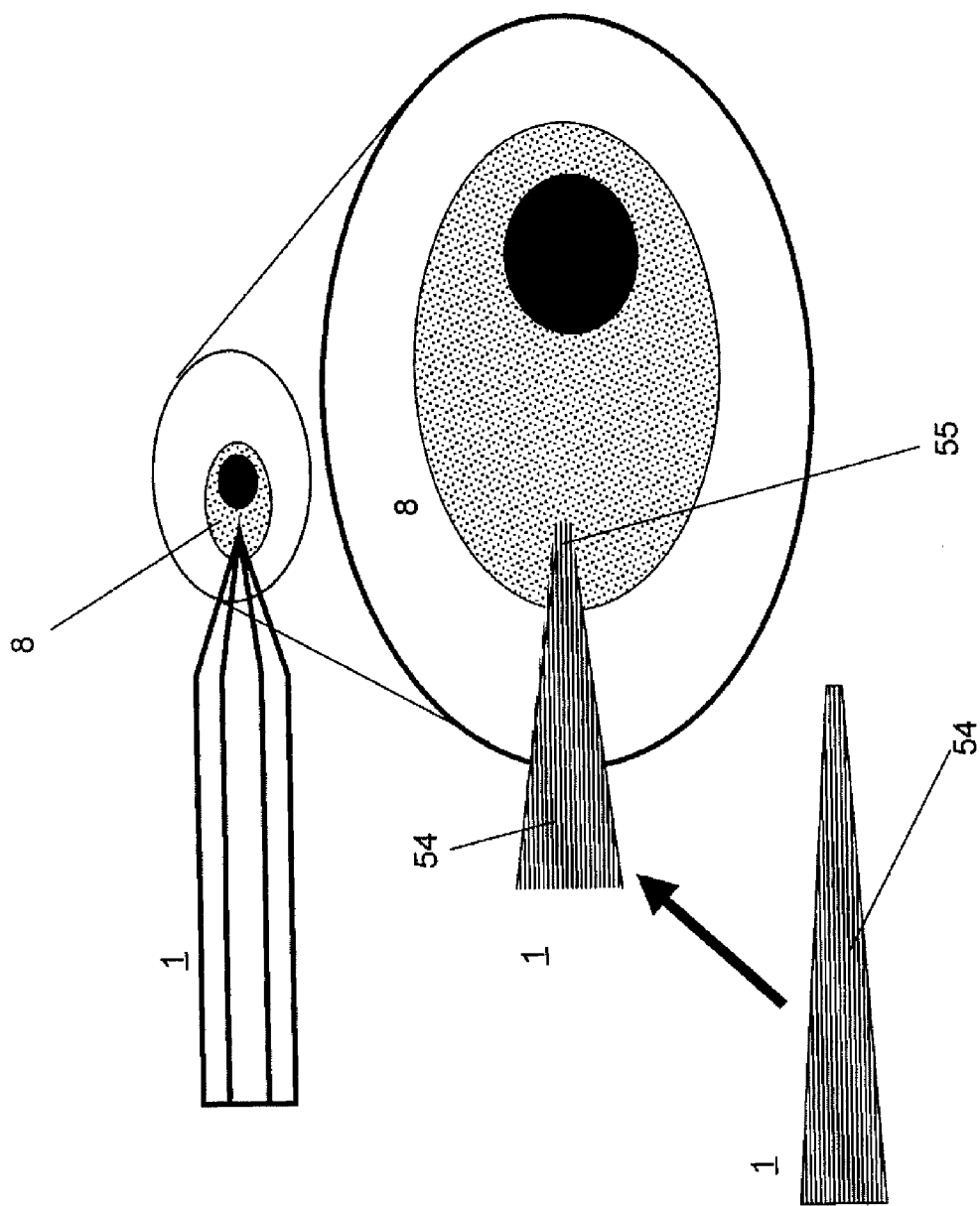

FIG. 31 shows the insert of the ionization capillary tip 1 whose outer surface is applied hydrophobic coating into the cell. The outer material surface has the property which is similar to that of the lipid bilayer, the cell membrane structure, by the coating and it was discovered that the insert became very easy while inserting the capillary tip 1 into the membrane in the case of animal cells. The coating could minimize the unnecessary reactions to the cell from the morphological changes of the cell 8 by insert of ionization capillary tip 1 and the leakage of intracellular components from the cell insert part of the capillary tip 55. In addition, the mixing of the culture fluid into the forefront of the ionization capillary tip 1 by capillarity which occurs while the ionization capillary tip 1 is moved in the cell culture fluid to the cell can be minimized by repulsion of the hydrophobic surface of the tip with water. Then it was found that the operation of introducing pressured air into the ionization capillary tip 1 to prevent the mixing of the cell culture fluid became almost unnecessary and the operation could be simplified. On the other hand, in the case of plant cells, it was found that hydrophilization of the surface of ionization capillary tip 1 was also available because the part of cell walls consists cellulose components.

The term "the hydrophilic surface" can be the material of capillary tip which are applied the hydrophilic materials physically or which are chemically combined with the hydrophilic compounds directly or with spacer. The hydrophilic compounds include protein molecules, nucleic acid molecules, sugar molecules and their complexes which are present in living body and whose molecular surfaces are hydrophilic, and the protein molecules whose molecular surfaces are hydrophilic include various enzymes, cytokine, peptide hormones, antibodies, acceptor proteins, acceptor agonist, acceptor antagonists, acceptor inhibitor, ion channel proteins, channel blockers and enzyme inhibitor, but are not limited to. The nucleic acid molecules whose molecular surfaces are hydrophilic can be DNA single strand, RNA or their combinations. And the range from several to several thousand bases is acceptable as the number of the base sequence. The material of capillary tip which is chemically combined with these the proteins whose molecular surfaces are hydrophilic and/or the nucleic acids whose molecular surfaces are hydrophilic and/or the sugar molecules whose molecular surfaces are hydrophilic are available. The hydrophilic materials include hydroxyl group and/or thiol group and/or ether and/or thioether and/or anionic and/or cationic highly-polar functional groups. Anionic functional groups include carboxyl group, sulfonate group, sulfate group and phosphate group but are not limited to. Cationic functional groups include amino group, aminoethyl group, dimethylaminogroup, trimethylamino group, guanizide group, imidazolyl group and aminobenzyl group but are not limited. And it is possible to perform nanospray ionizations with the mixture of the ionization supporting solvent and the eluting solvent and measurement by combining the affinity groups with the surface of magnetic beads, performing the component-specific captures in the sample and leading the magnetic beads for capture of molecules to the forefront of the ionization capillary tip by the magnet. The hydrophobic surface can be the material of capillary tip which are applied the hydrophobic materials or which are chemically combined with the compounds which have hydrophobic functional groups directly or with spacer. Hydrophobic materials include aliphatic hydrocarbons, aromatic hydrocarbons and fatty acid esters but are not limited to. Hydrophobic functional groups include octadecyl group, dodecyl group, hexyl group and phenyl and naphthyl group which have substituent groups but are not limited to.

Figure 32:
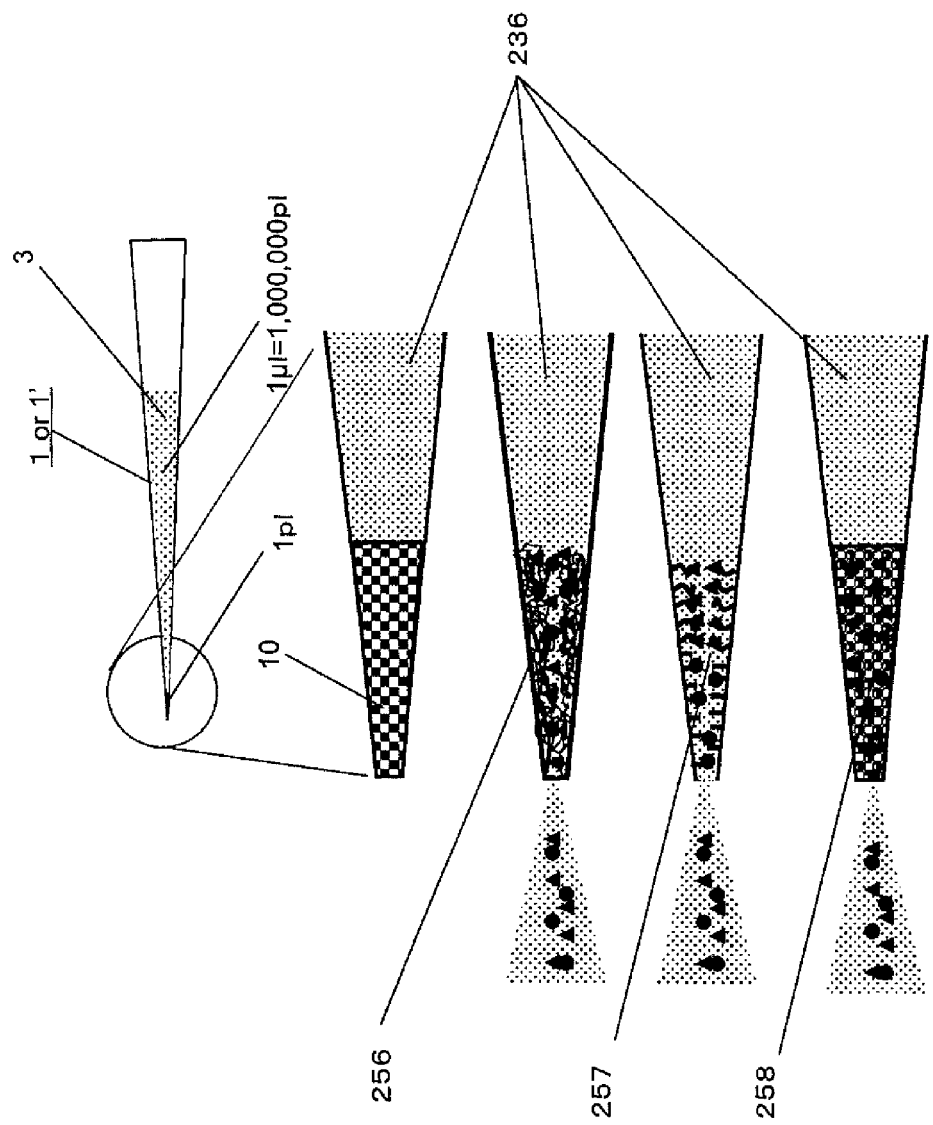

FIG. 32 shows why single cell components can be detected by taking the samples with the nanospray ionization capillary tip (ionization capillary tip) 1 even though the cellular components are taken at ultralow volume like this. If the volume of a single cell is assumed to be about 1 picoliter, the cellular component is sucked and captured in the slight part of the forefront of the nanospray tip. If the ionization supporting solvent 236 is added by 1 microliter and mixed well, the cellular component is diluted about a million times and then it can not be detected because the concentration is far below the detection sensitivity of any present mass spectrometer. It is thought that this is why the direct analysis of single cell has not been realized even though many researchers probably had tried until now, as we have experienced. We invented that it was possible to detect the molecules in ultralow volume samples like this by using the ionization supporting solvent and its flux by the nanospray to elute the components in the cell sample fluids with keeping the cellular components at the forefront in high concentration even though the cellular components themselves were in minute amounts.

Therefore, various condition settings to keep the cellular components at the forefront of the ionization capillary tip 1 or 1' hold another key of this invention. In this invention, the ionization supporting solvent high in organic solvents 236 is used in low molecular analyses after the captures of the cellular components at the forefront. We think that high molecular components, especially such as protein components become deposited and adhere to the inner surface of the capillary tip and low molecular components are eluted in the nanospray in a way that the supporting solvent elutes the small components from the high molecular matrix 256. Therefore, it was thought that modifying the inner surface of the forefront by the groups with molecular affinity selectively, capturing the components in intracellular components specifically by the groups with affinity 257 and eluting with ionization supporting solvent 236 was one method to enable the single cell analyses. And it was thought that setting resins or mesh with molecular capturing affinity (such as affinity, ion exchange, hydrophobicity, bivalent ion affinity) on the inner surface of the forefront and eluting with ionization supporting solvent 236, and previously described gradient elution is one method, too.

Figure 33:
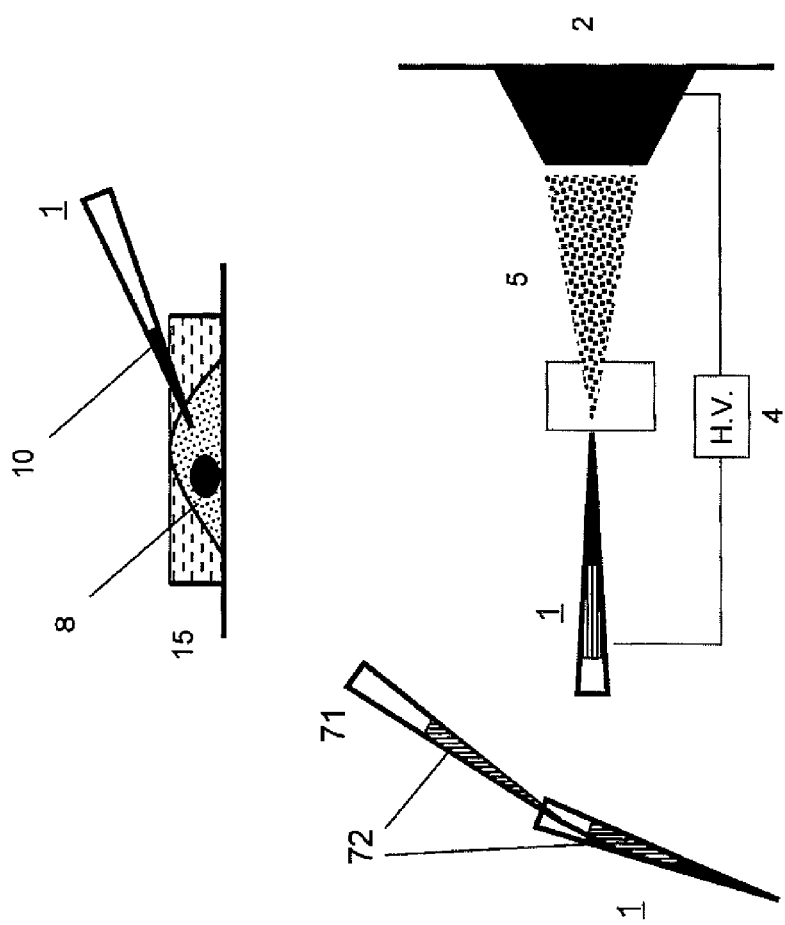

With the above devisal, the process to take the contained fluid 10 of the cell 8, add the eluting solvent or the ionization supporting solvent or their mixture to the sample fluid taken at the forefront of the ionization capillary tip 1 from the back-end of the ionization capillary tip 1 softly and then perform nanospray ionization as shown in FIG. 33 was employed. Of course, gradient elution is also possible by adding the solvent which has different solvent composition after that and mixing it with the previous solvent partly.

Figure 34:
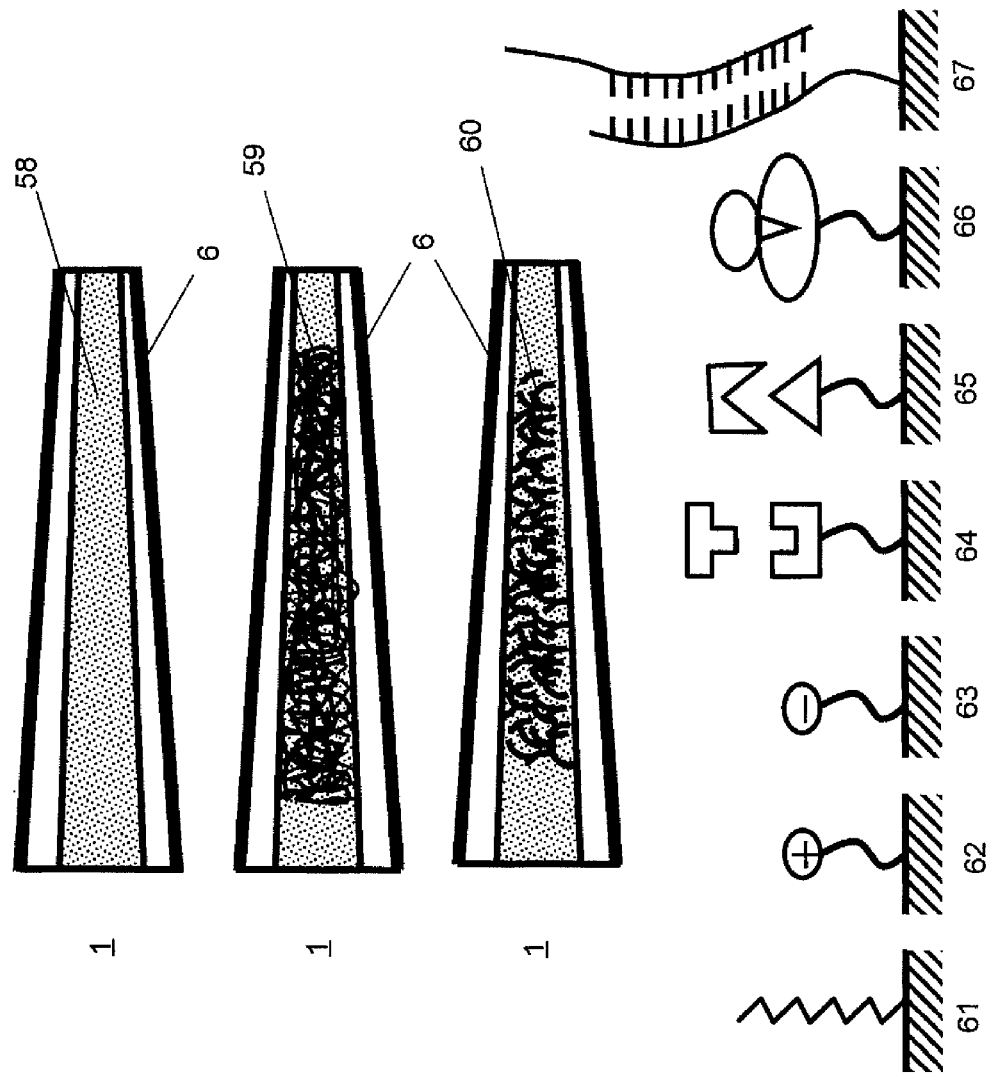
Figure 35:
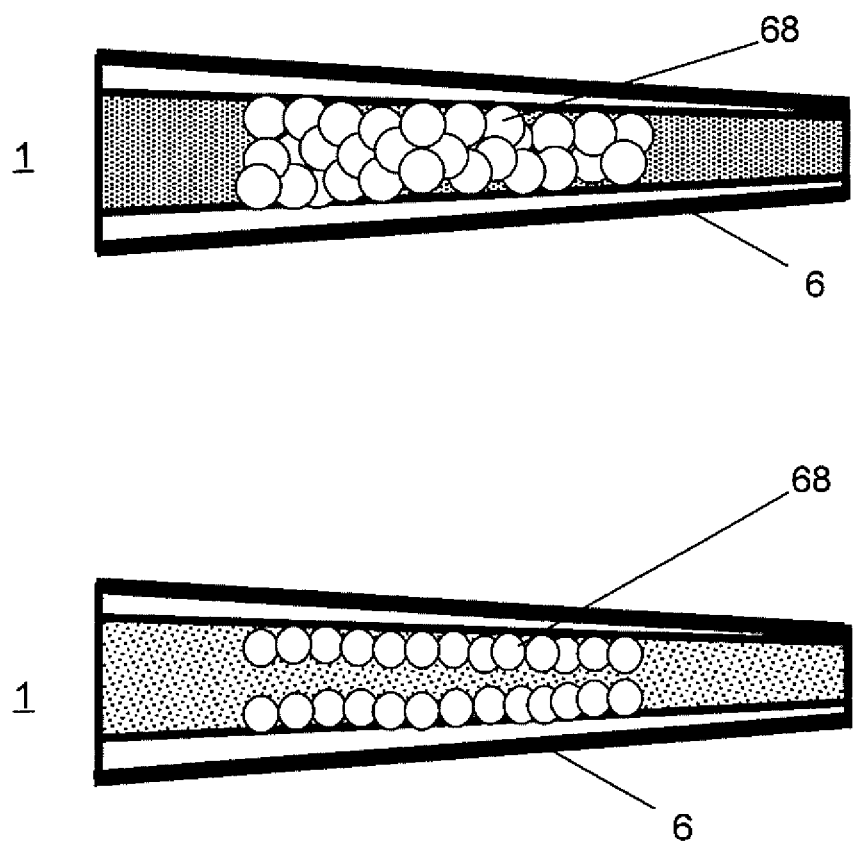

FIG. 34 shows the various methods of modification for inner surface of the forefront of the nanospray ionization capillary tip 1. It is possible to apply surface binding substance or coating of hydrophobic substances 61 or surface binding substance or coating of cationic substances 62 or surface binding substance or coating of anionic substances 63 or binding surface of receptor of antibody etc 64 or binding surface of antigen or substrate 65 or homogenous coating of inner surface 58 provide binding surface of enzyme etc. 66, or form binding surface of nucleic acids 67. Or It is possible to fill the inside with fibrous or chainlike packed materials 59 or monolith structure or cover the inside with brush like surface-bound material and bind the above modifying molecules on them. Or it is possible to coat or combine the inside with temperature-responsive polymers recently-reported. In this instance, selective detection of molecular groups can be achieved with high sensitivity by capturing the cellular component with fibrous or chainlike packed materials 59 which have molecular affinity after the suction of the component from the forefront of the ionization capillary tip 1, washing out by suction from the forefront of the ionization capillary tip 1 or injection from the back-end of the above capillary tip of the solution for washing out the components except the object of analysis after that, performing desalination of the salts preventing the ionization, introducing the ionization supporting solvent to elute the captured components from the back-end of the ionization capillary tip 1 after that. FIG. 35 shows the example of packing or arrangement like ring of resins which have the molecular affinity groups on their surface 68 in the ionization capillary tip 1 at the inside of the forefront. Selective concentration of molecular groups and desalination can be performed by washing and elution same as above description. More efficient concentration of molecules is enabled by modification of the inner surface of the capillary tip 1 like this. The inner surface modified zone can be the entire surface of the inside of the tip because the cellular component fluid is captured only at the forefront, however, optimally on the above account, it is preferable that the zone is the limited part near the forefront and it is used depending on purposes and circumstances. Such a inner surface modified ionization capillary tip should be applied hydrophobic or hydrophilic coating on the outer surface and processed to be inserted into the cell smoothly, and we should be careful to prevent the components of the cellular medium being mixed into the forefront by increasing a pressure of the inside of the ionization capillary tip, of course. And the nanospray ionization capillary tip which is combined with molecular affinity groups on the inner surface of the forefront is useful to capture specific components by the forefront of the ionization capillary tip when the cellular components which are the object of the mass spectrometry are taken from the above forefront by leaking the components in the cell or the tissue from a pinhole formed at the tissue containing fluid.

FIG. 35 shows the example of packing resins for chromatography inside as an example of modification of inside. The surface of the resins can be modified with the molecules shown in the bottom of FIG. 34. It will become easy to provide elution by ionization mediated ejection of concentrated components? at the spray at the same time as the suction of the fluid by arranging the resins only along the inner wall because the components in the cell or the micro region are sucked and captured in the ionization capillary tip 1 in the method. The method to combine these hydrophobic or hydrophilic functional groups with capillary tip materials chemically and directly or with spacer and the applications of chromatography using it are described in the text book "Partner of Analytical Chemistry" Ed. Tsutomu Masujima et al, p172-191 (2007), for example. And the applications of the chromatography using packing materials are described in p145-172 in the same book, for example.

Here is the method: The resins 68 is set on the frit material 69 without fixing shown as FIG. 36 to suck up the intracellular fluid and prompt the absorption of the fluid on the surface of the resins. After the suction of the cell fluid 10, solution for capture of molecules 70 is sucked additionally and then the components in the cell or the micro region are combined with the surface of resins and concentrated. After that the mixture of eluting solvent and ionization supporting solvent 72 is added from the micropipette 71 and then the sample is ionized by the nanospray 5. This method is available when we trace the known molecules by highly-sensitive mass spectrometers such as tandem quadrupole because the intracellular fluid is diluted slightly.

Figure 37:
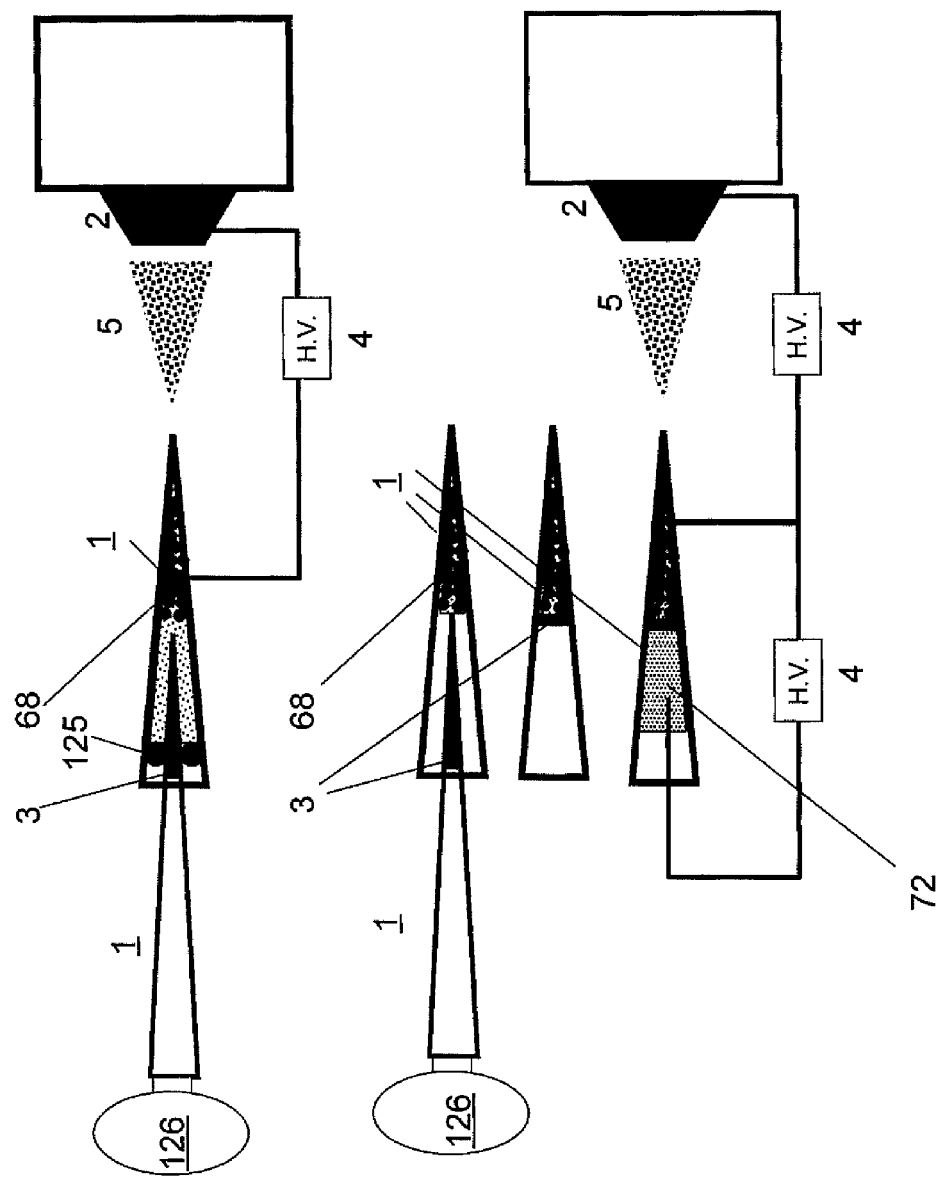

FIG. 37 shows an example of the analytical method in or out of cell using commercial nanospray tip of resin packing type. The tip which captures the intracellular component from the cell need not be processed to be conductive and the micro capillary is available. The captured sample is added on the packed resin layer by the tip and the nanospray is provided by using the ionization supporting solvent as mobile phase and the separation is caused. However, this method was impossible by a single cell. It needed several thousands of cells. It is thought that the reason why the sensitivity can not be increased is the dispersion of the component molecules to the micro packed resins.

Figure 38:
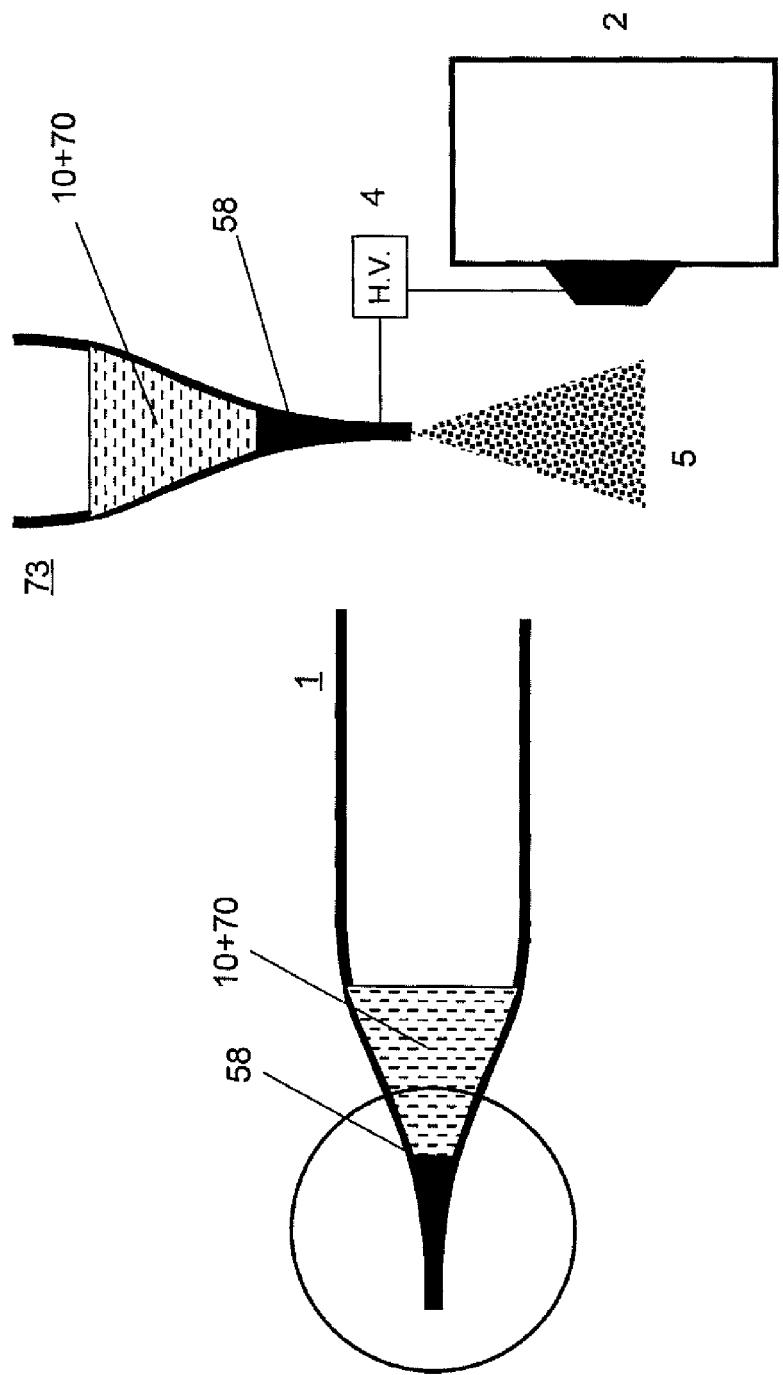

The example of performing the example in FIG. 37 by well type nanospray is shown in FIG. 38. In this instance, the coating on inner surface 58 is applied near the forefront and the well is formed for concentration near the forefront. The figure shows that the molecules are concentrated at the forefront once in the mixture of the captured intracellular fluid 10 and the solution for capture of molecules 70 and after that ionized by nanospray of the mixture of the suitable eluting solvent and the ionization supporting solvent additionally like this.

Figure 39:
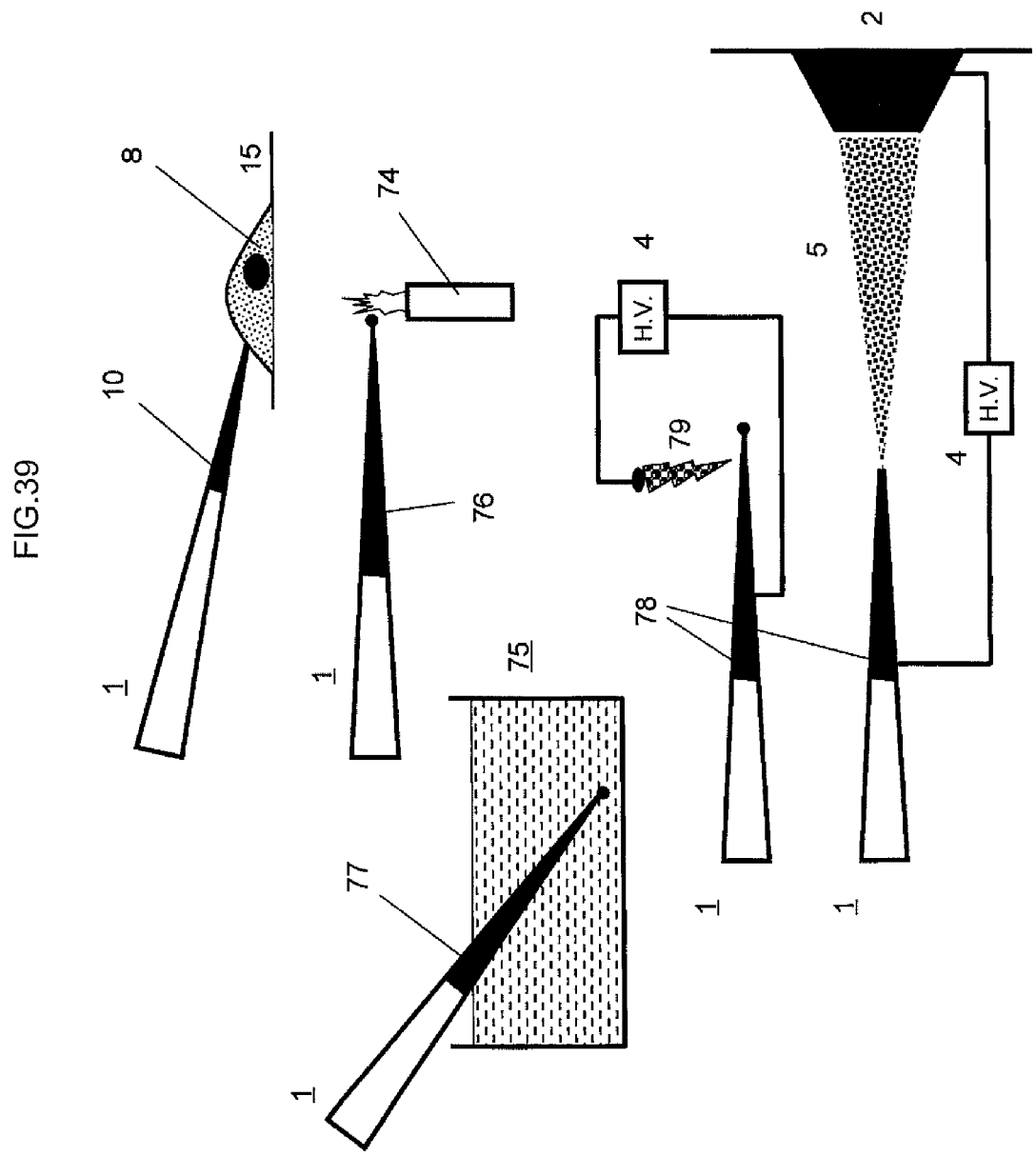

FIG. 39 shows the process of detecting of nucleic-acid components in the intracellular fluid such as RNA by amplification. It shows that the intracellular fluid 10 captured in the ionization capillary tip 1 is added the addition test solution for treatment 76, the forefront of the capillary tip is sealed by the burner et al 74, the capillary tip is soused in the hot bath (thermal cycler in the case of PCR) 75 and done the treatments such as PCR amplification and thermal denaturation 77, and then the sample fluid which was treated such as PCR amplification and thermal denaturation 78 is introduced into the mass spectrometer by nanospray after the forefront of the tip is broken with the method such as discharge 79.

Figure 40:
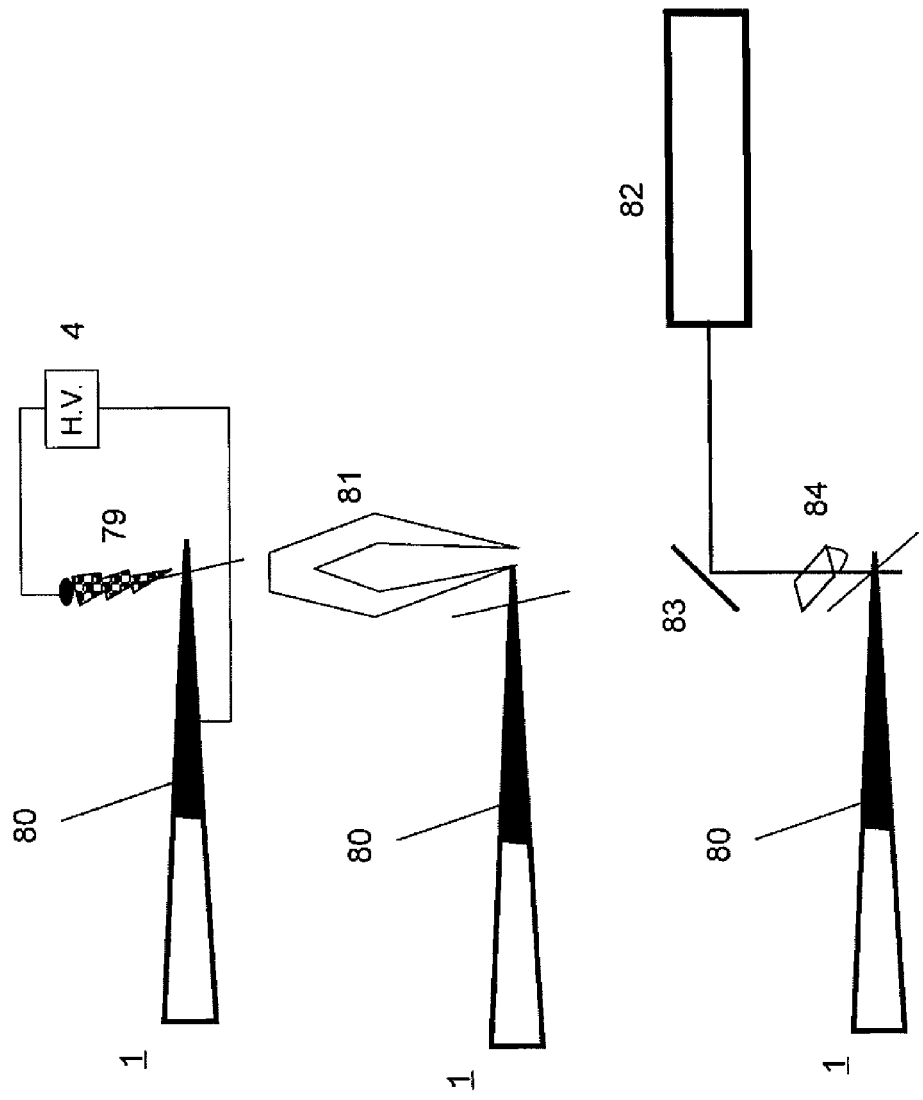

FIG. 40 describes how to treat the plugged capillary tip during samples preparation in various kinds of capillary tips (1) indicated above. The capillary tip which includes captured sample solution such as cell solution with added elution-ionization solvent as a sample, can keep nanospray ionization if plugged end is broken by discharging, is physically broken using a forceps et al, or cut by laser irradiation to enlarge the bore size.

Figure 42:
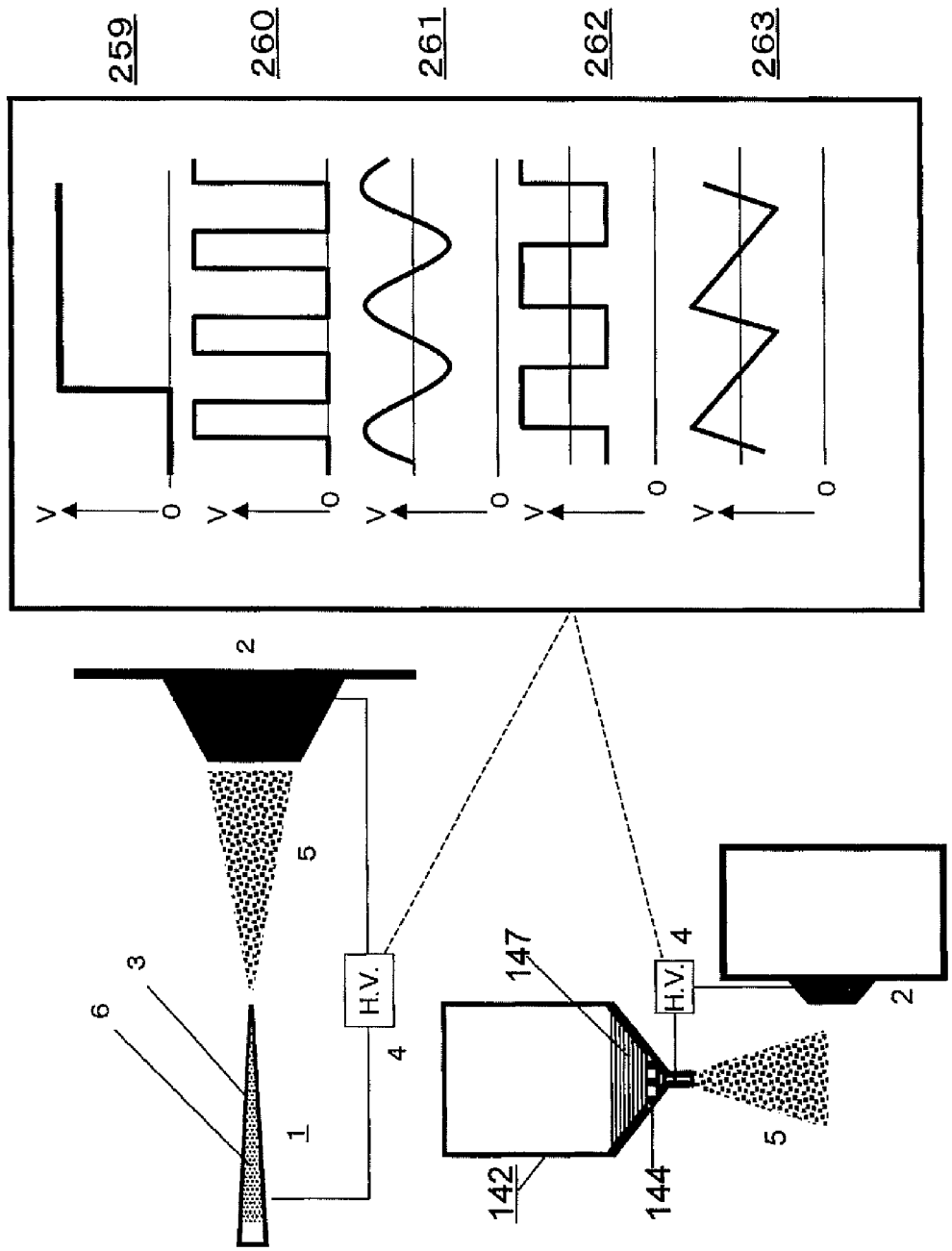

FIG. 42 shows an improved ionization capillary tip which is used for suck content solution from micro-region such as a cell. Sucking manipulation become easier by this improvement. Ionization capillary tip (1) is used by attaching it to special holder formerly. However, this method use an apparatus which includes a sleeve similar to an injection needle that fits to forefront of injection syringe. The sleeve is formed by injection molding et al in the latter edge of this ionization capillary (105). This kind of composition allows the direct use of accessories used for conventional medical syringes. For example, the tubing of 106 combines the nanospray tip 105 and the piston syringe for suction (41) or suction pump via the tube set 106 which combines them without vibrant transmission. Sucking of intracellular components can be achieved without vibrant transmission to the forefront of the needle in the micro region. And the holder is a simple clip style like 107 which enables constant positional accuracy of attaching by the position of the sleeve 105. The clip holder also enables the electric endounter with the nanospray tip 105 and enables easily providing the high-voltage electric field application.

FIG. 42 shows the various applied voltages in nanospray ionization of single cellular components by this invention. Direct current-high voltage 259 is conventionally applied between the ionization capillary tip and the sample inlet of the mass spectrometer. To improve the efficiency, we apply pulse voltage of high-voltage 260 or sinusoidal voltage overlaid with high-voltage direct bias 261. Or rectangular wave voltage overlaid with high-voltage direct current bias 262, or saw tooth-waved voltage-overlaid high-voltage direct bias 263 can be also applied.

Figure 43:
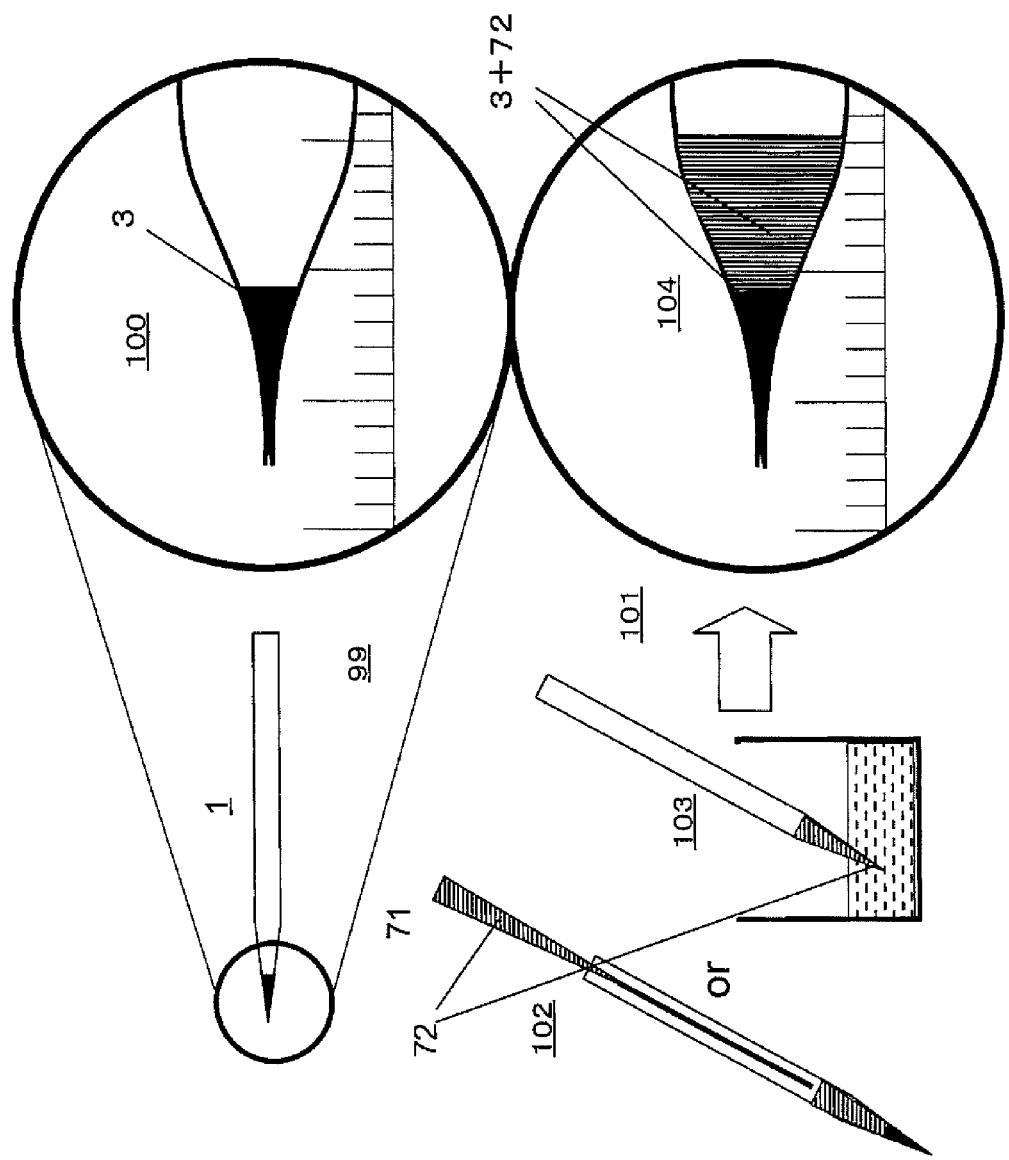

Further issue of this method for ensuring quantitative capability remained to be solved that the captured cell fluid is very small, and the volume of it can not be measured even by weight. FIG. 43 shows one example of the solutions.

The captured volume of intracellular fluid 3 sucked in the forefront of the capillary tip 1 is enlarged as a video-microscopic image. Then two-dimensional image is rotated to estimate the volume of it by three-dimensional integration. Afterwards, dilution rate can be obtained incase of addition 102 or suction 103 of other solutions.

Figure 44:
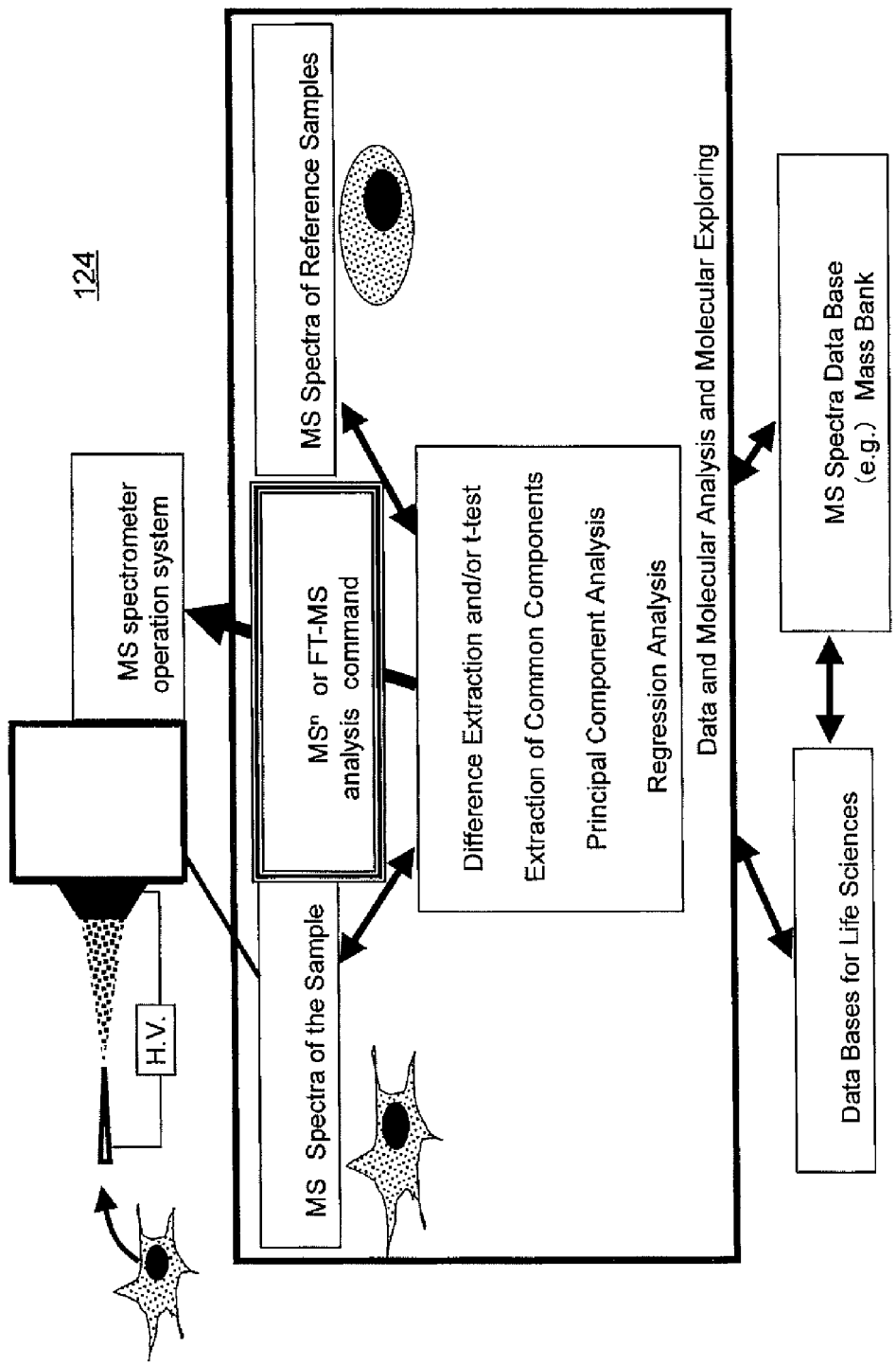

FIG. 44 shows the integration of preferred processes of data analyses in proceeding this method 124. There is no example that conventional statistical methods is used for such factor analyses between single cell states, and there is no previous these applications of differential analyses, t-test, principal component analysis and regression analyses applied to single cell mass spectra. These have made it possible to make extraction of every cell-specific molecular peaks, attribute analyses, composition analyses and to clarify functional dependence and so on.

In addition, we invented some function which was not previously included in the control system of mass spectrometer and data analysis system. Which means that: Nanospray period of very small amount of samples are very short such as five to 10 minutes as long. To identify as much molecules as possible by MS/MS in this period, we take mass spectrum of whole range in initial one minute, simultaneously make comparative statistic analysis such as t-test as a background work in the computer. In the remained latter period, automatically present or proceed information following our judge. This invention enables real-time MS/MS analyses for molecular identification, and quick high-resolution mass spectrometry with powerful ability of molecular identification.

The function of the software includes quick simultaneous internet access, public MS bank database search of automatically converted database-formatted spectrum and search result acquisition.

Figure 45:
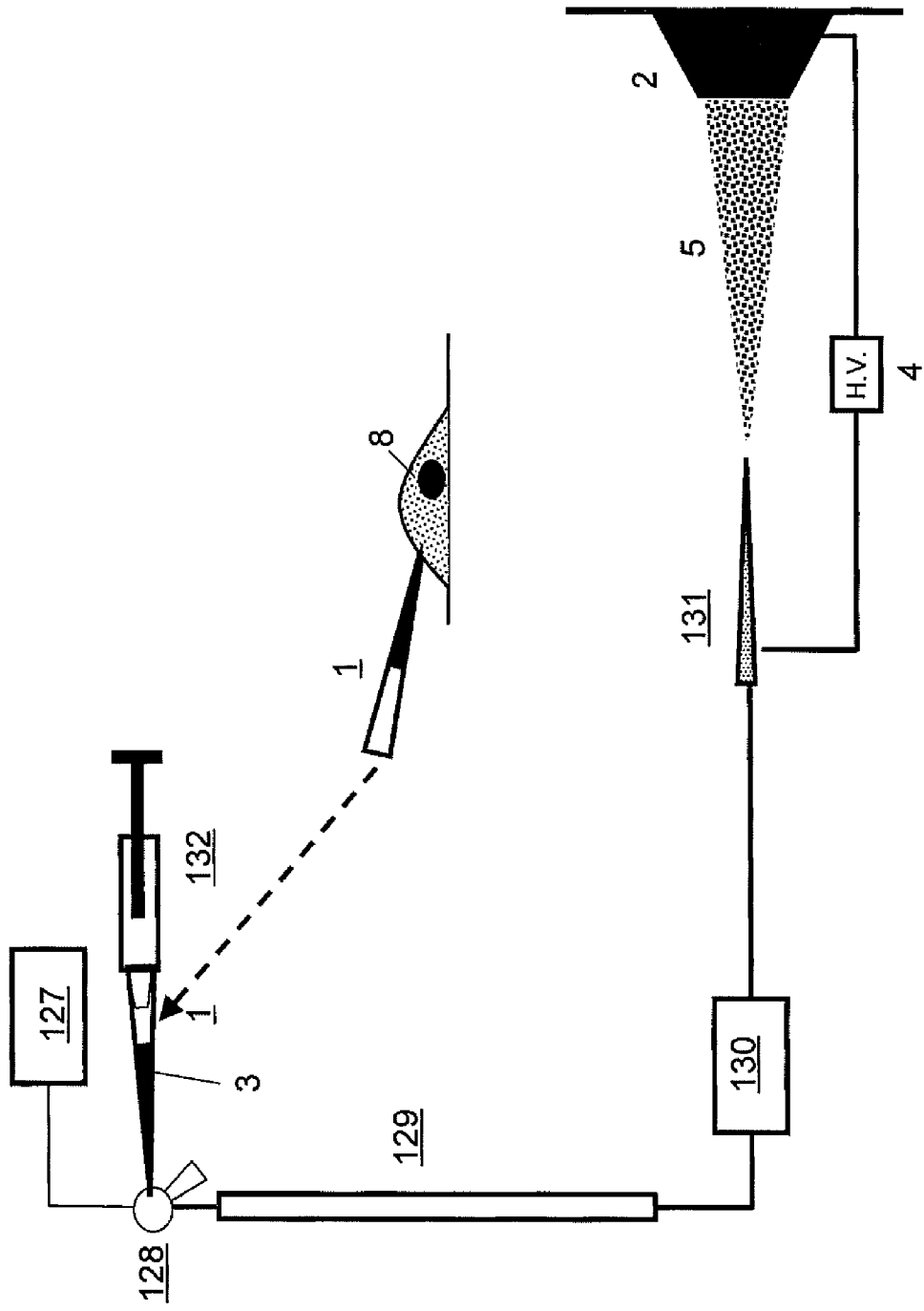

FIG. 45 shows direct injection from the ionization capillary tip 1 (It should not be conductive in this case.) into sample injector of nano liquid chromatography (LC) 128 after capturing the intracellular component in it, separation with nano LC column 129, detection by UV 130 et al, and ionization and detection by nanospray ionization. By this method comprehensiveness is improved, but this analytical method is cost-consuming because the separation column for nano LC is expensive and easily deteriorated. And this is not real-time analyses and it is necessary to set the mass spectrometer to high sensitivity for these analyses because the extremely small amount of components are scattered and lost in broad separation space.

Figure 46:
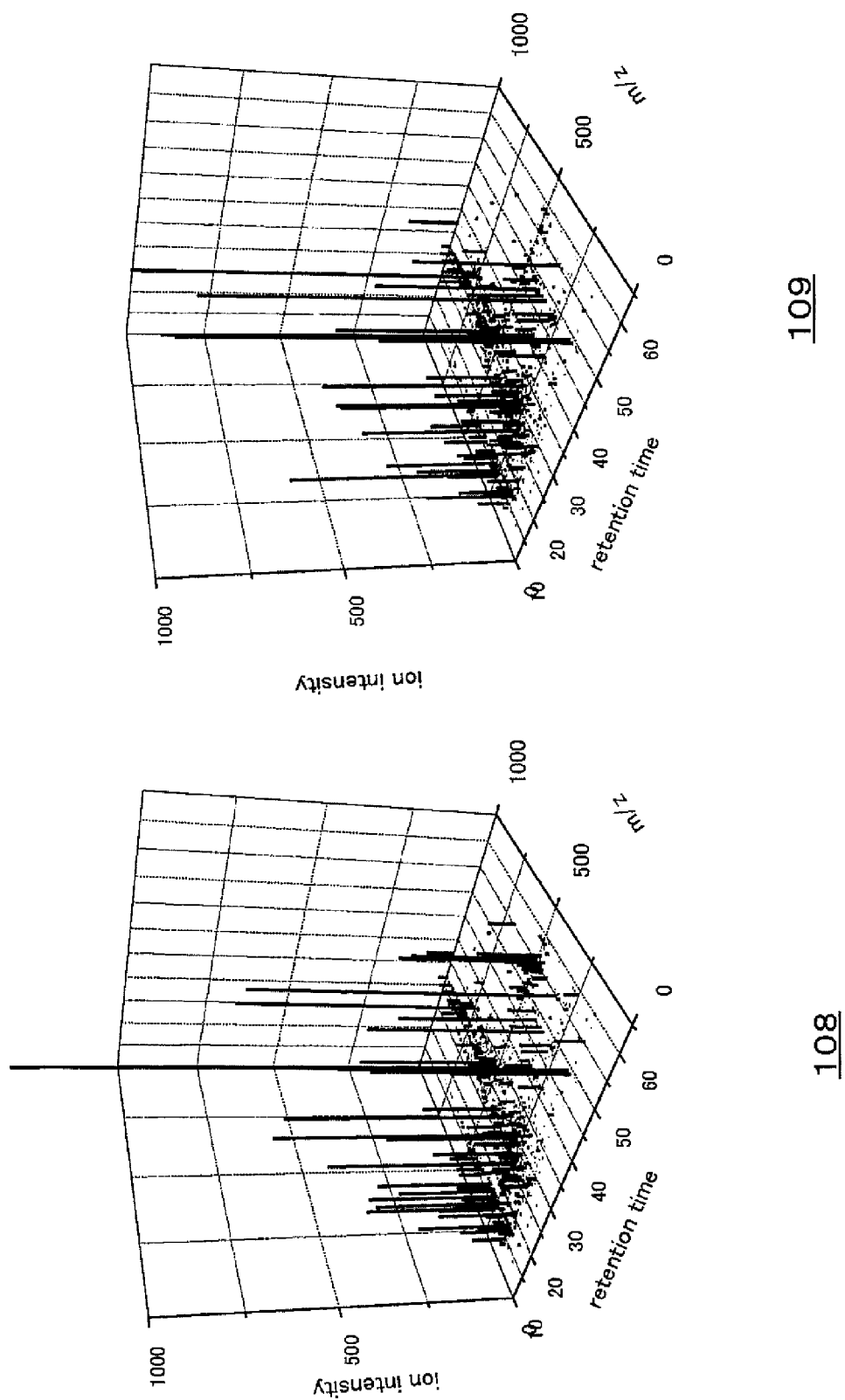

FIG. 46 shows one example of the results achieved like this. They are three-dimensional mass spectra obtained from the lymphoid cells before 108 and after 109 steroid treatment after simple separation. Existence of about 1200 peaks means that at least several hundreds of molecules are detected.

The peaks specific to one state can not be realized directly from FIG. 46, but it is indicated that 31 decreased peaks (110) appeared in FIG. 47 with t-value of over 95% after treatment by applying t-test to all of the spectra of the two state. And it is shown that the 20 peaks increased after treatment (111), which have t-value below −95%. This method enables to extract peaks with increase or decreased amount between two cell states, that is the extraction of differential molecules among different condition, to increase the comprehensiveness of the future intracellular molecular kinetic analyses.

Figure 48:
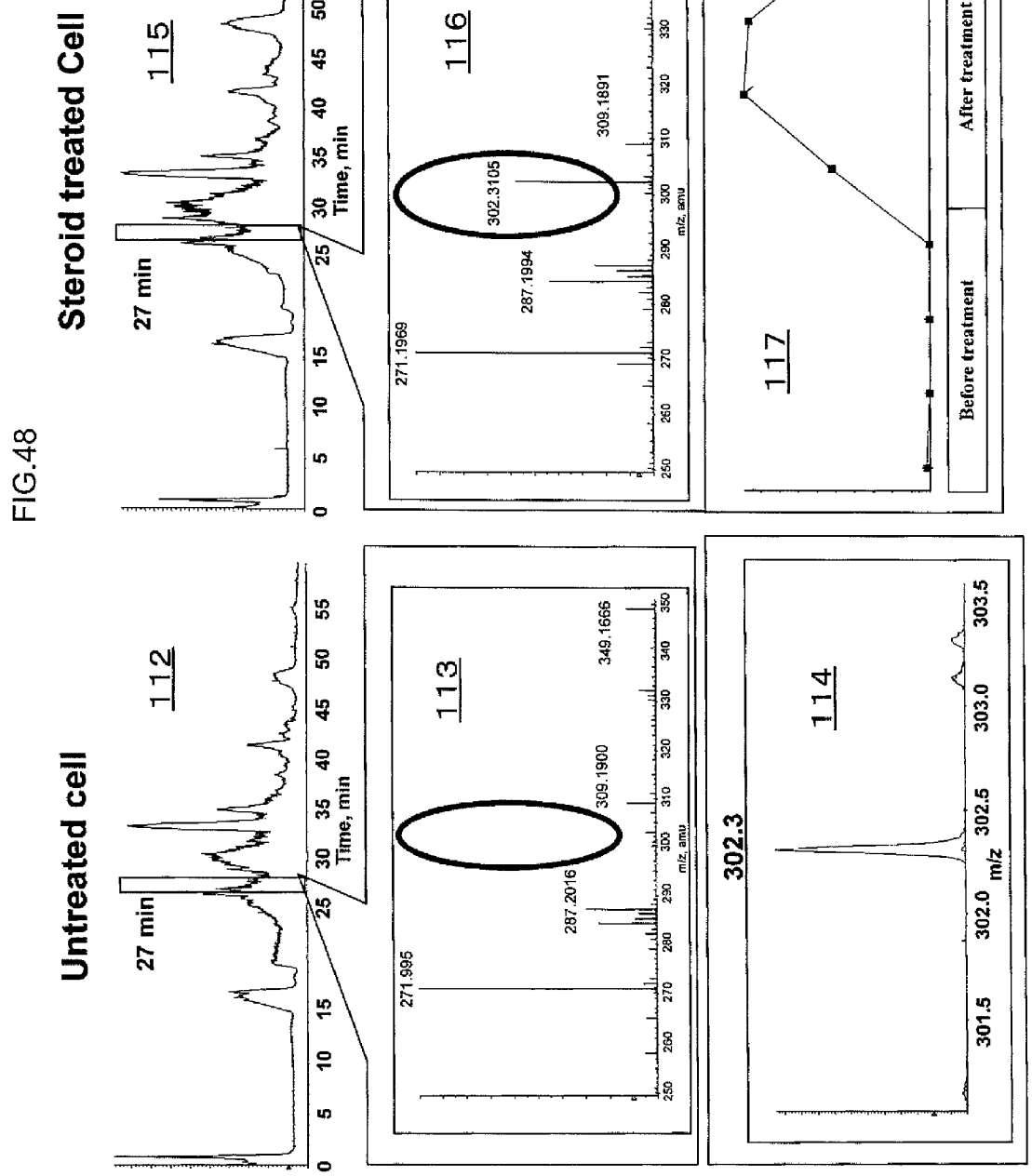

In FIG. 48, the peak of m/z 302.3 is chosen as a representative of these peaks and the peak intensity of untreated cell and cell after treatment are compared. Graph 112 and 115 indicates total ion chromatograms. In these chromatograms, the spectra of the retention time when the peak of m/z 302.3 appears are compared. The peak which is not detected in the spectrum 113 appears in the spectrum 116 after treatment.

The intensity of this peak in each sample is plotted in FIG. 117 showing that the intensity is certainly increased in every sample. In addition, the peaks are actually observed after treatment by comparison of FIG. 113 and FIG. 116, too. The peak of m/z 302.3 is the enlarged in FIG. 114.

Figure 49:
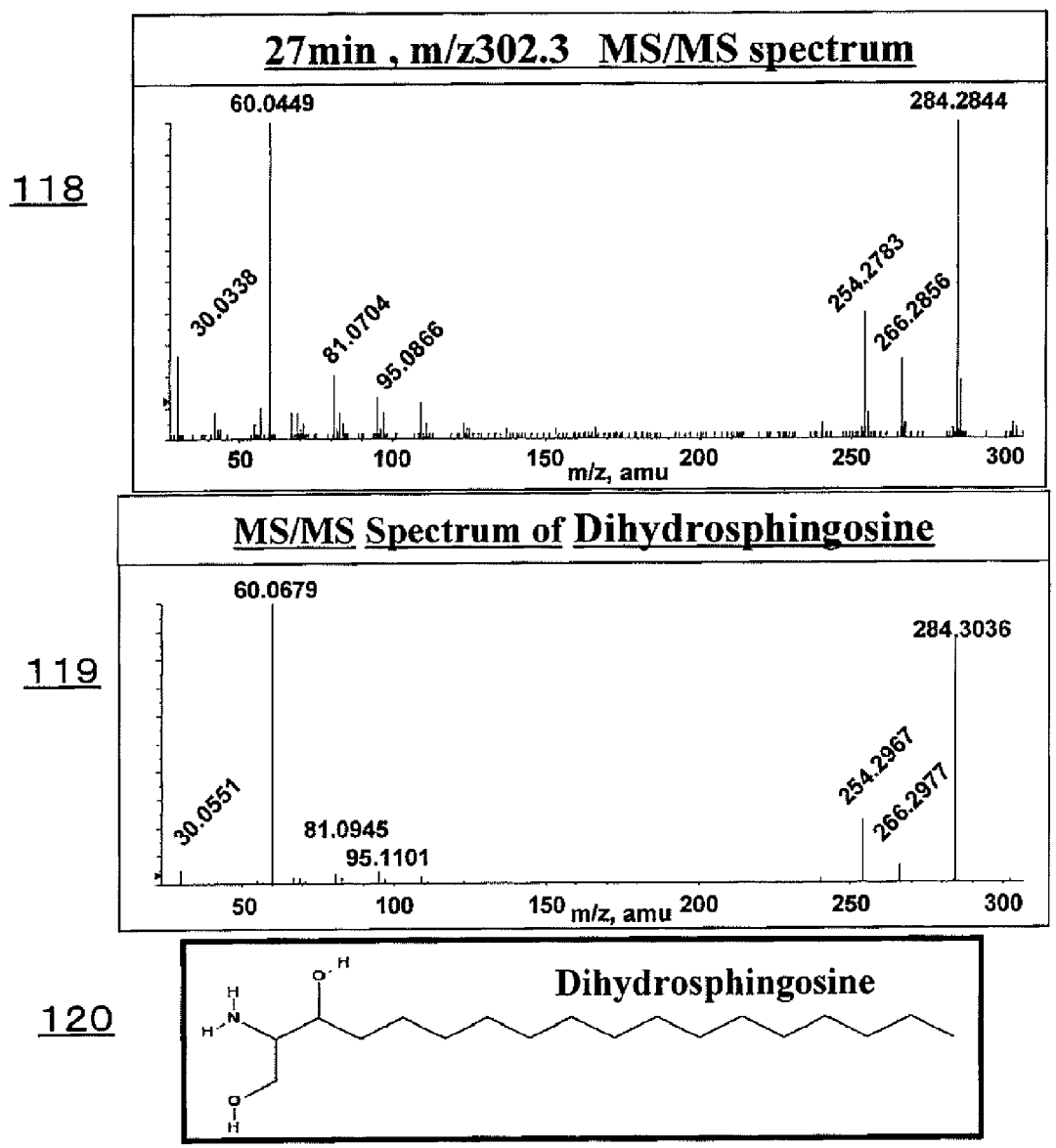

The result of MS/MS analysis of the above peak is the spectrum 118 in FIG. 49. It was found that the molecule was Dihydrosphingosine by comparing the spectrum with the data 119 in databank of mass spectra. Thus, the molecules can be identified rapidly. If there are corresponding data to obtained MS/MS spectrum in the databanks, the time required for intracellular content capturing to key molecular peak extraction is two to three hours, followed by two hours molecular structure determination by MS/MS showing this method to be highly precise with overwhelming speed. In addition, the method is characterized by the ability to link with cellular morphological changes, too.

Figure 50:
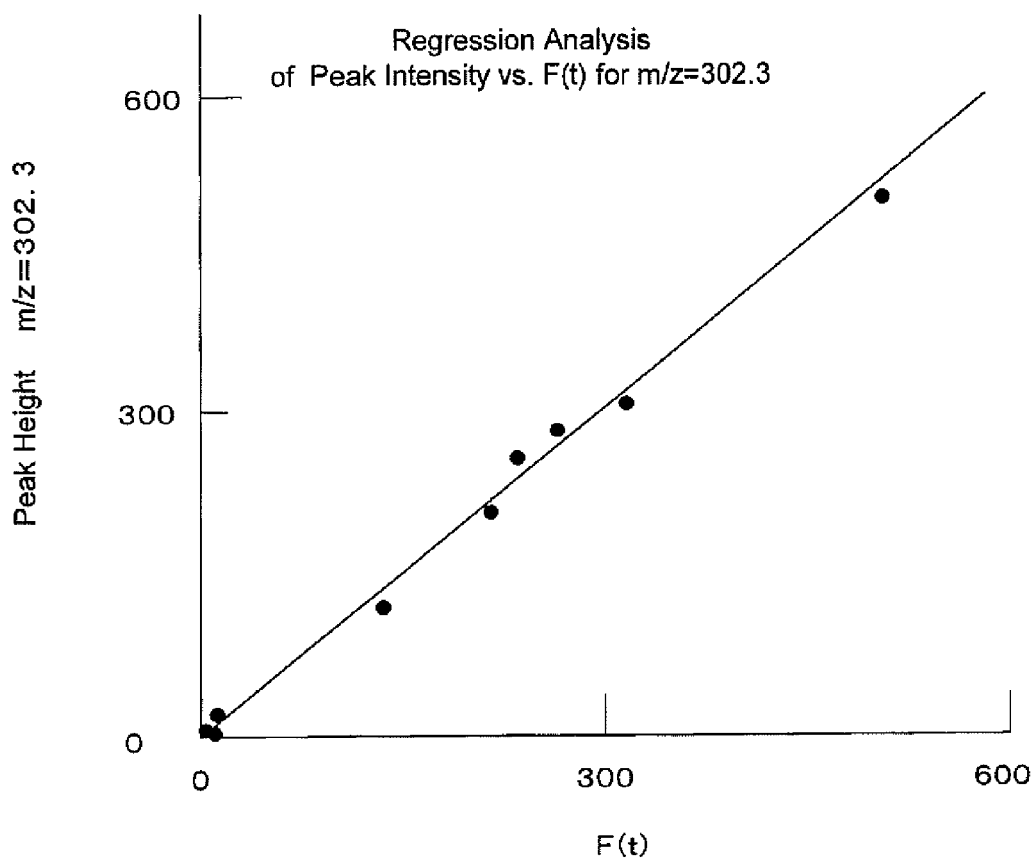

FIG. 50 shows the result of regression analysis of disappearing function aiming temporal change of m/z 302.3 peak intensity. The function well represents the correlation of time dependent change of the peak intensity. Thus, it is possible to simulate molecular dynamics in single cell by regression analysis.

This mass spectrometric method utilizes the nanospray ionization as comprehensiveness can be ensured and MS/MS analysis can be easily performed, while MALDI ionization method can be also adopted which adapt to high molecular component analyses. MALDI is a tremendous analytical method: take a whole single cell, add matrix solution on it, recognize the existence of the cell during crystallization of matrix, tried to find the cell through display as the sample plate is manipulated under vacuum, continued irradiation of laser beam until cell signal appears. And whole cell analysis using MALDI gives only a small number of detectable peaks because the molecules with strong peaks such as cell membrane components mask other molecules ionization because the target of analysis. By this invention, the site-specific capture of cellular components shown in FIG. 51 such as sampling without the cell membrane or with the cell membrane alone become possible, and detection of high molecular weight components which the nanospray is not good at has been achieved by spotting the captured sample on the distinguished position of sample plate 264, followed by adding matrix solution 265 on it and MALDI ionizing and detection.

Figure 52:
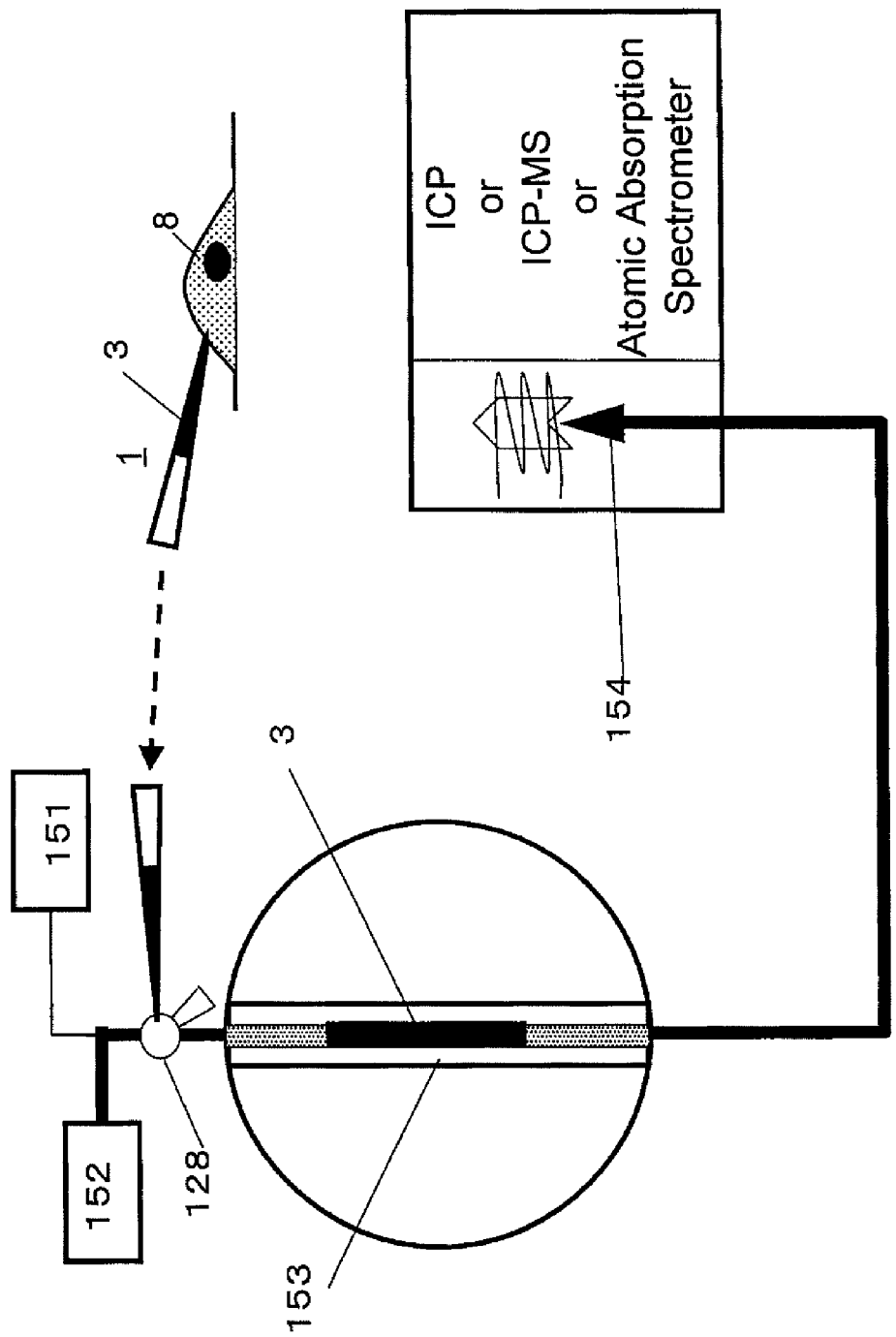

FIG. 52 shows the case that the analytical method is other than mass spectrometry. In this method, the inorganic substances such as metal ions can be detected by injecting the captured intracellular components into the sheath flow of two-layered liquid streams in one line followed by introducing them into atomic absorption spectrometer, ICP or ICP-MS while preventing the contact or absorption of the cellular components to the line.

Figure 53:
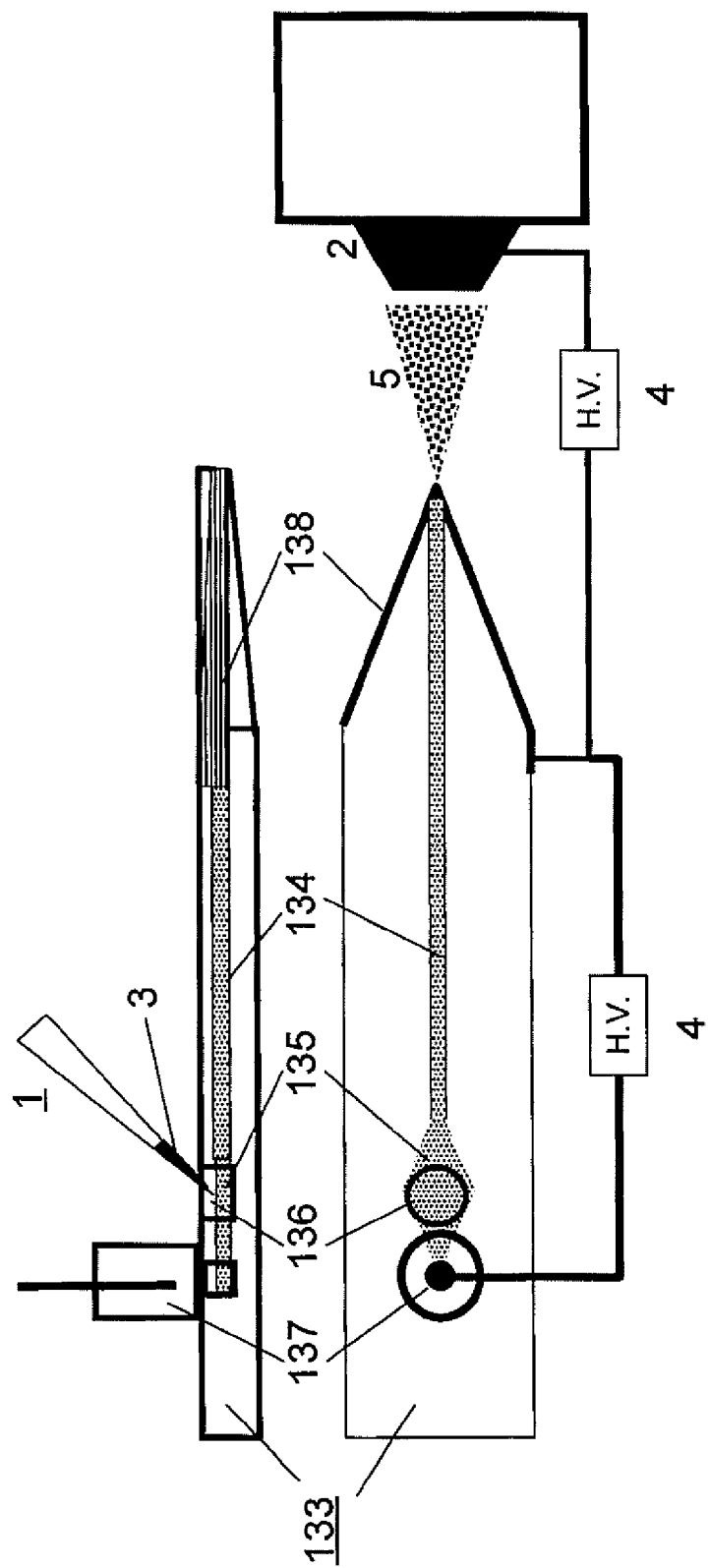

FIG. 53 is the example of single cell analysis using micro electrophoresis tip: the sample of single cell 3 captured with this method is added to the separation system of micro tip 133, the components are concentrated at the concentrating zone 136 et al and separated by inducing capillary electrophoresis 134, and nanospray 5 is induced by applying high-voltage at the sharp-edged forefront 138.

Figure 54:
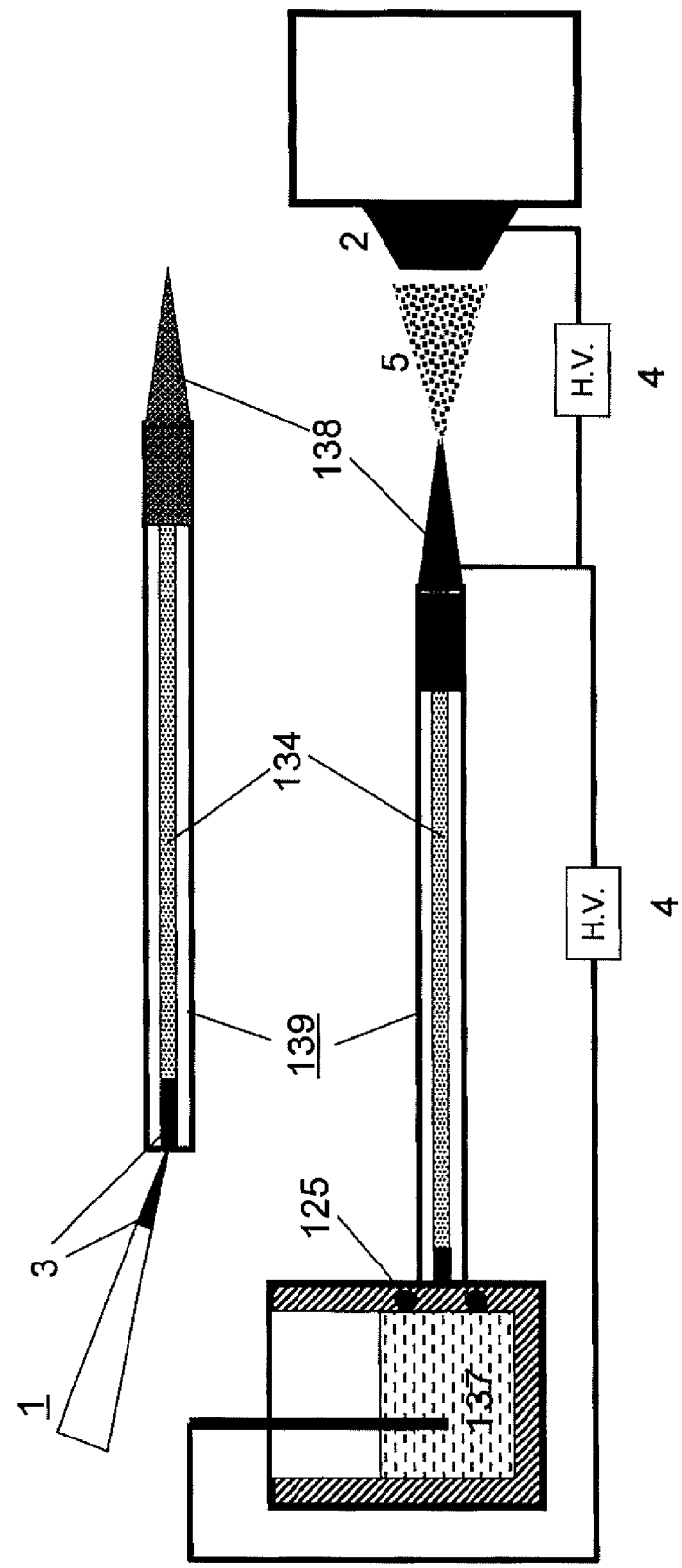

FIG. 54 is the example of accomplishment of similar separation with the capillary body alone. A small amount of sample solution is added to the unfilled zone of the back-end of capillary and separated by capillary electrophoresis. In this case, polymer gel et al can be present inside the capillary. Apparently different molecular peaks are observed by comparing the total ion chromatograms (TIC) before and after treatment of cells with medicine and comparing the spectra at a certain retention time like FIG. 55.

Figure 56:
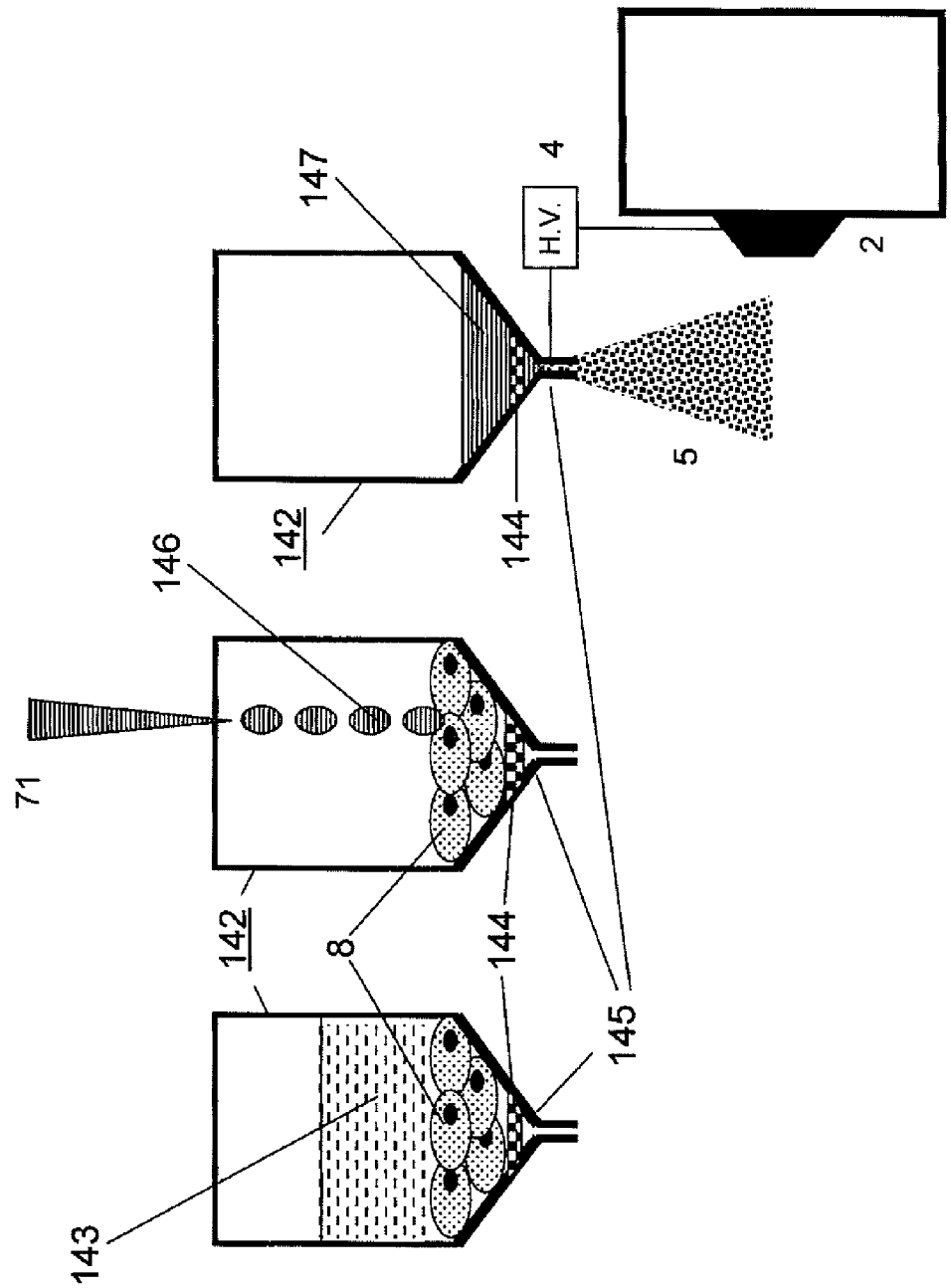

In addition, FIG. 56 shows the rapid intracellular molecule kinetic tracing method in not single cell system but multicellular system for high throughput analysis. In this figure, multiple numbers of cells are put in the well made in the sample plate 142, forced to proliferate to some extent with cell culture medium 143 and drug treated. The cell groups treated and untreated are washed using filters for cell trapping 144, then the cells are dissolved in ionization solution for intracellular component elution 147. The eluted cell component was forced to nanospray ionization from the conductive nanospray protruding part in bottom of the well 145, and is introduced into the mass spectrometer.

Figure 57:
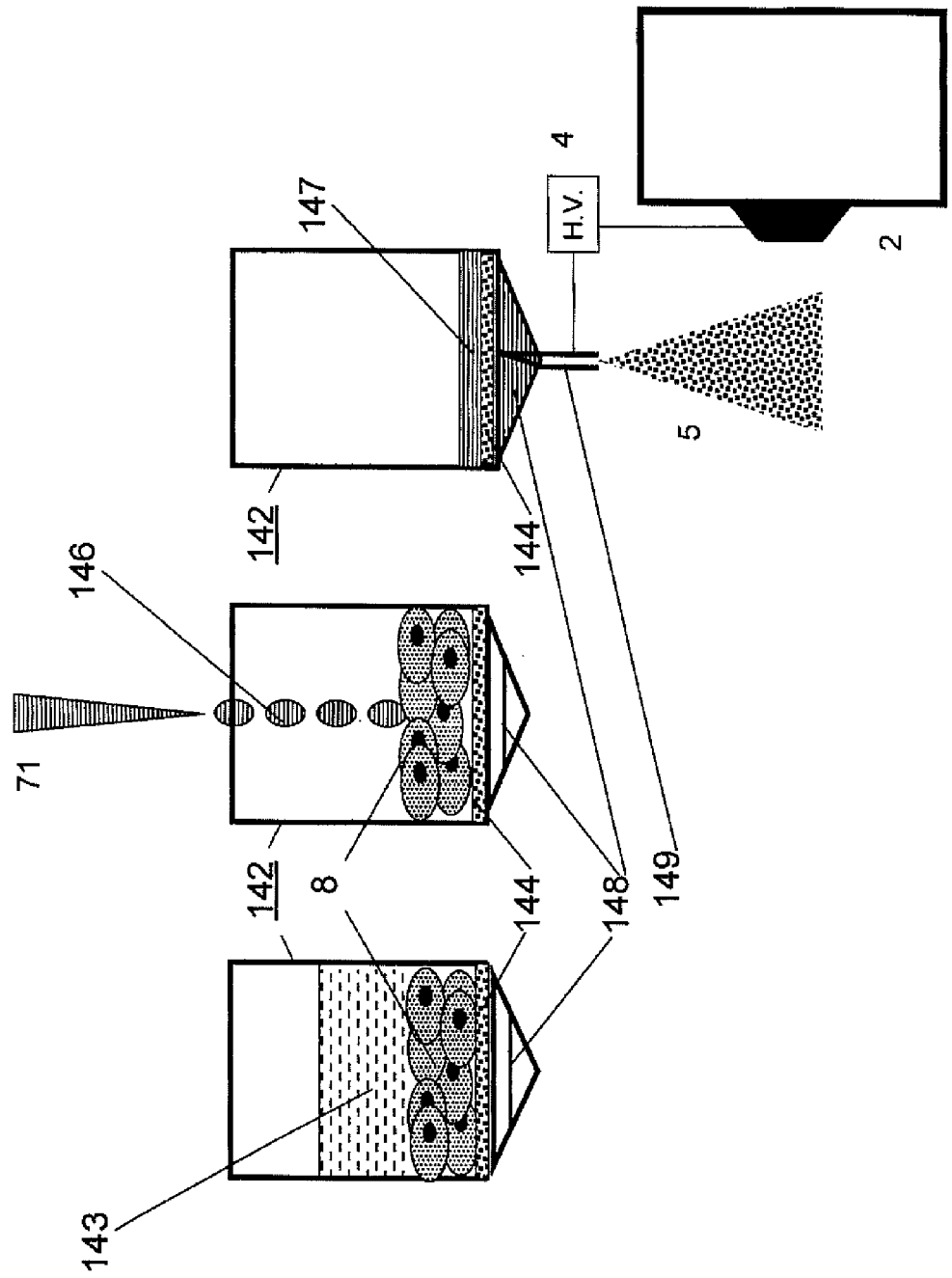

The system in FIG. 57 is similar to that in FIG. 56. The difference is that nanospray is induced by sticking nanospray needle from the bottom of the well and by applying high-voltage electric field to it after dissolving the cells in the last step. Ultrasonic wave et al can be used for cell breakage.

Figure 58:
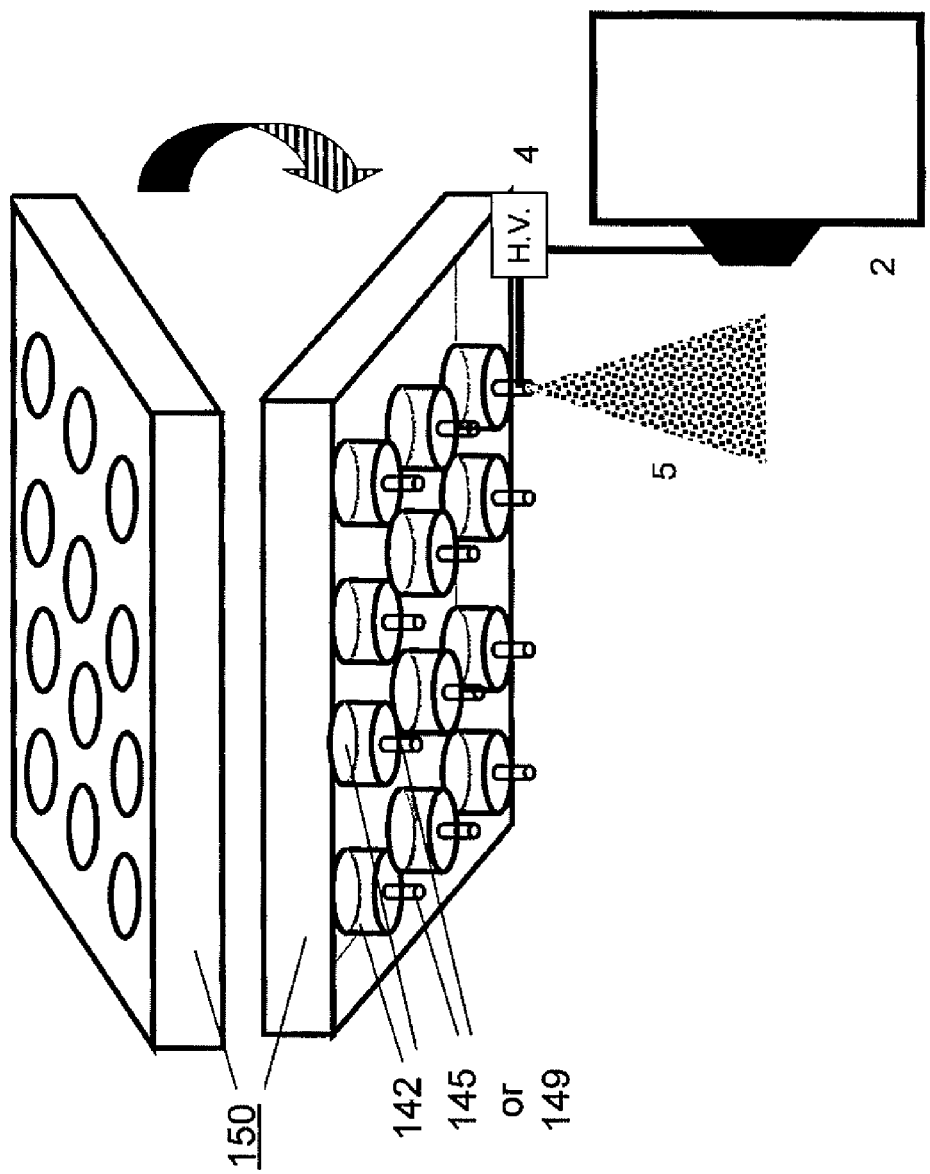

FIG. 58 shows that such wells are placed in the sample plate 150, and the nanospray is induced one after another routinely from the bottoms of wells 145 or 149 to be analysed by mass spectrometry.

Figure 59:
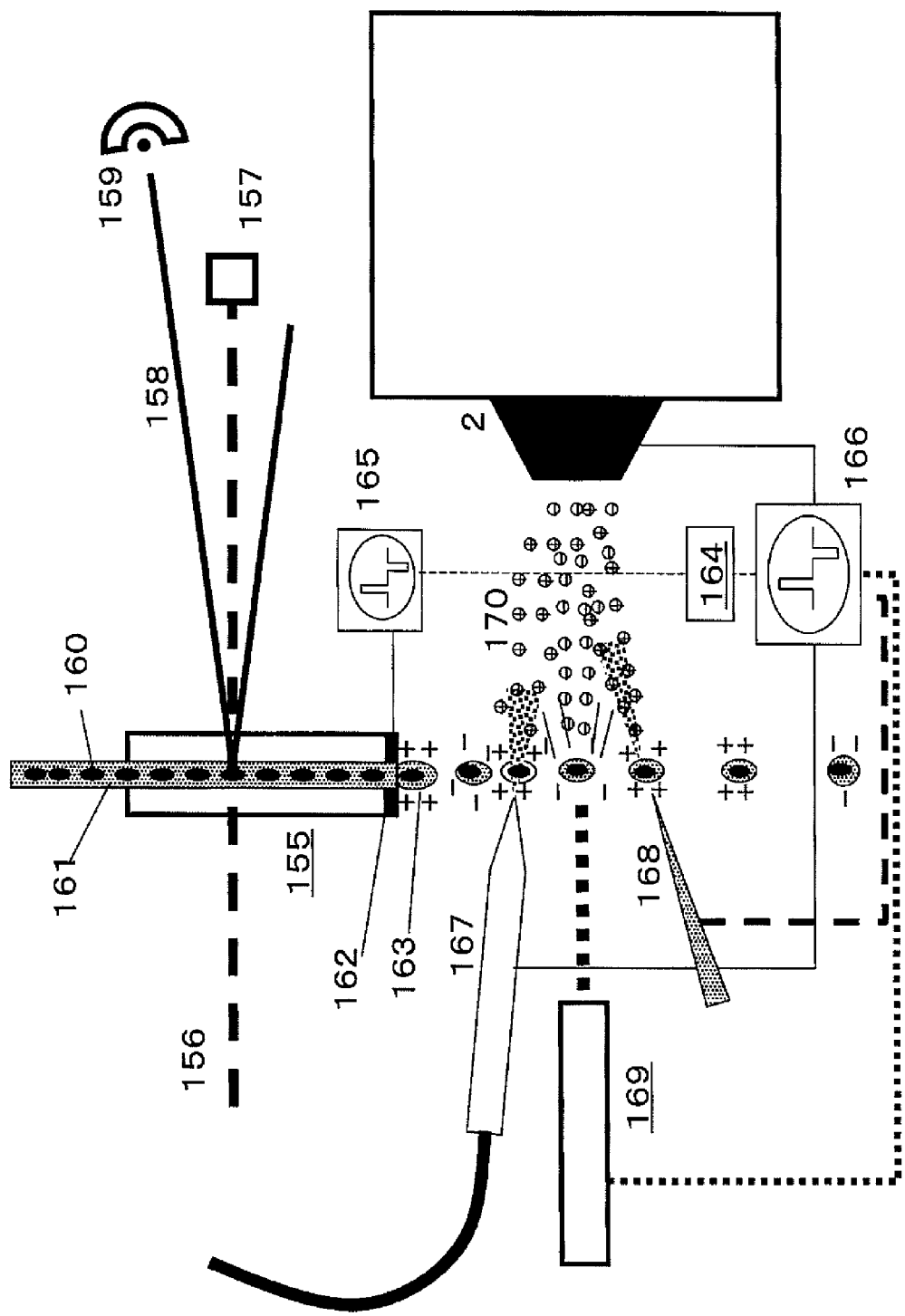

FIG. 59 shows the example of more rapid single cell mass spectrometry enabled. The method is that the cell containing droplet spitted out from the flow cytometer 163 is charged to blow out minutely by timing-synchronized positive or negative pulsed high voltage 166 applied to pulse nanospray, pulse electrical terminal 167 or pulse laser 169, and is introduced them into the mass spectrometer. This enables us to advance the analysis in cooperation with the extremely rapid cell morphology detecting.

Figure 60:
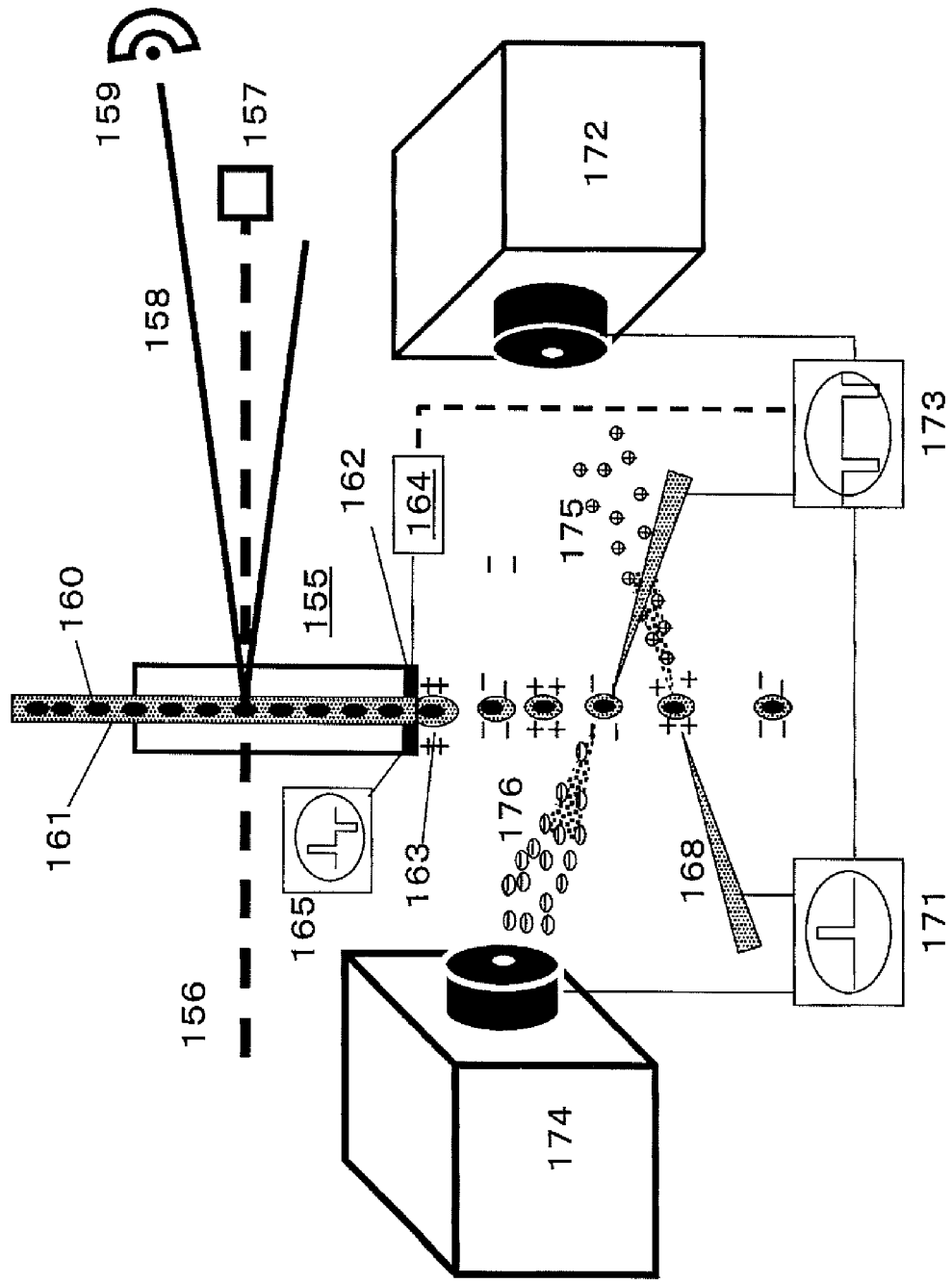

FIG. 60 shows the progressed system of that in FIG. 59. Positively and negatively charged cell containing droplets 163 are independently blew out using exclusive terminal for positive (168) or negative (175) electric pulse, and introduced into the mass spectrometer for positive ion analysis 172 and that for negative ion analysis 174. This system achieved faster single cell molecular analyses.

Figure 61:
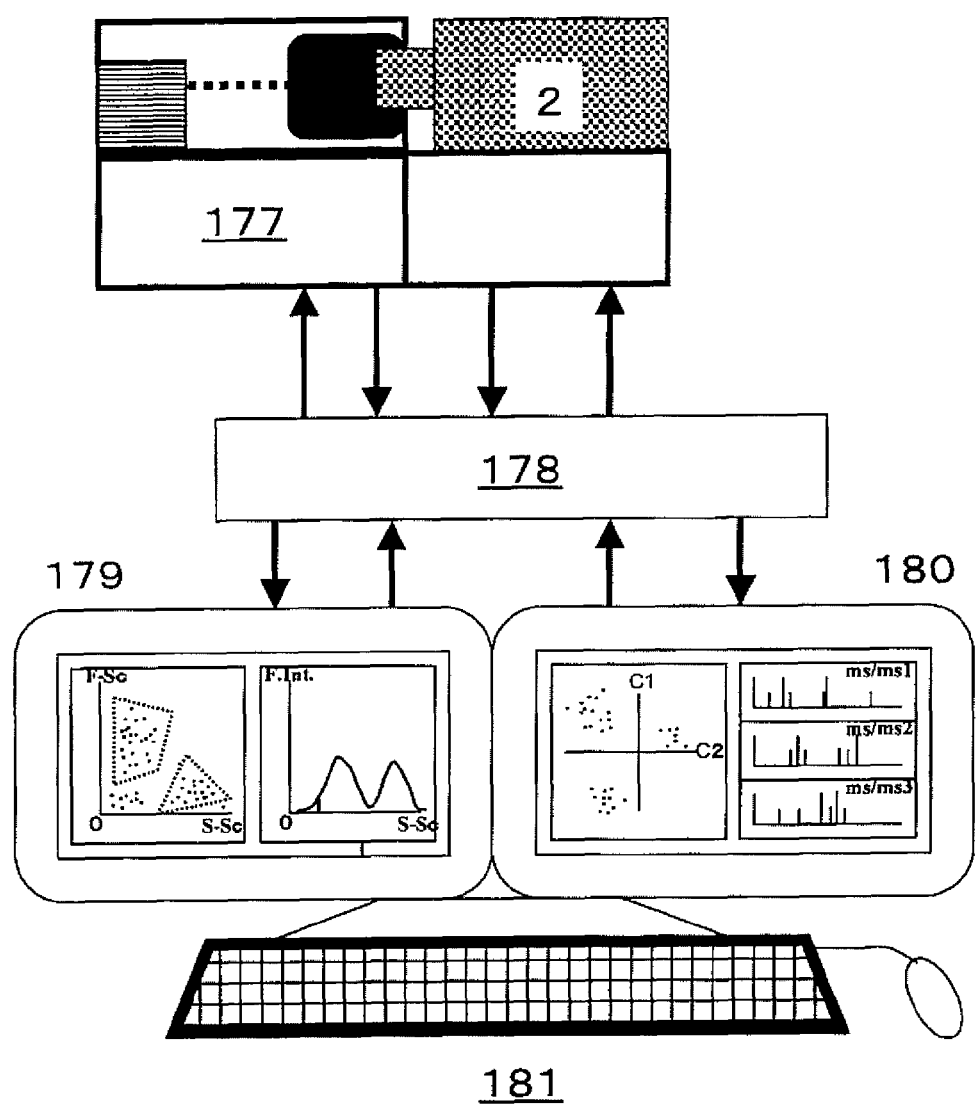

FIG. 61 shows example of the system that the cell sorter and mass spectrometer are combined as shown in FIG. 59. By this system, the scatter diagrams and the density diagrams which reflect the cell morphologies and surface markers obtained by the cell sorter, and the results of principal component analyses and MS spectra which show the attribution of each cell, can be obtained in the same time.

Figure 62:
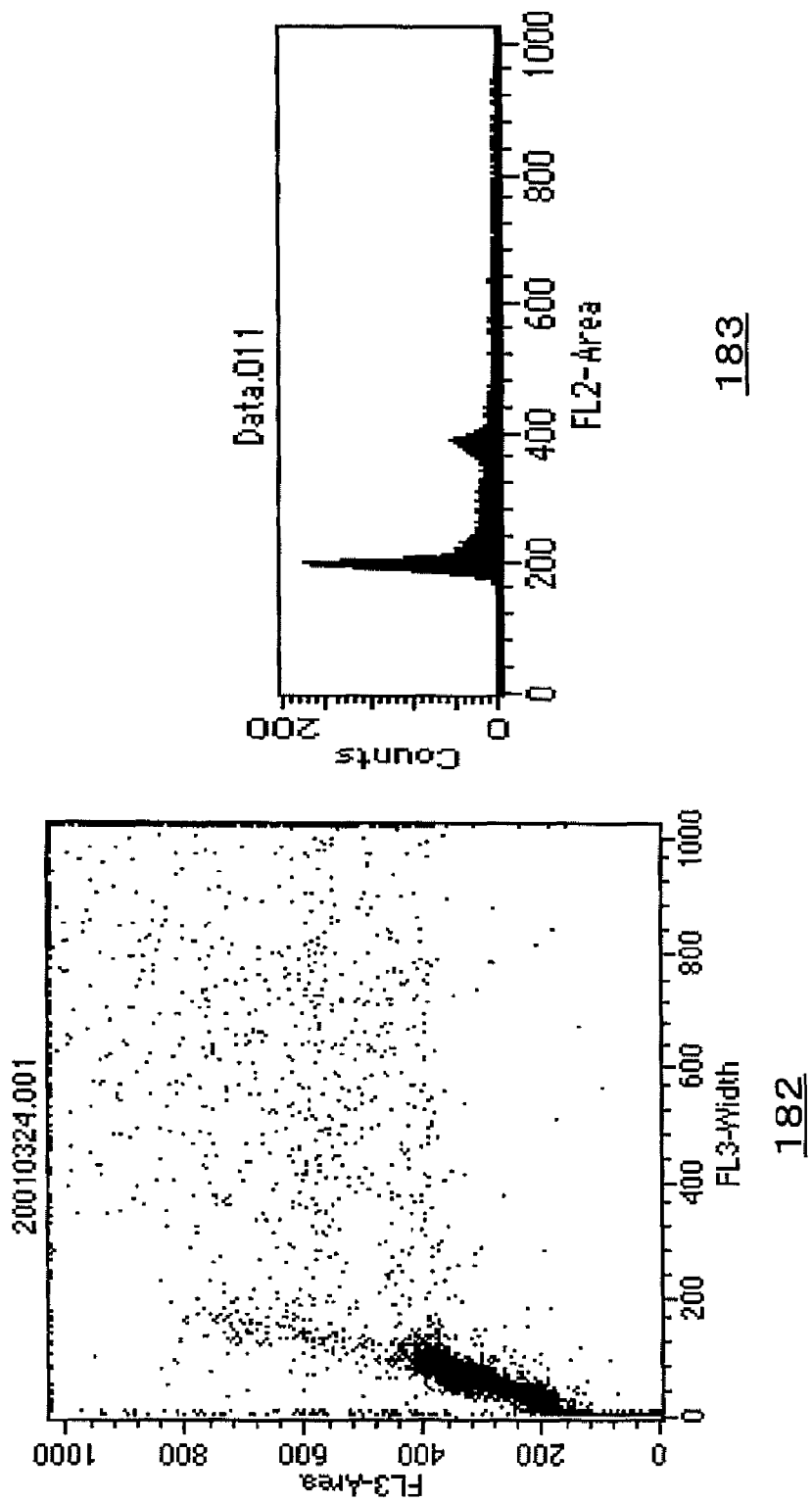
Figure 63:
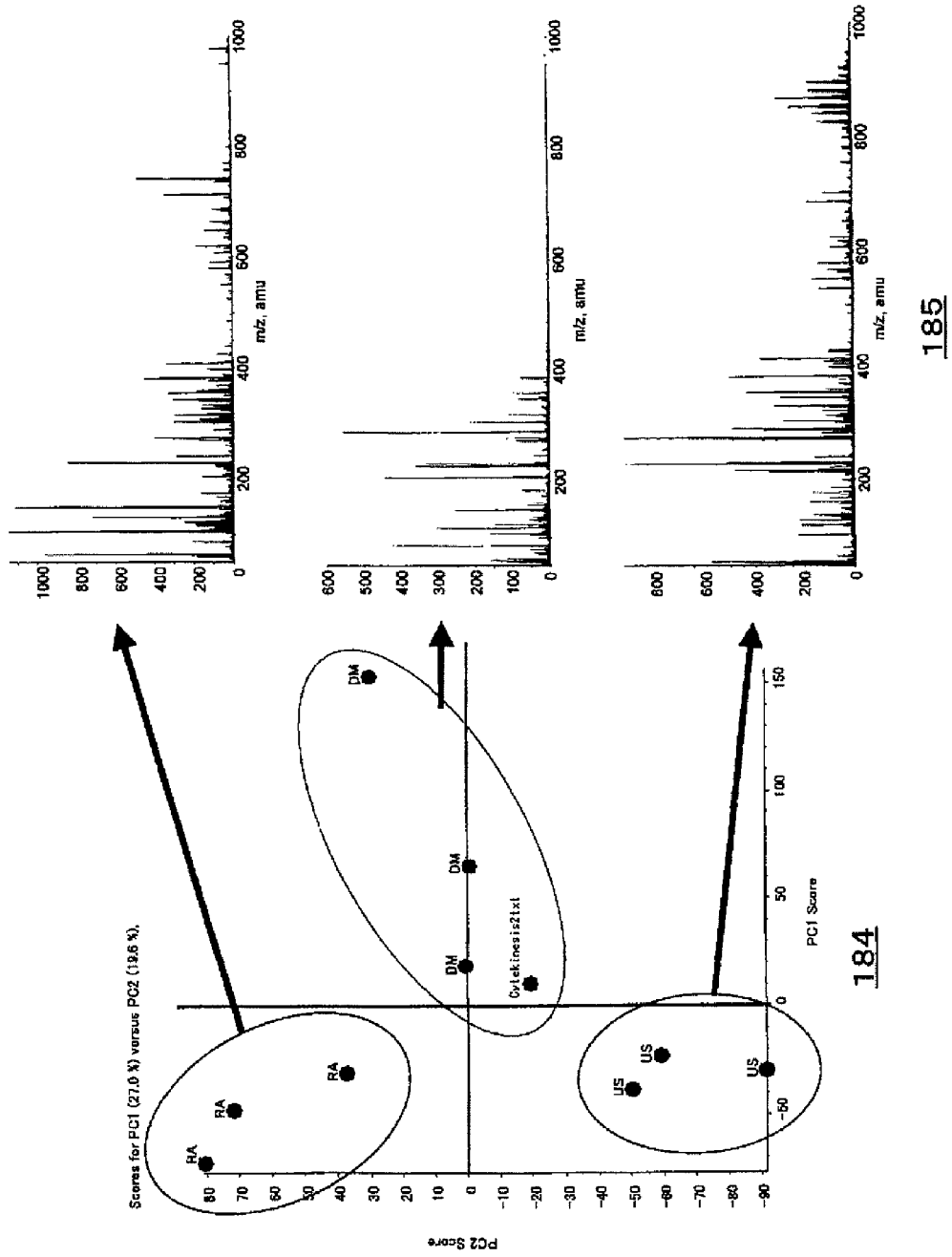

FIG. 62 shows the above described scatter diagram of blood cells 182 and the density diagram of fluorescent marker which select only lymphocytes 183. In FIG. 63, three types of cell groups are clarified by the result of principal component analysis 184 determined from MS spectra of selected lymphocytes on positive mode. And these averaged spectra 185 were obtained.

These molecules are correlated with not only the cellular behaviors observed simultaneously but also with the other detected molecular groups. It will be resulted in not only the clarification of the molecular mechanisms of life phenomena, but also the finding of candidate molecules of new medical substances. If the cell is a cancer cell, it will bring the discovery of molecules which cause the disease, and the clarification of the mechanisms which might lead to the development of diagnostic method. There have been no previous cases in which molecules are detected and structurally defined among many of the molecular peaks from a single cell, with observed cellular behaviors in addition, and evaluated their attribution degree in which certain molecular peak attributes to some cellular behavior or the conditioned cell state using such analytical processes. Above all, it is clear that the mechanisms of life phenomena which has been remained unknown until now will be clarified dramatically and various applications of them will progress significantly.

INDUSTRIAL APPLICATION POSSIBILITIES

As described above, this invention provides the methods to clarify both life phenomena and their molecular mechanisms in micron-scale as small as a single cell rapidly and directly, and it will be used for enormous purposes. Above all, it will accelerate clarifications of molecular mechanisms of diseases by comparing the dynamics and molecules of disease cells and normal cells. And various applications will be really possible: if intracellular molecular mechanisms are clarified, drug discovery and development of diagnostics and treatments utilizing the molecules or mechanisms will be possible, and if new molecules are discovered, applications to new medicines and development of reagents for life sciences will be achieved. Above all, it is clear that the mechanisms of life phenomena which have remained unknown until now will be clarified dramatically.

A cell which purposely-behave and respond to outside factors usually couples their behaviors and intracellular molecular kinetics. Real-time microscopic observation of cells and molecular detection enables quick clarification of purposely-constructed molecular mechanism of living phenomena. This invention provides the methods to clarify both life phenomena and their molecular mechanisms in micrometer-scale as small as a single cell rapidly and directly and it will be used for enormous purposes. Above all, it will accelerate clarifications of molecular mechanisms of diseases by comparing the dynamics and molecules of cells in disease state and those of normal cells. And really various applications will be possible: if intracellular molecular mechanisms are clarified, drug discovery and development of diagnostics and treatments utilizing the molecules or mechanisms will be possible, and if new molecules are discovered, applications to new medicines and development of reagents for life sciences.

And speed-up of the clarifications of various intracellular molecular mechanisms will enables to provide faster discoveries of new molecules including candidate molecules of medicinal substances and new life phenomena, and develop and accelerate medical cares, diagnostics and applications to biotechnology widely. Various analyses will developed rapidly, for example rapid explorations of cell differentiation factors of stem cells in such as regeneration medicine, the discovery of the factors controlling cell differentiation, growth and control methods of them, molecular diagnostics and explorations of cell species such as cancer cells and identifications of cell species.

The dynamics of small molecules in cells can be clarified associated with many genes and proteins, the expression products of genes, which have been analyzed comprehensively about various disorders now, namely integrated clarification of life phenomena becomes possible. Integrated comprehensive understandings of life phenomena contribute to life realization and advance in health of human being and can produce various attendant enterprises.

And in food field, it provides analyzing method of the small molecules dynamics in cells in which the subtle quality of molecules such as flavor and fragrance can be provided.

In addition, in general chemical manufacturing industry, for example, the clarification of molecular mechanisms at very small region in nanotechnology, in product control of high-purity organic semiconductor, organic conductors, organic optical materials and in the manufacturing process of products which quality certification in the viewpoint health care is significant such as food ingredients, very small amounts of byproducts may give wrong effects on required quality in physiochemical ability and safety. This method enables to monitor such byproducts, manufacturing control and quality control at detection of molecules and analysis in very small area.

SIMPLE EXPLANATION OF FIGURES

FIG. 1 Moment of releasing granules in allergy reaction of allergic cells and the time course change of the number of released granules in every cell.

FIG. 2 Capillary tip for nanospray ionization (figure below) and its operation scheme (figure above).

FIG. 3 Suction of intracellular fluid by the capillary tip for nanospray ionization under observation with a microscope.

FIG. 4 Figure of capillary tips for nanospray ionization; tip with conductive coating on its surface (upper figure), tip without conductive coating (lower fig.). Cellular fluid caught in the latter tip were added with ionizing solvent, then electric terminal for high voltage charge is inserted inside from the backward of the tip because of the absence of conductive surface in order to introduce cellular fluid to mass spectrometer as ionized spray.

FIG. 5 A system example of real-time mass spectrometric analysis of intracellular fluid's molecules: Inserting the capillary tip for nanospray ionization into the cell under microscopic observation, sucking cellular content of the single cell, adding appropriate ionizing solvent, quickly introducing into mass spectrometer to analyze cellular phenomena such as movement and shape.

FIG. 6 Principle of molecular exploration and identification: comparing mass spectra of cells with different condition a and b, extracting certain phenotype specific peaks (22(*a-b*)), identifying molecular structure from MS/MS spectrum (23) obtained by selected fragmentation of the molecule of certain peak in the collision cell.

FIG. 7 Example of peaks, exact mass, detecting condition, and t-test value: from t-test results obtained from comparing mass spectra of cells with different condition a and b, condition a specific (t value>95%) peaks are shown.

FIG. 8 Group dependent peak intensity: comparison of the peak intensity specifically observed in eleven cells with certain condition (left group (27)) and the intensity of same m/z peaks from six comparing cells (nearly zero (right group (28))).

FIG. 9 Example of molecular exploration by obtaining intracellular fluid of a mast cell under observation followed by serial process of this invention.

FIG. 10 Mass spectra of mast cell model RBL-2H3 single granule and cytoplasm content (203 and 204, respectively). Expanded spectra of granular and cytoplasmic peaks with certain m/z are indicated with their t-values obtained from t-test (205-210). In this case, t-values of granularily localized peaks are nearly 100 whereas t-values of peaks with cytoplasimic localization are almost −100.

FIG. 11 MS/MS analyses of five peaks in FIG. 10.

FIG. 12 Metabolic process and localization of five molecules obtained from FIG. 10 and FIG. 11.

FIG. 13 Metabolic map centered on histidine obtained from component analysis of single intracellular granule using mast cell model, RBL-2H3.

FIG. 14 Detection of extracellularily released component by calcium ionophore stimulation in mast cell model, RBL-2H3.

FIG. 15 Classification of seven cell lines by single cell mass spectra: result of principal component analysis, the score plot 221 and the loading plot 222.

FIG. 16 Morphological change, single cell mass spectra and molecular exploration in retinoic acid induced differentiation of P19 cells.

FIG. 17 Detection of drug metabolites in a cell using HepG2.

FIG. 18 Blood content detection from blood recovery at a point by practically using single cell mass spectrometric detection.

FIG. 19 Leaf and stem of plant (Gelanium)-targeted single cell direct analysis and molecular exploration.

FIG. 20 Intra- and extracellular molecular tracking in a single cell using labeled molecules.

FIG. 21 Example of uptake and localization detection of quinacrine in a mast cell model system.

FIG. 22 Example of uptake and tracking of isotope-labeled histidine in a mast cell model system.

FIG. 23 Internal standard method using solvent peaks for correction of peak intensity.

FIG. 24 System configuration of intracellular component capturing and introduction to mass spectrometer using a capillary tip for nanospray ionization.

FIG. 25 Method of tip bore measurement and micromanipulator driving in intracellular component capturing FIG. 26 Automated system configuration of capturing intracellular component and introducing to mass spectrometer using a capillary tip for nanospray ionization.

FIG. 27 Floating cell capture method-attached automated system configuration of capturing intracellular component and introducing to mass spectrometer using a capillary tip for nanospray ionization.

FIG. 28 Example of conductive coating on a capillary tip for nanospray ionization.

FIG. 29 Thin core material with sample solvent affinity (become solvent leading route) or with electro conductivity-containing apparatuses inside of a capillary tip for nanospray ionization.

FIG. 30 Comparison of nanospray stability between tips with and without thin core material with sample solvent affinity (become solvent leading route)

FIG. 31 Image of insertion of a capillary tip for nanospray ionization with hydrophobic surface to a cell FIG. 32 Elution image of molecules at the forefront of the ionization capillary which enables single cell analysis by nanospray ionization.

FIG. 33 Introduction method of ionization supporting solvent to captured fluid of intracellular components.

FIG. 34

Several modification methods to the inside of a capillary tip forefront for nanospray ionization.

FIG. 35 Several resin filling methods to the inside of a capillary tip forefront for nanospray ionization.

Figure 36:
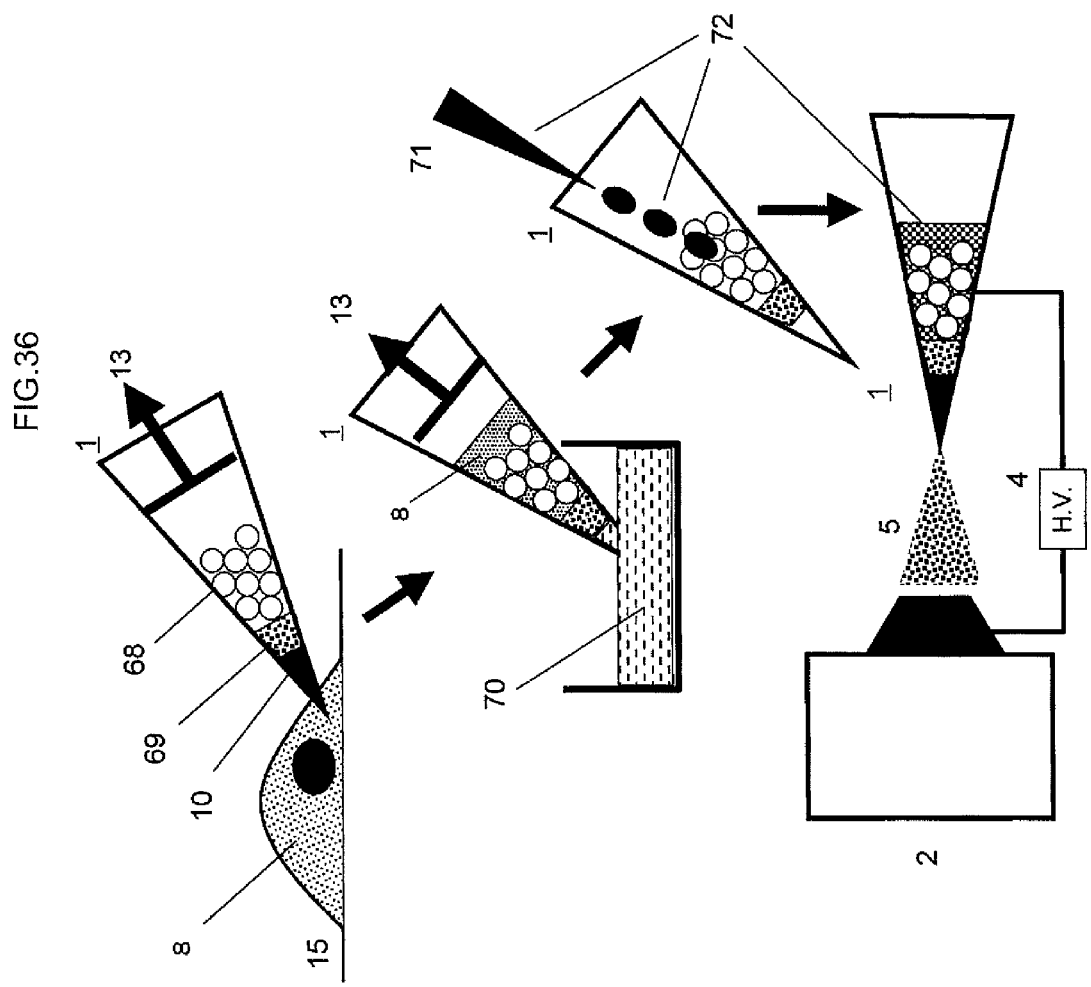

FIG. 36 Concentration and elution detection by floating resin after suction of cellular component.

FIG. 37 Concentration and elution detection by fixed resin or by intra-surface coating after suction of cellular component.

FIG. 38

Well-shaped ionizing introduction method of intracellular component.

FIG. 39 Component amplification or heat denaturation treatment method in intracellular component-captured fluid.

FIG. 40 Solution of forefront plugging of a capillary tip for nanospray ionization.

Figure 41:
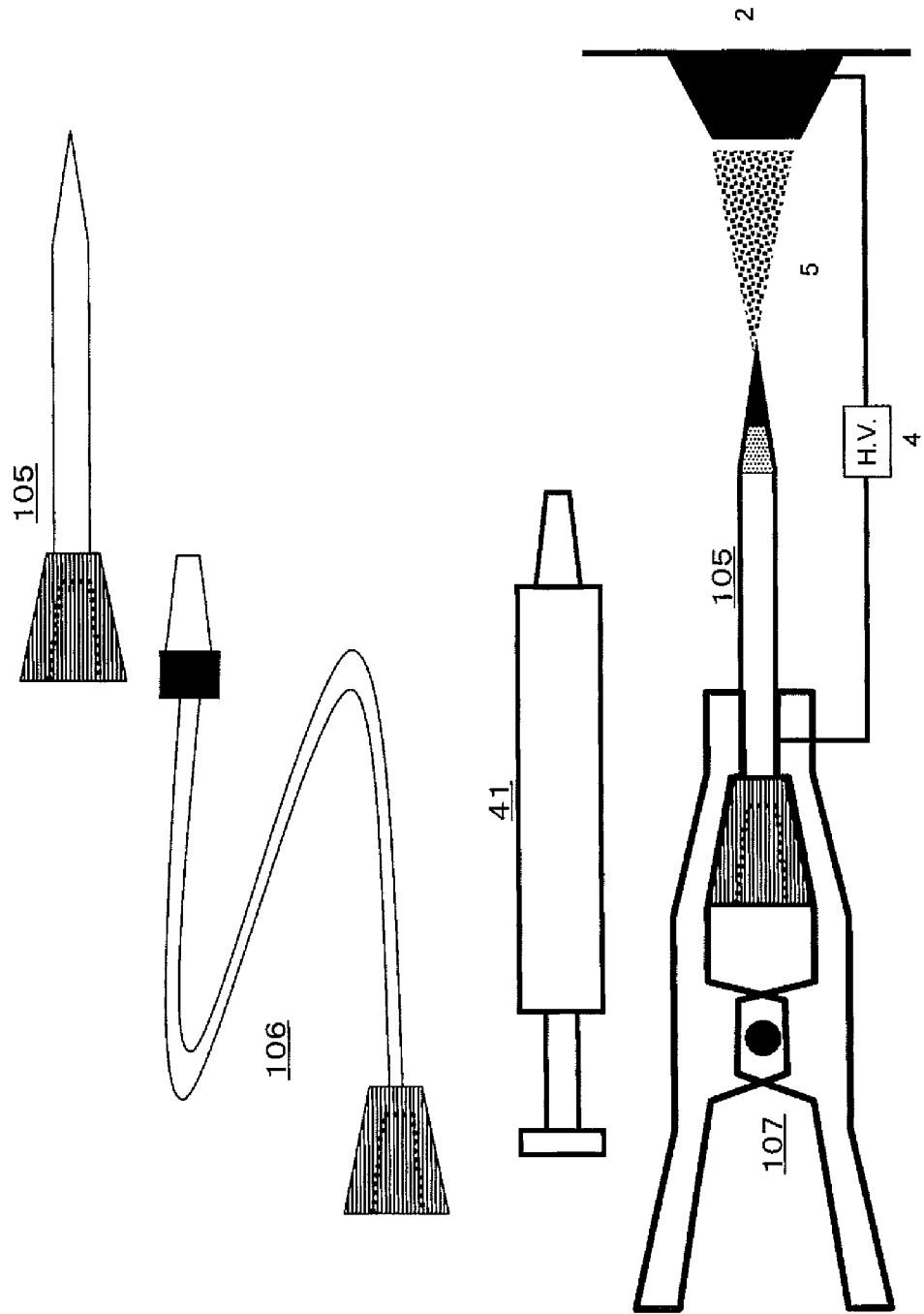

FIG. 41 Improved capillary tip for nanospray ionization and pheripheral apparatus for simplification of suction FIG. 42 Various voltage application methods in single cell nanospray ionization.

FIG. 43 Evaluation methods for very small suction volume and dilution ratio.

FIG. 44 Working content and correlation of data processing system of this method.

FIG. 45 Example of intracellular composition analysis using nano LC separation.

FIG. 46 Mass spectra (three dimensional presentation) of every fraction before and after steroid treatment in lymphocytes.

FIG. 47 Mass spectrum peaks extracted as high belongings from peaks of FIG. 20 by t-test.

FIG. 48 Existing group of m/z 302.3 spectrum.

FIG. 49 MS/MS spectrum of m/z 302.3 and identified molecular structure.

FIG. 50 Functional regression analysis of m/z 302.3 temporal change.

Figure 51:
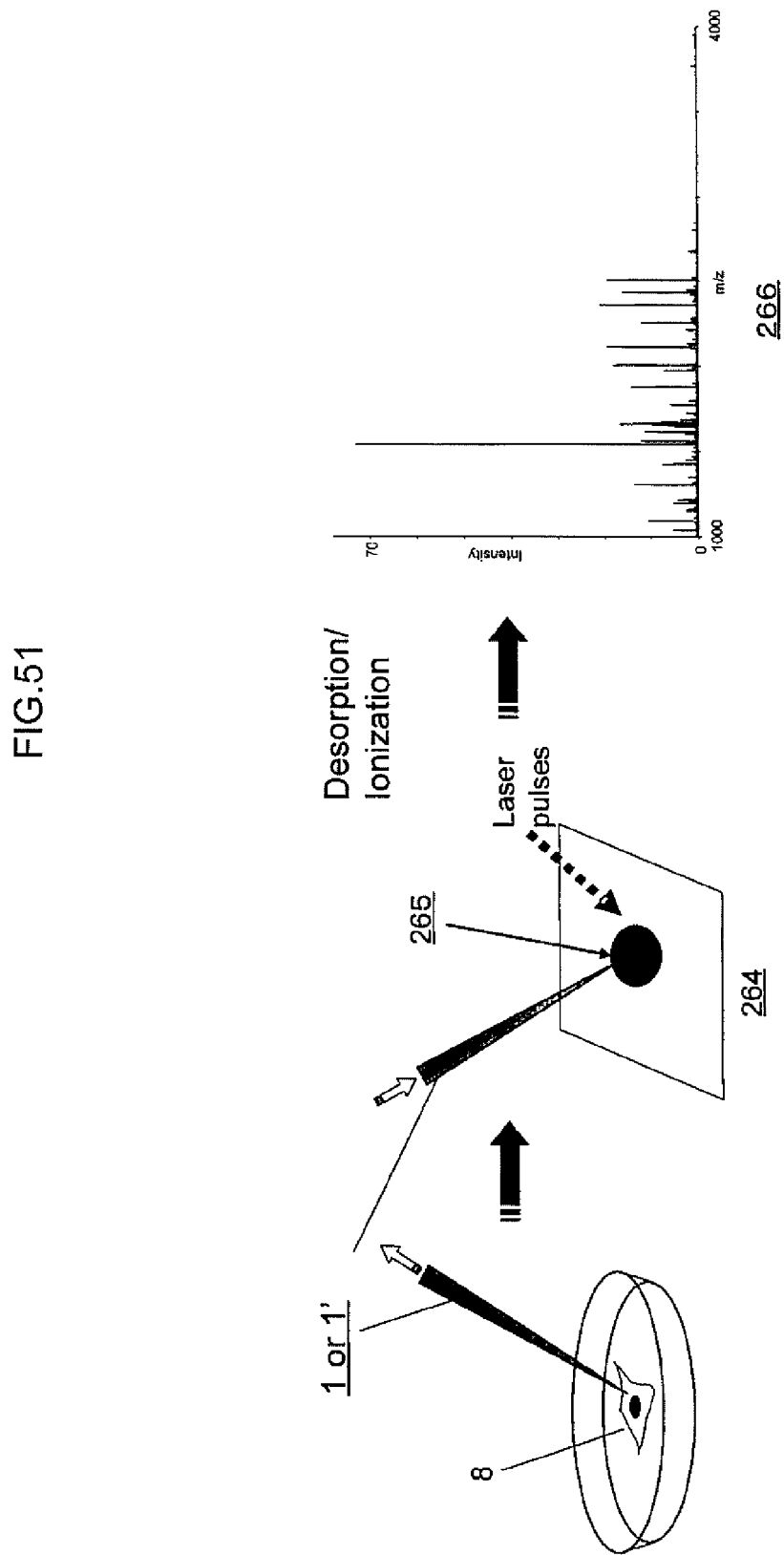

FIG. 51 Content capturing by a capillary tip for nanospray ionization and MALDI-TOF detection.

FIG. 52 Single cell atomic absorption analysis or ICP, ICP-MS analytical method.

FIG. 53 Example of single cell analysis using micro electrophoresis tip.

FIG. 54 Example of single cell analysis using micro separation capillary.

FIG. 55 Example of nano separation of cells in deferent states (a) before steroid treatment, (b) after steroid treatment FIG. 56 Example of mass spectrometrum of multiple-cell component analysis using well for sample plate 1.

FIG. 57 Example of mass spectrometrum of multiple-cell component analysis using well for sample plate 2.

FIG. 58 Example of mass spectrometrum of multiple-cell component analysis using sample plate-style nanospray.

FIG. 59 Cell sorter style-high speed single cell mass spectrometry system

FIG. 60 Cell sorter style-high speed single cell mass spectrometry system (simultaneous positive and negative analysis style)

FIG. 61 Component of unified cell sorter style-high speed single cell mass spectrometry system.

FIG. 62 Scattergram and densitogram obtained by a cell sorter.

FIG. 63 Principal component analysis result and mass spectrum simultaneously obtained from a mass spectrometer.

EXPLANATION OF SYMBOLS 1 nanospray ionization capillary tip (metal-coated surface type)
1' nanospray ionization capillary tip (electrode inserted type)
2 mass spectrometer
3 sample solution or the mixed solution added the ionization supporting solvent from the back-end of the nanospray ionization capillary tip 4 high voltage (this example shows the positive mode and the nanospray ionization capillary tip is subjected to a positive potential.)
5 nanospray
6 metal-coated surface of the nanospray ionization capillary tip
7 main body of nanospray ionization capillary tip (the example of insulator main body)
8 cell
9 microscope stage
10 the captured cell fluid
11 objective lens
12 video camera
13 operation of suction
14 electrode inserted into the sample solution
15 petri dish
16 cell culture fluid
17 monitor
18 computer
19 video microscopic image of the cultured cells in the petri dish
20 mass spectrum of the intracellular fluid of the target cell in the screen
21a mass spectrum of the intracellular fluid captured from cell a
21b mass spectrum of the intracellular fluid captured from cell b
22 peak of the differential mass spectrum between 21a and 21b
23 MS/MS spectrum of the parent peak observed in 22
24 peak name of the mass spectrum
25 m/z value
26 t-value
27 peak intensities observed in each cell at m/z values found specifically in eleven cell groups (27) in a state
28 peak intensities at the same m/z values as 27 shown in six cell groups (28) in a different state from 27
29 video microscopic image on capturing the intracellular fluid from a cell by the nanospray ionization capillary tip 1
30 mass spectrum of the intracellular fluid captured from cell A
31 mass spectrum of the intracellular fluid captured from cell B
32 result of t-test between the mass spectrum of the intracellular fluid captured from cell A and that from cell B
33 fragment spectrum obtained by MS/MS analysis of a peak at m/z 112.0909 that is one of the molecular peaks detected specifically in cell A
34 chemical structure of histamine decided by MS/MS analysis of a peak at m/z 112.0909 that is one of the molecular peaks detected specifically in cell A
35 X-Y-Z driving stage of the holder that drives the cell insertion nanospray ionization capillary tip to the cell position (this figure shows electric type. Other is the manual gear coarse motion and micromotion type.)
35'X-Y-Z driving stage of the holder that drives the cell holding capillary tip to the cell position
36 axially-moving actuator of the holder that drives the cell insertion nanospray ionization capillary tip to the cell position (this figure shows electric type. Other is the manual piston type.)
36'axially-moving actuator of the holder that drives the cell holding capillary tip to the cell position
37 insertion into the cell by axially-moving actuator that drives the cell insertion nanospray ionization capillary tip to the cell position and the direction of pulling it back after suction
37'insertion into the cell by axially-moving actuator that drives the cell holding capillary tip to the cell position and the direction of pulling it back after suction
38 control device for driving of the holder of the cell insertion nanospray ionization capillary tip
38'cell holding capillary tip
39 terminal for driving of the holder of the cell insertion nanospray ionization capillary tip (this figure shows a joystick type. Other is a piston driving type with rotating body.)
40 tube for driving the suction of cellular components
41 piston to suck out cellular components (a syringe is also available.)
42 driving device of the piston to suck out cellular components
43 objective lens 1 to detect the top bore of the nanospray ionization capillary tip
44 video camera 1
45 objective lens 2 to detect the top bore of the nanospray ionization capillary tip
46 video camera 2
47 monitor to detect the top bore of the nanospray ionization capillary tip
48 mark to assign the position of the top bore of the nanospray ionization capillary tip (on the video monitor)
49 control computer
50 pump for suction and sending solution
51 tube for suction
52 tube for sending solution
53 conducting materials
54 coating on the outer surface of the nanospray ionization capillary tip
55 cell insertion part of the nanospray ionization capillary tip with coating (54)
56 capillary materials with affinity for sample solvent (capillary wire for solvent pathway)
57 conductive capillary materials
58 coating on the inner surface
59 fibrous or chainlike packed materials
60 brush like surface-bound material
61 hydrophobic surface binding substances or coating with hydrophobic materials
62 cationic surface binding substances or coating with cationic materials
63 anionic surface binding substances or coating with anionic materials
64 binding surface of receptor of antibody and so on
65 binding surface of antigen or substrate
66 binding surface of enzyme etc.
67 binding surface of nucleic acid
68 packing or molecular sieving packing with surface binding substances such as from 61 to 67
69 frit materials
70 solution for capture of molecules
71 micropipette
72 mixture of eluting solvent and ionization supporting solvent
73 well type nanospray part
74 burner or torch
75 hot bath (thermal cycler for PCR)
76 mixture of additional solution for treatment and captured cell fluid 77 solution before treatment such as PCR amplification and thermal denaturation
78 solution after treatment such as PCR amplification and thermal denaturation
79 discharge
80 mixture of eluting and ionization solvents and captured fluid such as cell fluid
81 tweezers
82 laser
83 mirror
84 cylindrical lens
85 labeled molecules or trailable isotopic molecules added to the extracellular fluid
86 labeled molecules or isotopic molecules for tracing that moved into cell and existed in intracellular fluid or that were introduced into subcellular organelle
87 labeled molecules or isotopic molecules for tracing introduced into or bound to membrane
88 metabolized or modified labeled molecules or isotopic molecules for tracing while moving into a cell
89 labeled molecules or isotopic molecules for tracing introduced into subcellular organelle
89' metabolites of labeled molecules or isotopic molecules for tracing introduced into subcellular organelle
90 labeled molecules or isotopic molecules for tracing that translocated to or were introduced into nucleus
91 metabolized or modified labeled molecules or isotopic molecules for tracing that were secreted or re-released into extracellular fluid
92 mass spectrum of components of cytoplasm of RBL-2H3 cell captured by this method
93 the enlarged spectrum of the part enclosed by dashed oval in 92
94 mass spectrum of components of intracellular granules of RBL-2H3 cell captured by this method
95 the enlarged spectrum of the part enclosed by dashed oval in 94
96 MS/MS spectrum of a peak at m/z 400.2
97 molecular structure of quinacrine that shows the spectrum 96
98 MS spectrum of the solvent that is available as the standard peaks for correction of peak intensities and the specific peaks that are used as the standard peaks in the spectrum of the solvent (enlarged FIG.
99 method of measuring ultralow sucked volume
100 the enlarged figure of the captured part at the top bore of the nanospray ionization capillary tip obtained by a microscope
101 methods for estimation of dilution rate on such as the addition of a slight amount of the solvent to sucked sample with ultralow volume
102 method of the addition of a slight amount of additive fluid from the back-end of the nanospray ionization capillary tip
103 method of suction of a slight amount of additive fluid from the top bore of the nanospray ionization capillary tip
104 figure enlarged by a microscope of the part of internal fluid at the top bore formed by the method of 102 or 103
105 nanospray ionization capillary tip with the simple joint part to suction devices to simplify the suction
106 an example of a set of tube to connect 105 and piston syringe (41) or pump for suction without vibration
107 an example of the device for introduction of the sample into a mass spectrometer by the nanospray ionization capillary tip after suction of the sample and addition of ionizing solvent by 105 (clamp type)
108 mass spectrum of each fraction of a cell before steroid treatment (three-dimensional representation)
109 mass spectrum of each fraction of a cell after steroid treatment (three-dimensional representation)
110 group of peaks decreased after treatment obtained by t-test (statistical evaluation of attribution to group) by using the difference between spectra 108 and 109.
The view of group of peaks specific before treatment of 95%
111 group of peaks increased after treatment obtained by t-test (statistical evaluation of attribution to group) by using the difference between spectra 108 and 109.
The view of group of peaks specific before treatment of 95%
112 the position where the peak at m/z 302.3 found in 111 found in TIC (total ion chromatogram) before steroid treatment
113 MS spectrum at that time (small peak)
114 enlarged figure of 113
115 the showing of the finding top bore in TIC (total ion chromatogram) after treatment where the peak at m/z 302.3 found in 111 was found in the case of after steroid treatment
116 MS spectrum at that time (large peak)
117 figure of t-test that shows the increase after treatment
118 MS/MS spectrum of a peak at m/z 302.3
119 MS/MS spectrum of dihydrosphingosine in data bank
120 structure of dihydrosphingosine
121 regression analysis for examining accordance of the intensity of a peak at m/z 302.3 and its response function of time (This analysis confirms that the peak intensity varies according to the response function.)
122 single cell mass spectra of seven types of cells and the score plot obtained by principal component analysis
123 loading plot obtained by principal component analysis of each peak in 122
124 contents of work and figure of linkage of data-processing system of this method
125 O-ring to prevent liquid spill
126 pressure pump
127 pump for nano LC
128 sample injector for nano LC
129 separation column for nano LC (pretreatment concentration column and combination of these columns are also available.)
130 detector for nano LC
131 nanospray emitter for nano LC
132 nano injection pressure syringe
133 single cell micro separation tip
134 micro channel for separation of single cell component (It is acceptable even if there is gel or resin.)
135 zone for concentration and electrophoresis of single cell component
136 sample inlet
137 electrode bath
138 conductive part for nanospray
139 micro separation capillary for single cell
140 example of nano separation of cells in different conditions: (a) before steroid treatment, (b) after steroid treatment
141 partial MS spectra obtained from a cell in each condition
142 well for cellular component analyses which double as cell culture well
143 cell culture fluid
144 filter for cell trapping 145 the bottom and the projecting tube part from center of bottom which is conductively-coated or which is conductive
146 step-by-step injection of cell fluid eluting ionizing solvent
147 eluting ionization solution for intracellular component
148 septum membrane (partition membrane)
149 nanospray needle (the conductive capillary tip which sticks into the bottom of well 142, breaks the septum membrane (148) and performs nanospray of eluting ionization solution of cellular component)
150 well plate for cellular component analyses which double as cell culture well plate
151 pump for sending solution
152 pump for sending solution for sheath flow
153 sheath flow
154 nebulizer for atomic absorption or ICP plasma introduction
155 cell detection part of cell sorter
156 laser source of the detection part of cell sorter
157 stopper of laser source
158 forward laser small-angle scattering light
159 detector of forward laser small-angle scattering light
160 cell flowing one by one in cell sorter
161 sheath flow
162 edge charged electrode
163 single cell in charged droplet
164 timing pulsar driving device
165 high voltage pulses to form charged droplets each of which contains a single cell (They are called + or − or uncharged based on the detection results of cellular characteristics.)
166 sending positive high voltage pulses or negative high voltage pulses to the pulse nanospray or the pulse electrode or the pulse laser as the signal in synchronized timing of the fall of charged droplets each of which contains a single cell
167 device of pulse nanospray of ionizing solvent
168 electrode for applying the spatial pulse electric field
169 ionizing pulse laser
170 droplet with a single cell changes to smaller droplet by pulse wave that is introduced into mass spectrometer
171 positive high voltage pulse synchronized timing of a fall of positive charged droplet with a single cell
172 mass spectrometer for positive mode only
173 negative high voltage pulse synchronized timing of a fall of negative charged droplet with a single cell
174 mass spectrometer for negative mode only
175 positive charged droplet with single cell changes to smaller positive charged droplets by pulse wave
176 negative charged droplet with single cell changes to smaller negative charged droplets by pulse wave
177 cell sorter
178 control and data analysis system of cell sorter and mass spectrometer
179 monitor of scatter diagram and density diagram by cell sorter
180 monitor displaying the results of principal component analysis and MS spectra obtained by mass spectrometer simultaneously
181 personal computer
182 Scatter diagram of blood cells
183 Density diagram of fluorescent marker selecting only lymphocyte cells
184 Result of principal component analysis determined from MS spectra of selected lymphocyte cells on positive mode (It is understood that there are three groups.)
185 MS spectrum of three groups which the lymphocyte cells were divided into by the principal component analysis
200 Microscopic images of the moment of popping granules at allergy reaction of allergic cells observed by the video camera (figure below is captured as light field image and the granule indicated by an arrow is disappeared in lower right figure. Figure above is to see the disappearance of the granules by allowing fluorescent substances to enter the granules; the granules indicated by arrows (left) are disappeared (right).)
201 One of the images of continuous temporal difference image analyses of the video images of light field images such as the figure below of FIG. 200; only the granules which are moving in the images at the moment of granule disappearance are extracted as a differential picture
202 Figure showing the time course of count of popped granules of the cells in the same conditions in the microscope field by image analyses such as FIG. 201
203 Mass spectrum of the components contained in a single granule of a RBL-2H3 cell
204 Mass spectrum of the components contained in a cytoplasm of RBL-2H3 cell
205 Enlarged figure of the spectrum near m/z 112 (t-value is described below) in the components contained in the single granule of RBL-2H3 cell
206 Enlarged figure of the spectrum near m/z 156 (t-value is described below) in the components contained in a single granule of RBL-2H3 cell
207 Enlarged figure of the spectrum near m/z 177 (t-value is described below) in the components contained in the single granule of RBL-2H3 cell
208 Enlarged figure of the spectrum near m/z 177 (t-value is described below) in the components contained in the cytoplasm of a RBL-2H3 cell
209 Enlarged figure of the spectrum near m/z 205 (t-value is described below) in the components contained in the cytoplasm of a RBL-2H3 cell
210 Enlarged figure of the spectrum near m/z 221 (t-value is described below) in the components contained in the cytoplasm of a RBL-2H3 cell
211 MS/MS spectrum of the peak of m/z 156 in the components contained in a RBL-2H3 cell
212 MS/MS spectrum of the peak of m/z 112 in the components contained in a RBL-2H3 cell
213 MS/MS spectrum of the peak of m/z 205 in the components contained in a RBL-2H3 cell
214 MS/MS spectrum of the peak of m/z 221 in the components contained in a RBL-2H3 cell
215 MS/MS spectrum of the peak of m/z 177 in the components contained in a RBL-2H3 cell
216 Pattern diagram of the intracellular localization of tryptophan metabolites and histidine metabolites in the cell obtained from the single cell analysis by this invention
217 Metabolic map of histidine metabolites in the single granule obtained by the direct molecular analysis of single cell and single granule by this invention.
218 Image of popping granules at stimulation by calcium ionophore to a RBL-2H3 cell.
219 Spectrum of captured extracellular components after stimulation with calcium ionophore to a RBL-2H3 cell 220 in 219, the enlarged figure near the peak of histamine and the structure formula of histamine 223 Morphology of P19 cells before induction of cellular differentiation by retinoic acid and taking single cell sample recovery.

224 Morphology of neuronally-differentiated P19 cells after induction of cellular differentiation by retinoic acid and taking single cell sample selectively 225 Single cell mass spectrum before induction of cellular differentiation of P19 cell by retinoic acid.

226 Single cell mass spectrum after induction of cellular differentiation of P19 cell by retinoic acid.

227 m/z showing t-value specific to after induction of differentiation and t-values before and after induction of differentiation above 228 MS/MS spectrum of spectrum peaks in 227 and the structure of identified molecule 229 Differentiation step dependence of peak intensity of m/z 118.1 above-described 230 Image of observation of taking single cell of HepG2 by a video camera 231 Metabolic process of medical substances of a drug, quinacrine 232 Spectrum of metabolite of medicinal substance of quinacrine in a single cell 233 Blood sampling of a drop from an earlap using a needle for injection 234 A needle for inserting (metal)

235 Blood

236 Added ionization supporting solvent

237 Mass spectrum of direct blood sampling by this invention

238 Spectrum of ionization supporting solvent alone for comparison

239 Appearance of the enlarged figure of a leaf of plant (Geranium) by the microscope and taking single cell sample directly 240 Detected mass spectrum by this invention by taking single cell directly from a leaf of plant (Geranium)

241 Appearance of the enlarged figure of a stem of plant (geranium) by the microscope and taking single cell sample directly 242 Detected mass spectrum by this invention by taking single cell directly from a stem of plant (geranium)

243 Peaks specific to leaf and peaks specific to stem by t-test

244 Appearance of m/z 178 localization in leaf and stem

245 Appearance of m/z 311 localization in leaf and stem

246 Stable isotope-labeled histidine

247 Mass spectrum of rat mast cell left in the medium containing stable isotope labeled histidine.

248 Peaks of Histidine and its isotope peaks (1 minute after the injection of stable isotope)

249 Peaks of Histidine and its isotope peaks (10 minutes after the injection of stable isotope)

250 the peaks of Histidine and its isotope peaks (60 minutes after the injection of stable isotope)

251 Peaks of Histamine, one of the Histidine metabolites, and its isotope peaks (1 minute after the injection of stable isotope)

252 Peaks of Histamine, one of the Histidine metabolites, and its isotope peaks (10 minutes after the injection of stable isotope)

253 Peaks of Histamine, one of the Histidine metabolites, and its isotope peaks (60 minutes after the injection of stable isotope)

254 Total ion chromatogram (TIC) at the measurement of single cell sample by the nanospray ionization capillary tip (the capillary tip) which has the capillary wire for solvent flow channel inside 255 Total ion chromatogram (TIC) at the measurement of single cell sample by the available nanospray ionization capillary tip (the capillary tip) without the capillary wire for solvent pathway inside 256 Appearance of extracted and eluted molecular components which were precipitated by the added ionization supporting solvent in the cellular component fluid captured at the forefront; they are extracted and eluted from high molecular components to low molecular components with the movement to the forefront of the ionization supporting solvent by spraying 257 Appearance of extracted and eluted molecular components which were captured by the molecular affinity groups on the inner surface of the forefront in the cellular component fluid captured at the forefront; they are extracted and eluted with the movement to the forefront of the ionization supporting solvent by spraying 258 Appearance of extracting and eluting process of molecular components which were initially captured by molecular affinity groups on the resin surface filled at the forefront inside included in the cellular component fluid: they are extracted and eluted along with the movement of the ionization supporting solvent after spraying 259 Applied high direct voltage 260 Applied high pulse voltage 261 Sinusoidal voltage overlaid to high-voltage direct bias 262 Square wave voltage overlaid to high-voltage direct bias 263 Sawtooth-waved voltage overlaid to high-voltage direct bias 264 Sample plate for MALDI-TOF 265 Addition of matrix solution for laser desorption/ionization after spotting or nanospray spotting of intracellular component fluid of single cell 266 MALDI-TOF mass spectrum of single cell components

What is claimed:

1. A method for capturing cellular components from a single cell and performing mass spectrometry on the components, said method comprising:

inserting a nanospray ionization capillary tip into a specific region of the cell under observation, whose opening diameter is corresponding to the specific region of the cell under observation with a microscope, wherein the nanospray ionization capillary tip comprises a filament in the interior, capturing the cellular components of the specific region of the cell into the opening of the nanospray ionization capillary tip and keeping the components at the nanospray ionization capillary tip, supplying an ionization supporting solvent from a back-end of the nanospray ionization capillary tip, applying an electric field between a sample inlet of a mass spectrometer and the nanospray ionization capillary tip, whereby nanospray ionization to the cellular components is implemented, and performing the mass spectrometry on the cellular components captured at the nanospray ionization capillary tip.

2. The method in accordance with claim 1, wherein the diameter of the opening of the nanospray ionization capillary tip is from 0.1 to 100 micrometer.

3. The method in accordance with claim 1 wherein at least one of outer or inner surface of the nanospray ionization capillary tip is electro-conductive, or the nanospray ionization capillary tip contains a thin electro-conductive filament extending from rear side of the tip to inner side of the top of the tip.

4. The method in accordance with claim 1, wherein the outer surface of the nanospray ionization capillary tip is hydrophobic when target cells have a cell membrane, and the outer surface of the nanospray ionization capillary tip is hydrophilic when the target cells have both a cell membrane and a cell wall.

5. The method in accordance with claim 1, wherein the inner surface of the nanospray ionization capillary tip is coated or combined with groups with molecular affinity for capturing a specific molecule.

6. The method in accordance with claim 1, wherein the inside of the nanospray ionization capillary tip is pressurized until the tip comes close to the cell under the observation in order to prevent the contamination by peripheral substances including culture medium, and the pressurization is deactivated after the opening of the tip is inserted into the observing cell.

7. The method in accordance with claim 1, wherein the opening of the nanospray ionization capillary tip captures the cellular components for the mass spectrometry by leaking internal components of the cell or an organelle through hole(s) formed thereon.

8. The method in accordance with claim 1, wherein a manipulator, which controls the three dimensional position of the nanospray ionization capillary tip, is placed back end of the nanospray ionization capillary tip so that the manipulator is set between the cell under observation and the mass spectrometer, said manipulator leads the nanospray ionization capillary tip to the point of the target cell under the observation for mass spectroscopic analysis, and the manipulator leads the nanospray ionization capillary tip to the sample inlet of the mass spectrometer when the captured cell components are subjected to mass spectroscopic analysis.

9. The method in accordance with claim 1, wherein the step of capturing cellular components comprises capturing a plurality of cellular components, at different spatial locations, at different time sequential stages, or before and after each of treatments to the cell when multiple different treatments are performed on the cell, and the step of performing the mass spectrometry comprises performing a plurality of the mass spectrometry to the captured cellular components at the different spatial locations, or at the different time sequential stages or before and after the treatments to obtain the mass spectra and evaluating the difference between each spectrum, so that molecules which relate to the spatial and time difference are evaluated and identified.

10. The method in accordance with claim 1, wherein the step of performing mass spectrometry comprises:
storing mass spectra of known samples into computer(s),
obtaining the mass spectrum of the captured cellular components during the nano-spray ionization,
analyzing the cell components by extracting difference between the known and the obtained spectrum so as to obtain a specific peak of mass spectrometry, and
applying a higher order mass spectrometry to molecules, which shows the specific peak of mass spectrometry, selected from the cellular components by mass filtering for identification of the molecules.

11. The method in accordance with claim 1, wherein the filament comprises glass.

12. A system for capturing cellular components from a single cell and performing mass spectrometry on the components said system comprising:
a microscope to observe the dynamic morphological change of cells which are subjected to mass spectroscopic analysis,
nanospray ionization capillary to ionize the cellular components for the mass spectrometry, said nanospray ionization capillary further comprising a tip portion having an opening and a filament in the interior, for capturing the cellular components of a specific region of the cell by inserting the tip to the specific region of the cell, whose size is not bigger than the size of the specific region of the cell, and a back side portion from which ionization supporting solvent is supplied,
a mass spectrometer which has a sample inlet hole to analyze the cellular components after the ionization, and
a high voltage power supply which applies an electric field between the sample inlet and the nanospray ionization capillary,
wherein the nanospray ionization capillary tip is configured to penetrate into the cell under observation of the microscope to capture the cell components from the specific region of the cell, the captured components are ionized by applying the electric field between the nanospray ionization capillary and the inlet hole of the mass spectrometer and wherein the system is configured to introduce the solvent into back side portion of the nanospray ionization capillary.

13. The system in accordance with claim 12, wherein the diameter of the opening of the nanospray ionization capillary tip is from 0.1 to 100 micrometer.

14. The system in accordance with claim 12, wherein at least one of outer or inner surface of the nanospray ionization capillary is electro-conductive, or the high voltage power supply further comprising an electro-conductive fine wire extending from the back side of the nanospray ionization capillary to the tip of the nanospray ionization capillary.

15. The system in accordance with claim 12, wherein the outer surface of the nanospray ionization capillary is hydrophobic when target cells have a cell membrane, and the outer surface of the nanospray ionization capillary is hydrophilic when the target cells have both a cell membrane and a cell wall.

16. The system in accordance with claim 12, wherein the inner surface of the tip of the nanospray ionization capillary tip is coated or combined with groups with molecular affinity for capturing a specific molecule.

17. The system in accordance with claim 12, wherein the inside of the nanospray ionization capillary is pressurized until the tip comes close to the cell under the observation in order to prevent the contamination by peripheral substances including culture medium, and the pressurization is deactivated after the opening of the tip is inserted into the observing cell.

18. The system in accordance with claim 12, wherein a manipulator, which controls the three dimensional position of the nanospray ionization capillary tip, is disposed back end of the nanospray ionization capillary so that the manipulator is set between the cell under observation and the mass spectrometer, said manipulator leads the nanospray ionization capillary tip to the point of the target cell under the observation for mass spectroscopic analysis, and the manipulator leads the nanospray ionization capillary tip to the sample inlet hole of the mass spectrometer when the captured cell components are subjected to mass spectroscopic analysis.

19. The system in accordance with claim 12, wherein the nanospray ionization capillary tip is configured to capture cellular components at different spatial locations, or at different time sequential stages, or before and after each of treatments to the cell when multiple different treatments are performed, and the mass spectrometer is configured to obtain the mass spectra of the captured cellular components at the different spatial locations, or at the different time sequential stages or before and after the treatments, and to extract the difference between each spectrum, so that molecules which relate to the spatial and time difference are evaluated and identified.

20. The system in accordance with claim 12, wherein the mass spectrometer comprises computer(s) configured to store mass spectra of known samples and said mass spectrometer is configured to analyze the cell components by extracting a difference between the mass spectra of the known samples and a spectrum of the captured cellular components so as to obtain a specific peak of mass spectrometry, and to apply a higher order mass spectrometry to molecules, which shows the specific peak of mass spectrometry, selected from the cellular components by mass filtering, for identification of the molecules.

21. A method for capturing cellular components from a single cell and performing mass spectrometry on the components, said method comprising:
    inserting a nanospray ionization capillary tip into a specific region of a cell whose opening diameter is not bigger than a size of the specific region of the cell, wherein the nanospray ionization capillary tip comprises a filament in the interior,
    capturing the cellular components in the specific region with the tip of the nanospray ionization capillary,
    supplying ionization supporting solvent from a back-end of the nanospray ionization capillary, keeping the components at the tip,
    applying an electric field between a sample inlet of a mass spectrometer and the nanospray ionization capillary tip whereby the cellular components are ionized and introduced to the mass spectrometer, and
    performing the mass spectrometry to the introduced cellular components.

22. A system for capturing cellular components from a single cell and performing mass spectrometry on the components, said system comprising:
    a nanospray ionization capillary to ionize the cellular components for the mass spectrometry, said nanospray ionization capillary further comprising a tip portion having an opening and a filament in the interior, for capturing the cellular components of a specific region of the cell by inserting the tip into the specific region of the cell for capturing the cellular components whose size is not bigger than the size of the specific region of a cell, and a back side portion from which ionization supporting solvent is supplied,
    a mass spectrometer which has a sample inlet hole to analyze the cellular components after the ionization,
    a high voltage power supply which applies an electric field between the sample inlet and the nanospray ionization capillary,
    wherein the nanospray ionization capillary tip penetrates into the cell to capture the cellular components, the captured components are ionized by applying the electric field between the nanospray ionization capillary and the inlet hole of the mass spectrometer, and wherein the system is configured to introduce the solvent into the back side portion of the nanospray ionization capillary.

23. A method for capturing biological fluids or liquids in less than micro meter region and performing mass spectrometry to thereof, said method comprising:
    inserting a nanospray ionization capillary tip into a specific region of a cell whose opening diameter is not bigger than a size of the specific region of the cell, wherein the nanospray ionization capillary tip comprises a filament in the interior,
    capturing components in the specific region with the tip of the nanospray ionization capillary and keeping the components at the tip,
    supplying an ionization supporting solvent from a back-end of the nanospray ionization capillary,
    ionizing the components using nanospray ionization by applying an electric field between a sample inlet of a mass spectrometer and the nanospray ionization capillary tip introducing the ionized components into the mass spectrometer, and,
    performing mass spectrometry on the introduced cellular components.

24. A system for capturing biological fluids or liquids in less than micro meter region and performing mass spectrometry to thereof, said system comprising:
    a nanospray ionization capillary to ionize cellular components for the mass spectrometry, said nanospray ionization capillary further comprising a tip portion having an opening and a filament in the interior, for capturing the cellular components of a specific region of the biological fluids or liquids by inserting the tip into a specific region of a cell, whose size is not bigger than the size of the specific region of the cell, and a back side portion from which ionization supporting solvent is supplied,
    a mass spectrometer which has a sample inlet hole to analyze the cellular components after the ionization,
    a high voltage power supply which applies an electric field between the sample inlet and the nanospray ionization capillary,
    wherein the nanospray ionization capillary tip penetrates into the cell to capture the cellular components, the captured components are ionized by applying the electric field between the nanospray ionization capillary and the inlet hole of the mass spectrometer, and wherein the system is configured to introduce the solvent into back side portion of the nanospray ionization capillary.

* * * * *